United States Patent [19]

Brown et al.

[11] Patent Number: 5,256,545

[45] Date of Patent: * Oct. 26, 1993

[54] STEROL REGULATORY ELEMENTS

[75] Inventors: Michael S. Brown; Joseph L. Goldstein; David W. Russell; Thomas C. Sudhof, all of Dallas, Tex.

[73] Assignee: Board of Regents, The University of Texas System, Austin, Tex.

[*] Notice: The portion of the term of this patent subsequent to Jun. 19, 2007 has been disclaimed.

[21] Appl. No.: 425,852

[22] Filed: Oct. 20, 1989

Related U.S. Application Data

[63] Continuation of Ser. No. 33,332, Mar. 30, 1987, Pat. No. 4,935,363, and a continuation of Ser. No. 33,081, Mar. 30, 1987.

[51] Int. Cl.$^5$ ............ C12N 15/11; C12N 15/63; C12N 5/10
[52] U.S. Cl. ............... 435/69.1; 435/172.3; 435/240.2; 435/252.3; 435/320.1; 536/24.1; 935/36; 935/43
[58] Field of Search ............... 435/69.1, 70.1, 91, 435/172.3, 240.2, 320.1, 252.3; 536/24.1; 935/6, 8, 9, 22, 24, 33, 41, 34, 36, 59, 60, 61, 66, 70

[56] References Cited

U.S. PATENT DOCUMENTS

| | | | |
|---|---|---|---|
| 4,579,821 | 4/1986 | Palmiter et al. | 435/172.3 |
| 4,738,922 | 4/1988 | Haseltine et al. | 435/68 |
| 4,745,060 | 5/1988 | Brown et al. | 435/172.3 |
| 4,775,630 | 10/1988 | Tibbetts et al. | 435/320 |

FOREIGN PATENT DOCUMENTS 118393A 9/1984 European Pat. Off.
WO83/01783 5/1983 PCT Int'l Appl.

OTHER PUBLICATIONS

Godowski et al. (1987), *Nature*, 325:365.
DeFranco et al. (1986), *Mol. Cell. Biol.*, 6:993.
Jones et al. (1986), *Science*, 232:755.
Kadonaga et al. (1986), *Trends Biochem. Sci.*, 11:20.
Yamamoto (1985), *Ann. Rev. Genet.*, 19:209.
Goodbourn et al. (1985), *Cell*, 41:509.
Gidoni et al. (1985), *Science*, 230:511.
Stuart et al. (1985), *Nature*, 317:828.
Searle et al. (1985), *Mol. Cell. Biol.*, 5:1480.
Sudhof et al. (1985), *Science*, 228:815.
Stuart et al. (1984), *Proc. Natl. Acad. Sci. USA*, 81:7318.
Chandler et al. (1983), *Cell*, 33:489.
Price et al. (1987), *Proc. Natl. Acad. Sci. U.S.A.*, 84:156–160.
Matteuci et al. (1986), *Biotechnology*, 7:51–55.
Goring et al. (1987), *Science*, 235:456–458.
Kalnins et al. (1983), *The EMBO Jrnl.*, 2(4):593–597.
Hall et al. (1983), *Jrnl. Mol. App. Gen.*, 2(1):101–109.
PCT Search Report for PCT/US 88/01095.
Kirston et al. (1974), *Jrnl. Biol. Chem.*, 249:6104–6109.

(List continued on next page.)

*Primary Examiner*—Richard A. Schwartz
*Assistant Examiner*—J. LeGuyader
*Attorney, Agent, or Firm*—Arnold, White & Durkee

[57] ABSTRACT

Disclosed are discrete functionally translocatable DNA segments, termed Sterol Regulatory Elements (SREs), which are fused to heterologous structural genes to provide sterol regulatory capability to the thus formed hybrid gene. The hybrid genes respond to sterols by decreasing the production of messenger RNA. The SRE segments contain as their primary functional nucleotide sequence, a 16 bp sequence referred to as direct repeat 2, isolated from the 5' regions of the human LDL receptor gene. DNA segments which include this 16 nucleotide long sequence similarly confer sterol regulatory capability to previously known promoters such as the HSV TK promoter. Also disclosed are discrete sequences which confer positive transcription promotion to heterologous structural genes and promoters without conferring sterol responsivity. Methods are disclosed for employing these genetic control elements in a myriad of embodiments which provide for a fine-tune control of heterologous genes. Methods are also disclosed for employing the SRE in a screening assay for drugs capable of stimulating the cell to synthesize LDL receptors.

24 Claims, 18 Drawing Sheets

OTHER PUBLICATIONS

Reynolds et al. (1984), *Cell*, 38:275–285.
John et al. (1984), *Proc. Natl. Acad. Sci. USA*, 81:5628–5632.
Reynolds et al. (1985), *Jrnl. Biol. Chem.*, 260:10369–10377.
Chin et al. (1985), Mol. Cell. Biol., 5:634–641.
Gil et al. (1986), *Jrnl. Biol. Chem.*, 261:3717–3724.
Darnell et al. (1986), *Molecular Cell Biology*, Scientific American Books, Inc., pp. 343–353.
Sudhof et al. (1987), Cell, 48:1061–1069.
Sudhof et al. (1987), *Jrnl. Biol. Chem.*, 262:10773–10779.
Smith et al., "Multiple Sterol Regulatory Elements in Promoter for Hamster 3-Hydroxy-3-methyl-glutaryl-coenzyme A. Synthase," J. Biol. Chem., 263:18480–18487 (1988).
Klock et al., *Nature*, 329:734–736 (1987).
Firak et al., *Molecular and Cellular Biology*, 6:3667–3676 (1986).
Osborne et al., "5' End of HMG CoA Reductase Gene Contains Sequences Responsible for Cholesterol-Mediated Inhibition of Transcription" *Cell*, 42:203–212 (1985).
Ringold et al., "Glucocorticoid Regulation of Gene Expression," *Prog. Cancer Res. Ther.*, 31:7–18 (1984).
Rajavashisth, et al., (1989) *Science*, 245:640–643.
Dawson et al., (1989) *The Journal of Biological Chemistry*, 264:16798–16803.
Metherall et al., (1989) *The Journal of Biological Chemistry*, 264:15634–15641.
Dawson et al., (1989) *The Journal of Biological Chemistry*, 264:9046–9052.
Gil et al., (1988) *The Journal of Biological Chemistry*, 263:19009–19019.
Gil et al., (1988) *Proc. Natl. Acad. Sci. USA*, 85:8963–8967.
Osborne et al., (1988) *The Journal of Biological Chemistry*, 7:3380–3387.
Dawson et al., (1988) *The Journal of Biological Chemistry*, 7:3372–3379.
Osborne et al., (1987) *Proc. Natl. Acad. Sci. USA*, 84:3614–3618.
Ma et al., (1986) *Proc. Natl. Acad. Sci USA*, 83:8370–8374.
Gil et al., (1986) *The Journal of Biological Chemistry*, 8:3710–3716.
Ma et al., (1986) *Proc. Natl. Acad. Sci USA*, 83:792–796.
Yamamoto et al., (1984) *Cell*, 39:27–38.
Dawson et al., (1988) *The Journal of Biological Chemistry*, 263:3372–3379.
Osborne et al., (1988) *The Journal of Biological Chemistry*, 263:3380–3387.

FIG. 1A

```
                                                          -240 TCAGAGCTTCACGGGGTAAA AGCCGATGTCACATCGGCCG -201
         Repeat 1                                   SRE 42
-200 TTCGAAACTCCTCCTCTGC AGTGAGGTGAAGAGACATTGA AAATCACCCCACTCGCAAACT CCTCCCCCTGCTAGAAACCT CACATTGAAATGCTGTAAAT -101
                          ** * * **                            Repeat 2            Repeat 3
-100 GACGTGGGGCCCCCGAGTGCAA TCGCGGGAAGCCAGGGTTTC CAGCTAGGACACAGCAGGTC GTGATCCGGGGTCGGGACACT GCCTGGCAGAGGCTGCGAGC -1
+1 ATG GGG CCC
   Met Gly Pro
```

FIG. 1B

| | | | | | | | | | | | | | | | | | | | |
|---|---|---|---|---|---|---|---|---|---|---|---|---|---|---|---|---|---|---|---|
| Repeat 1 | A | A | A | C | T | C | C | T | C | C | T | C | T | T | G | C | | | |
| Repeat 2 | A | A | A | T | C | A | C | C | C | C | A | C | T | G | C | | | | |
| Repeat 3 | A | A | A | C | T | C | C | T | C | C | C | C | C | T | G | C | | | |

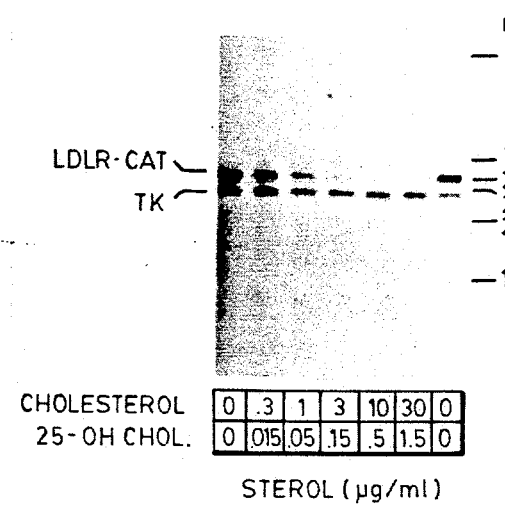
FIG. 4A
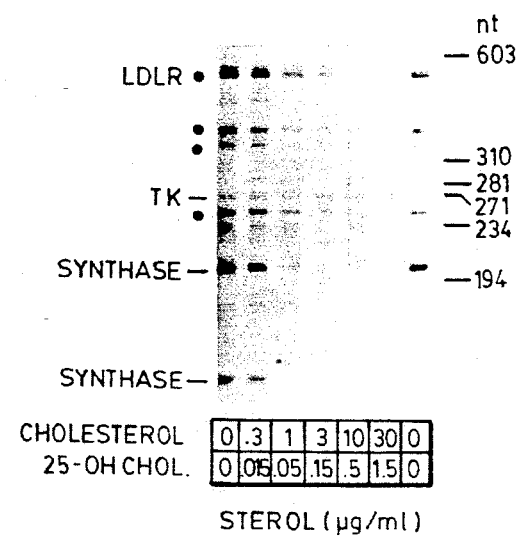
FIG. 4B
FIG. 6
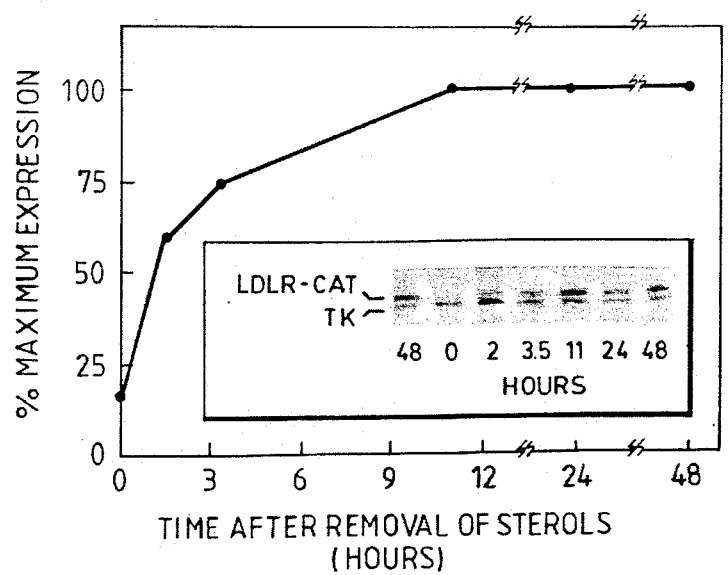

FIG. 7B

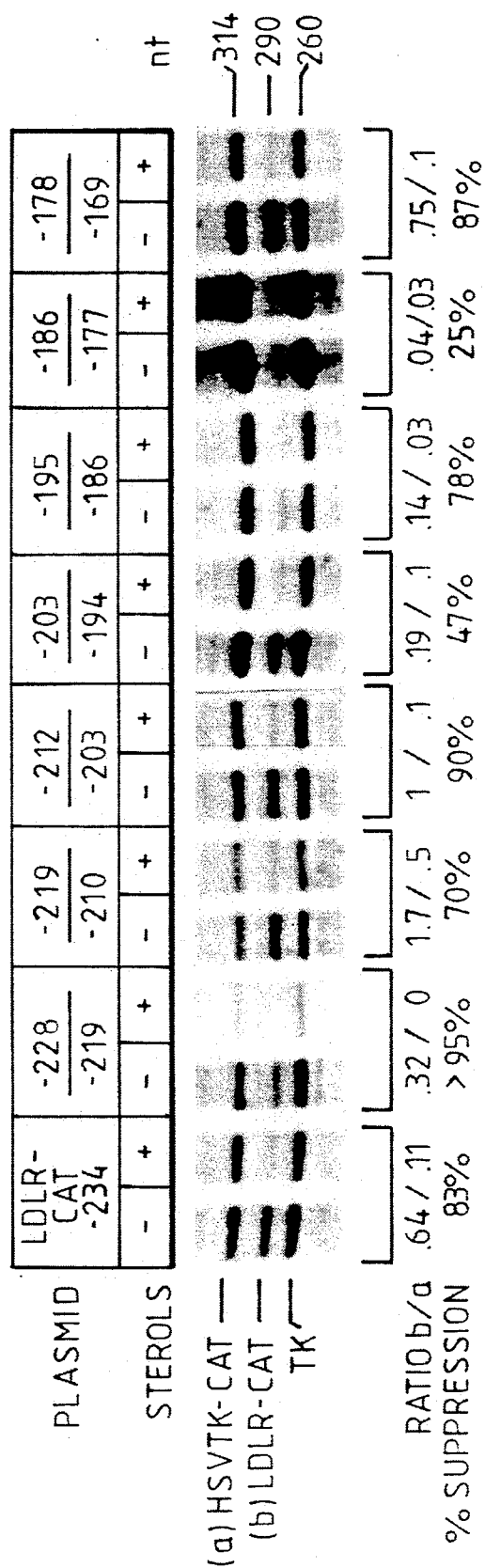

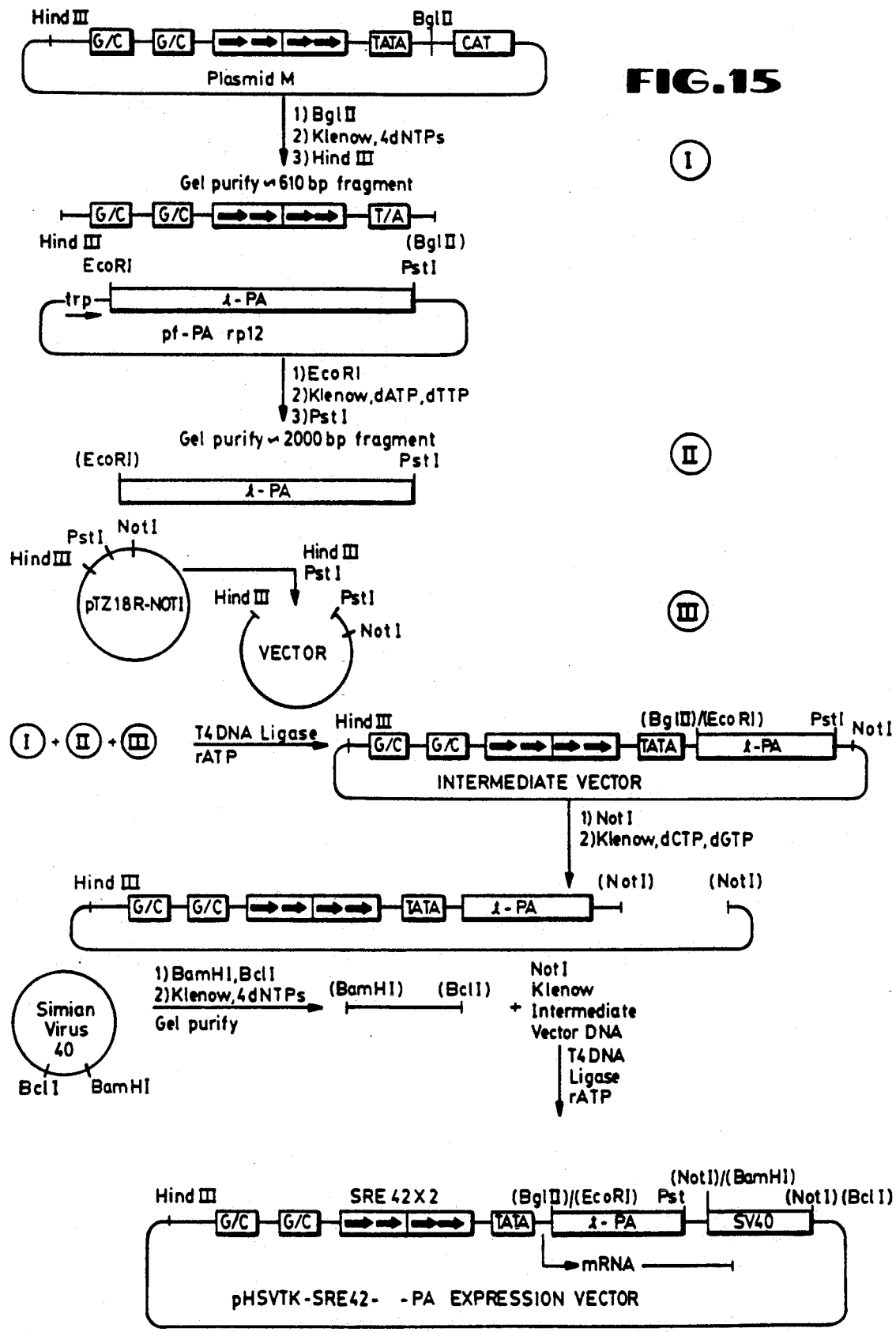

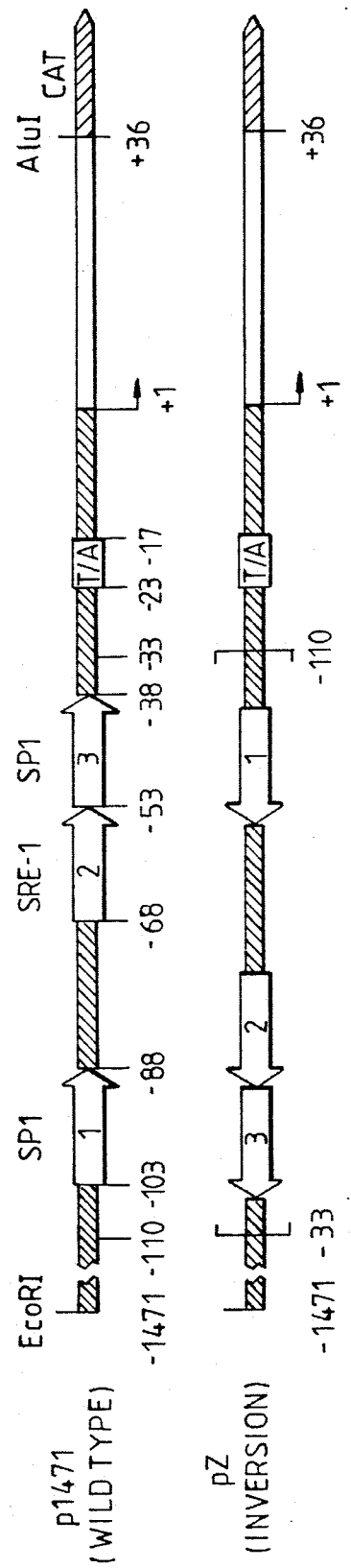
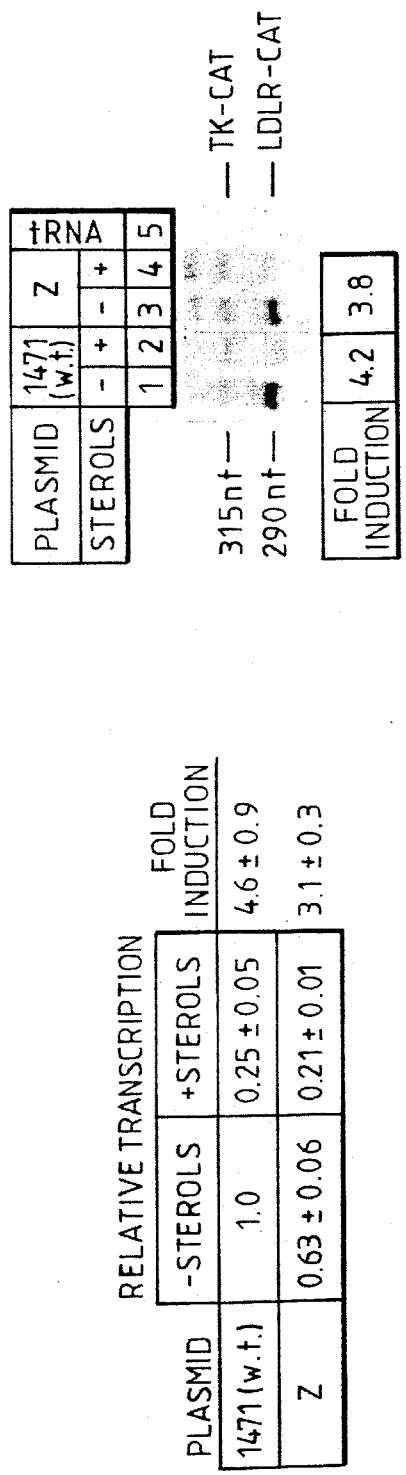
FIG.16A
FIG.16B

STEROL REGULATORY ELEMENTS

The government may own certain rights in the present invention pursuant to NIH grantL HL 20948.

This application is a continuing application of U.S. Ser. Nos. 07/033,302, now U.S. Pat. No. 4,935,363, and 07/033,081, both filed Mar. 30, 1987.

BACKGROUND OF THE INVENTION

1. Field of the Invention

The present invention relates to DNA segments which may be employed as functionally translocatable genetic control elements. More particularly, the invention relates to sterol regulatory elements and promoter sequences which serve to promote transcription and/or confer a sterol-mediated suppression capability to selected structural genes.

2. Description of the Related Art

In the 25 years since Jacob and Monod first proposed the lac operon model and the concept of messenger RNA (see, Jacob et al. (1961), *J. Mol. Biol.*, 3: 318-350), the structure and function of a number of prokaryotic operons has been elucidated in elegant detail. For example, in the case of the lac operon, it has been shown that transcriptional control of the various structural genes of the operon (e.g., B-galactosidase) resides in an upstream (i.e., 5' with respect to the structural genes) regulator gene and operator gene. The regulator gene produces a protein "repressor" that interacts with the operator to prevent transcription initiation of the structural gene. Inducers such as IPTG (isopropyl thiogalactoside) bind to the repressor and thereby induce transcription by preventing the binding of the repressor to the operator. Additionally, there is a promoter site P, upstream of the operator and downstream of the regulatory gene, which serves as an RNA polymerase binding site.

Studies on the lac operon further have led to the discovery and elucidation of the mechanism of prokaryotic catabolic suppression. In *E. coli* it is found that the catabolic suppress presence of glucose in the growth medium serves to shut down the expression of gluconeogenic pathways, including the lac operon and its associated structural genes. The mechanism of this catabolic suppression is not entirely clear, but appears to involve a glucose-mediated suppression of cyclic AMP-mediated stimulation of transcription. In this regard, it appears as though cyclic AMP complexes with a protein known as catabolic gene activator protein (CAP), and this complex stimulates transcription initiation. Thus, in the presence of glucose, the activator CAP complex is not formed and transcription is not enhanced.

In addition to the lac operon, the mechanism and structure of numerous additional prokaryotic control mechanisms have been elucidated. (e.g., see Miller et al. (eds.), 1978, The Operon. Cold Spring Harbor Laboratory; Wilcox et al. (1974), *J. Biol. Chem.*, 249: 2946-2952 (arabinose operon); Oxender et al. 1979), *Proc. Natl. Acad. Sci., U.S.A.*, 76: 5524-5528 (trp operon); Ptashne et al. (1976), *Science*, 194: 156-161 (lambda phage)).

Unfortunately, in contrast to prokaryotic systems, very little is presently known about the control mechanisms in eukaryotic systems. Moreover, although, as noted, the mechanisms for feedback suppression of mRNA production in prokaryotes have been elucidated in elegant detail (see e.g., Ptashne, M. (1986) *A Genetic Switch: Gene Control and Phage Lambda*. Cell Press and Blackwell Publications, Cambridge, Mass. and Palo Alto, Calif. pp. 1-128), little is known about analogous mechanisms in higher eukaryotes. In animal cells most attention has focused on positively-regulated systems in which hormones, metabolic inducers, and developmental factors increase transcription of genes. These inducing agents are generally thought to activate or form complexes with proteins that stimulate transcription by binding to short sequences of 10 to 20 basepairs (bp) in the 5'-flanking region of the target gene. These elements have been called GRE, MRE, or IRE for glucocorticoid regulatory element, metal regulatory element, and interferon regulatory element, respectively (Yamamoto (1985), *Ann. Rev. Genet.*, 19: 209-252; Stuart et al. (1984), *Proc. Natl. Acad. Sci. USA*, 8: 7318-7322; Goodbourn et al. (1986), *Cell)*, 45: 601-610).

Accordingly, there is currently very little knowledge concerning eukaryotic genetic control mechanisms and, in particular, little knowledge concerning genetic elements controlled by feedback regulation. The availability of discreet DNA segments which are capable of conferring either a negative or positive control capability to known genes in eukaryotic systems would constitute an extremely useful advance. Not only would such elements be useful in terms of furthering our understanding of eukaryotic gene control in general, but would also provide biomedical science with powerful tools which may be employed by man to provide "fine-tune" control of specific gene expression. The elucidation of such elements would thus provide science with an additional tool for unraveling the mysteries of eukaryotic gene control and lead to numerous useful applications in the pharmaceutical and biotechnical industries.

Although the potential applications for such control sequences are virtually limitless, one particularly useful application would be as the central component for screening assays to identify new classes of pharmacologically active substances which may be employed to manipulate the transcription of structural genes normally under the control of such control sequences. For example, in the case of hypercholesterolemia, it would be desirable to identify therapeutic agents having the ability to stimulate the cellular production of Low Density Lipoprotein (LDL) receptors, which would in turn serve to lower plasma LDL (and consequently cholesterol) by increasing the cellular uptake of LDL.

Currently, there are few cholesterol-lowering drugs that are both safe and efficacious, and no drugs which are known to operate at the above-described genetic control level. For example, aside from agents that function by sequestering bile salts in the gut and thereby increase cholesterol excretion, the principal therapeutic agent available for cholesterol lowering is Lovastatin, a drug manufactured by Menck, Co. that acts indirectly to stimulate production of LDL receptors.

Specifically, Lovastatin and other drugs in this class (Simvastatin, Pravastatin) act by inhibiting the activity of HMG CoA reductase, the rate-limiting enzyme of endogenous cholesterol synthesis. These drugs contain side chains that resemble the native substrate for HMG CoA reductase and thus competitively inhibit the activity of the enzyme. Eventually this lowers the endogenous synthesis of cholesterol and, by normal homeostatic mechanisms, plasma cholesterol is taken up by increased LDL receptor populations in order to restore the intracellular cholesterol balance. Conceptually, HMG CoA reductase inhibitors are acting at the penultimate stage of cellular mechanisms for cholesterol metabolism. It would be most desirable if the synthesis of LDL receptor could be directly upregulated at the gene level. The upregulation of LDL receptor synthesis at the gene level offers the promise of resetting the level of blood cholesterol at a lower and clinically more desirable level (Brown et al. (1984), *Scientific American*, 251:58-60). However, no methods exist for conveniently assaying the ability of a candidate composition to exert such an effect on the transcription of the LDL receptor gene.

Accordingly it is a further object herein to provide a method for conveniently evaluating candidate substances for receptor upregulating activity.

SUMMARY OF THE INVENTION

In its most general and overall scope, the present invention is directed to DNA segments which, when located upstream from and proximal to a transcription initiation site of a selected structural gene, serve to confer a sterol-mediated suppression capability to such a gene. These DNA segments, termed Sterol Regulatory Elements (SREs), have been identified and constructed from a consideration and manipulation of DNA sequences found in the gene regions upstream of the transcription initiation site of structural genes that are subject to sterol mediated regulation, such as the HMG-CoA (3-hydroxy-3-methylglutaryl-coenzyme A) reductase or HMG-CoA synthase genes, or the gene encoding the LDL receptor protein (Low Density Lipoprotein Receptor). For the purposes of the present disclosure, these genes will be referred to collectively as the "sterol regulated structural genes". Moreover, as used herein, the term "upstream" refers to DNA sequences found in a 5' direction from a given point of reference along a DNA molecule.

The LDL receptor gene is the structural gene which provides for the production of the LDL receptor protein, the receptor protein responsible for the facilitated uptake of cholesterol by mammalian cells. In the context of the LDL receptor gene, these SRE sequences provide a sterol-mediated regulation of LDL receptor gene transcription. Thus, in the relative absence of sterols within the cell, transcription of the LDL receptor gene is promoted, whereas in the presence of cholesterol, transcription is suppressed. In contrast to the LDL receptor gene, the HMG-CoA synthase and reductase genes encode enzymes in the cholesterol biosynthetic pathway. When sterols accumulate within cells, the amounts of mRNA produced by both genes are reduced. Conversely, when sterols are depleted, the amounts of mRNA rise, and cholesterol synthesis increases.

Most importantly and surprisingly, it has been found that the discreet SRE elements of the present invention are functionally translocatable to other structural genes. Thus, when the SRE are located upstream of a selected heterologous structural gene, sterol-mediated regulation is conferred to this "hybrid" gene. Therefore, as used herein, the term "functionally translocatable" refers to genetic elements which retain their functional capability in contexts other than their natural state, and the term "hybrid" gene refers to a man-made gene constructed through the application of recombinant DNA techniques to bring together genetic elements not normally associated in nature. Moreover, the term "heterologous structural gene" refers to structural genes other than the LDL receptor gene, and the term "structural gene" refers to any DNA segment which may be both transcribed and translated by a cell.

Accordingly, in a general sense, the invention is directed to a substantially purified segment of DNA comprising a functionally translocatable sterol regulatory element capable of conferring sterol-mediated regulation of structural gene transcription to a selected heterologous structural gene when located upstream from and proximal to a transcription initiation site of such a gene, provided that said segment is free of the structural gene ordinarily under the transcriptional control of said sterol regulatory element, the element including a nucleotide sequence selected from one of the following:

5'-C-A-C-M-S-Y-A-C-3' wherein:
Y = C or T
S = C or G
M = C or A;

or the complement of such a sequence.

In more particular embodiments, this DNA segment will be further defined as including a nucleotide sequence selected from one of the following:

5'-A-T-C-A-C-M-S-Y-A-C-3' wherein:
Y = C or T
S = C or G
M = C or A;

or the complement of such a sequence.

In still further embodiments, the above described general DNA segment will be defined as including within its sequence a nucleotide sequence selected from one of the following:

5'-M-M-M-A-T-C-A-C-M-S-Y-A-C-3' wherein:
Y = C or T
S = C or G
M = C or A;

or the complement of such a sequence.

Moreover, in still further embodiments, the DNA segment of the invention may be defined as including within its sequence a nucleotide sequence selected from one of the following:

5'-M-M-M-A-T-C-A-C-M-S-Y-A-C-K-K-M-3' wherein:
K = T or G
Y = C or T
S = C or G
M = C or A;

or the complement of such a sequence.

Generally, a sequence stretch of on the order of 8 to 50 nucleotides in length, which incorporates one or more of the foregoing sequences, will be preferred for combination with selected structural genes in order to confer sterol-mediated regulation. In fact the inventors have determined that even shorter segments, on the order of 8 to 27 nucleotides in length, may be used for conferring such a sterol-mediated control.

In certain particular embodiments, the invention involves a wide variation of particular DNA sequences which may be incorporated into regions upstream of selected structural genes to bring such structural genes under sterol-mediated control. These sequences may be defined as including within their sequence, a nucleotide sequence selected from one of the following:

(a) 5'-A-G-T-T-T-G-C-A-G-T-G-G-G-G-T-G-A-T-T-T-T-C-A -A-A-T-G-3+;
(b) 5'-A-G-T-T-T-G-C-A-G-T-G-G-G-G-T-G-A-T-T-T-T-C-A -A-A-T-G-3';
(c) 5'-A-G-T-C-T-G-C-A-G-T-G-G-T-G-T-G-A-T-T-T-T-C-A -A-A-A-G-3';
(d) 5'-A-G-T-C-T-G-C-A-G-T-G-G-G-G-T-G-A-T-T-T-T-C-A -A-A-A-A-3';
(e) 5'-G-A-G-A-G-A-T-G-G-T-G-C-G-G-T-G-C-C-T-G-T-T-C -T-T-G-G-3';
(f) 5'-G-A-G-A-G-A-T-G-G-T-G-C-G-G-T-G-C-C-T-G-T-T-C -T-T-G-G-3';
(g) 5'-G-A-G-A-G-A-T-G-G-T-G-C-G-G-T-G-C-C-C-G-T-T-C -T-C-C-G-3';
(h) 5'-G-A-G-A-G-A-T-G-G-T-G-C-G-G-T-G-C-C-C-G-T-T-C -T-C-C-G-3';
(i) 5'-A-C-G-G-T-G-A-C-G-T-A-G-G-T-G-G-C-C-C-G-A-G -A-A-C-A-3'; or
(j) 5'-A-G-T-G-G-G-G-T-G-A-G-A-C-G-G-T -G-A-C-G-3'; or the complement of any of these sequences.

In further aspects, the SRE of the present invention refer to discreet DNA segments represented by the formula:

$(X)_n$ wherein n=1-5, with each X being independently selected from DNA segments having a nucleotide sequence of:

(a) 5'-A-A-A-A-T-C-A-C-C-C-C-A-C-T-G-C-3'; or
(b) 5'-G-C-A-G-T-G-G-G-G-T-G-A-T-T-T-T-3';

with each X unit, if more than one, being from 0–20 nucleotides selected from the group of nucleotides consisting of A, G, C and T.

It has been found by the inventors that the SRE sequences of the present invention confer a sterol-regulatory capability regardless of their orientation with respect to the transcribed strand of DNA. Moreover, it has been found that there is no requirement that this sequence be placed in a particular position with respect to the site of transcription initiation. They thus, act in a fashion similar to enhancer elements in this regard.

It has also surprisingly been determined that the SRE may be introduced into a heterologous gene in multiple copies, either in a forward or reversed orientation, and thereby obtain a much improved sterol regulatory capability. Moreover, multiple SRE units need not be placed in an adjacent conformation and may be separated by numerous random nucleotides and still retain their improved regulatory and promotion capability.

The present invention is also directed to regulatory elements which serve to confer a promotion of transcription initiation without conferring a sterol regulatory capability. As with the SREs, these "positive" promoter sequences are functionally translocatable and may be employed by locating such sequences upstream from and proximal to a transcription site. In a preferred aspect, the transcription promoter sequences are represented by the formula:

$(X)_n$ wherein n=1-5, each X being independently selected from DNA segments having a nucleotide sequence of:

(a) 5'-A-A-A-C-T-C-C-T-C-C-C-C-T-G-C-3';
(b) 5=-G-C-A-G-G-G-G-G-A-G-G-A-G-T-T-T-3';
(c) 5'-A-A-A-C-T-C-C-T-C-C-T-C-T-T-G-C-3'; or
(d) 5'-G-C-A-A-G-A-G-G-A-G-G-A-G-T-T-T-3';

with each X unit, if more than one, being separated by from 0 to 20 nucleotides selected from the group of nucleotides consisting of A, G, C and T.

As noted, the promoter and/or regulatory elements are advantageously employed by locating said sequences upstream from and proximal to a transcription initiation site of a selected heterologous structural gene. Depending on the particular structural gene employed, these control elements may provide some benefit when located up to 300 nucleotides upstream of a transcription initiation site, as measured from the 3, end of the control sequence.

However, in a preferred embodiment, the sequences are located within b 150 nucleotides of transcription initiation.

In a more preferred embodiment, the control sequences are located within 100 nucleotides of an initiation site.

In still more preferred embodiments, the control sequences are located within 50 nucleotides of an initiation site.

Thus, to date, it has been observed that, in general, the closer the control element is to a site of trans-cription initiation, the more effective the resultant control.

It is contemplated that the control sequences will prove useful in the context of a wide array of genes which have been characterized to date. Although, as disclosed in more detail below, it is believed that the sequences will prove useful in the context of virtually any structural gene, it is further believed that these sequences will be of particular benefit in the context of human and related structural genes such as the genes for t-PA (tissue plasminogen activator), human growth hormone, activin, interferon, lymphokines such as interleukins I and II, tumor necrosis factor, and numerous other genes as disclosed herein.

It is an additional object of the present invention to provide control sequences which may be combined with known promoters to provide novel hybrid eukaryotic promoters having sterol regulatory capabilities. Such hybrid promoters may also be employed in the context of selected heterologous structural genes.

It is, therefore, a particular object of the invention to provide a DNA molecule which has incorporated within its structure one or more of the DNA sequences or segments having a sterol regulatory element such as described above, in combination with a structural gene not ordinarily under the transcriptional control of said element, said structural gene and sterol regulatory element being combined in a manner such that said structural gene is under the transcriptional control of said regulatory element.

However, in certain embodiments, the invention will not be limited to use with heterologous structural genes. The present disclosure, thus, additionally provides a method for sterol-mediated regulation of expression of a polypeptide in recombinant cell culture which includes the steps of:

(a) preparing a first DNA segment which includes one or more sterol regulatory elements as described above;

(b) constructing a second DNA segment by positioning said first DNA segment upstream from and proximal to a transcription initiation site of a selected structural gene such that said structural gene may be brought under the transcriptional control of the sterol regulatory element of said first DNA segment;

(c) transforming a host cell with said second DNA segment; and culturing the transformed host cell in the presence of a sterol in amounts and for a time sufficient to suppress transcription of said structural gene.

In important and further embodiments, a method is provided for determining the ability of a candidate substance to activate the transcription of DNA encoding the LDL receptor, which method comprises (a) providing a nucleic acid sequence containing the LDL receptor sterol regulatory element (SRE), a promoter and a reporter gene under the transcriptional control of both of the SRE and the promoter which is capable of conferring a detectable signal on a host cell, (b) transfecting said nucleic acid sequence into a host cell, (c) culturing the cell, (d) contacting the cell culture with the candidate substance, and (e) assaying for the amount of signal produced by the cell culture. The greater the signal the greater the activating character of the candidate. Transcriptionally activating candidate substances are then evaluated further for potential as plasma cholesterol lowering drugs using conventional techniques and animal models.

BRIEF DESCRIPTION OF THE DRAWINGS

FIG. 1 (parts A and B DNA Sequence of the Human LDL Receptor Promoter. The primary structure of a portion of the 5'-flanking region of the receptor gene. Nucleotide +1 is assigned to the A of the ATG translation initiation codon. Transcription initiation sites are indicated by asterisks. Two TATA-like sequences are underlined. Three imperfect direct repeats of 6 bp are overlined with arrows in the promoter sequence and aligned for homology at the bottom of the figure. The synthetic SRE 42 (Table III) differs from the 42-bp sequence shown here by two nt (denoted by dots).

FIG. 4 (parts A and B Sterol-mediated suppression of transfected pLDLR-CAT 1563 and endogenous LDL receptor promoter in CHO cells. A cloned line of CHO cells transfected with pLDLR-CAT 1563 was cultured according to the standard protocol. The cells were incubated for 20 hr with the indicated amounts of cholesterol and 25-hydroxycholesterol (25-OH Chol.), after which total RNA was subjected to primer extension analysis as described in FIG. 3. In Panel A, the $^{32}$P-labeled oligonucleotides were complementary to the mRNA produced by the transfected pLDLR-CAT 1563 gene and the endogenous hamster TK gene. The gel was exposed to X-ray film for 48 hr. In Panel B, the same RNA samples were incubated with three $^{32}$P-oligonucleotide primers complementary to the mRNAs derived from the endogenous hamster TK, LDL receptor, and HMG CoA synthase genes. The black dots represent four mRNA products derived from the LDL receptor gene. The gel was exposed to X-ray film for 48 hr. In Panels A and B, the positions to which radiolabeled markers migrated are indicated on the right.

FIG. 6. Time course of induct in of transfected pLDLR-CAT 1563 gene in CHO cells. A cloned line of CHO cells transfected with pLDLR-CAT 1563 was cultured according to the standard protocol. The cells were incubated for 20 hr with suppression medium containing 10 ug/ml cholesterol and 0.5 ug/ml 25-hydroxycholesterol and then switched to induction medium lacking sterols for the indicated time period. The removal of sterols was staggered in such a way that all cells were harvested at the same time of day 3 of cell growth. Total cellular RNA was isolated and subjected to primer extension analysis with oligonucleotides specific for the transfected CAT gene mRNA and the endogenous hamster TK gene mRNA (Inset). The gel was exposed to X-ray film for 24 hr. For quantitation of "% maximum expression", a ratio of the relative amounts of the LDLR-CAT and TK primer extension products was determined by densitometry. A value of 100% was assigned to the ratio obtained after 48 hr in induction medium.

FIG. 8. Expression and regulation of transfected pLDLR-CAT and pHSVTK-CAT genes in CHO cells. Plasmid pHSVTK-CAT was constructed from plasmids pTK-CAT of Cato et al. (1986), *EMBO J.*, 5:2237) and plasmid 105/115 of McKnight and Kingsbury (1982), Science, 217:316). It contains HSVTK promoter sequences spanning base pairs −108 to +55 and has a BamHI linker inserted at position −108. In the experiment, plasmid pLDLR-CAT 234 or the indicated derivatives containing 10-bp scramble mutations (FIG. 7) were cotransfected with pHSVTK-CAT and pSV3-Neo into CHO cells and assayed for expression and regulation by primer extension. Each pooled cell line (300–600 independent colonies) was set up for assay according to the standard protocol described in Example I. After incubation for 20 hr in the absence (−) or presence (+) of 10 ug/ml cholesterol and 0.5 ug/ml 25-hydroxycholesterol, RNA was prepared and subjected to primer extension analysis using $^{32}$P-labeled oligonucleotides specific for the products of the two transfected CAT genes and for the endogenous hamster TK gene product. The gel was exposed to X-ray film for 48 hr. For quantitation of "% suppression", the relative amounts of the transfected LDLR-CAT (b) and HSVTK-CAT (a) primer extension products were determined by densitometry, and a ratio (b/a) of the two was calculated. The sizes of the primer extension products (right) were determined by comparison to the migration of DNA fragments of known molecular weight electrophoresed in adjacent lanes (not shown).

FIG. 15. Diagram demonstrating the construction of an expression vector for human tissue plasminogen activator (t-PA) using an LDL receptor SRE promoter.

FIG. 16. (parts A and B) Sterol-mediated regulation of chimeric genes containing the LDL receptor promoter upstream regulatory sequences in forward and reverse orientations. The 1507-base pair EcoRl/Alul restriction fragment from the 5' end of the LDL receptor gene used to construct p1471 is shown at the top. Nucleotide positions −1471 to +36 are numbered in relation to the transcription initiation site, indicated by the arrow at +1. A putative TATA box is designated T/A. The two regions that bind Spl in vitro (repeats 1 and 3) are shown, as is the SRE-I within repeat 2. The CAT coding sequence is denoted by the cross-hatched bar. To construct pZ, the region from −33 to −110 of p1471 Was inverted by M13 mutagenesis (Zoller et al. (1984), *DNA*, 3:479-488). Relative transcription was determined by a primer extension assay of the amount of CAT mRNA in stably transfected CHO cells incubated for 24 hr in the absence or presence of sterols. LDL receptor promoter test plasmid expression was normalized to pTK-CAT-1 control plasmid expression in each experiment. The data are expressed as a fraction of the level observed in cells transfected with p1471 and cultured in the absence of sterols in the same experiment. Each value represents the average ±S.E.M. of four experiments. The gel was dried and exposed to X-ray film at −70° C. with an intensifying screen for 75 h. Fold induction was calculated as the ratio of normalized test plasmid expression in the absence of sterols to that in the presence of sterols for each experiment. w.t., wild-type; TK, thymidine kinase; LDLR, LDL receptor.

DETAILED DESCRIPTION OF THE PREFERRED EMBODIMENTS

Figure 2:
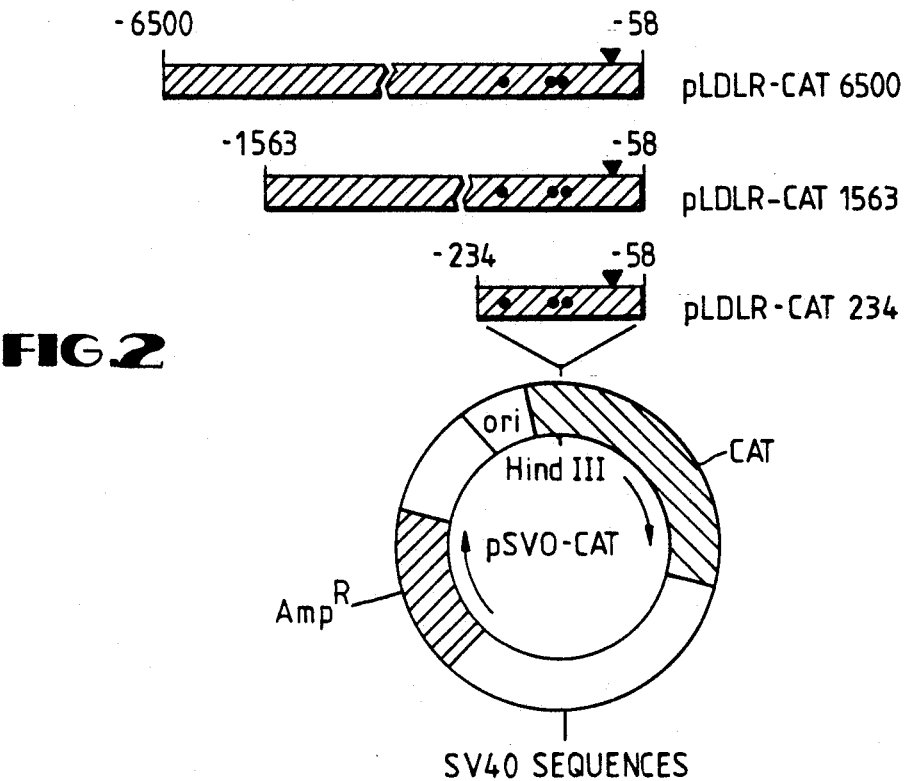
FIG. 2. Structure of human LDL receptor-CAT plasmids. Three fragments of the human LDL receptor promoter with a common 3' end at position -58 were inserted into pSVO-CAT. The arrowhead indicates the region of transcription initiation in the normal human LDL receptor gene (position −93 to −70). Black dots denote three imperfect direct repeats of 16 bp.

Animal cells regulate their cholesterol content through the integration of two pathways that govern the supply of exogenous and endogenous cholesterol. Both pathways are controlled by end-product repression. Preferentially, they obtain cholesterol through the receptor-mediated endocytosis and lysosomal hydrolysis of plasma low density lipoprotein. However, when cells are depleted of cholesterol, they synthesize large amounts of mRNA for the low density lipoprotein (LDL) receptor, which facilitates the uptake of exogenous cholesterol by receptor-mediated endocytosis. The cells also increase their endogenous cholesterol production by increasing the amount of mRNA for two sequential enzymes in de novo cholesterol biosynthesis, 3-hydroxy-3-methylglutaryl coenzyme A (HMG CoA) synthase and HMG CoA reductase. When cholesterol builds up within the cell, all three of these mRNAs are strongly suppressed, an action that limits both the uptake and synthesis of cholesterol.

The present invention embodies the realization that the precise genetic elements which are responsible for this sterol-induced feedback repression of LDL receptor production can be isolated away from the LDL receptor gene and employed to confer sterol regulatory capability to heterologous genes. Moreover, additional control elements contained within the sterol regulatory sequences have been found to confer transcription promotion capability without conferring sterol regulation per se.

The novel nucleic acid sequences of the present invention comprise (1) sequences which provide sterol regulatory capability to heterologous structural genes with or without a positive promotion of transcription (SREs); or (2) sequences which provide a positive promotion of transcription without providing a sterol regulatory capability.

It is now clear that these positive and sterol-mediated control elements reside on separate, but structurally similar, DNA sequences 16 nucleotides in length. Due to their relatively short length, these sequences may be, and have been, routinely synthesized using DNA synthesizers, thus obviating a need for isolation of the sequences from natural sources.

The inventors have discovered and characterized discreet sequence regions which exist upstream of the sterol mediated structural genes. Surprisingly, the minimal sequence requirement, or "core" region, for lo conferring SRE regulation capability has been determined to be localized to an 8 to 10 base pair sequence region. This "core SRE region" acts somewhat like an enhancer element: in the absence of sterols, the SRE serves to simulate transcription rate several fold, whereas in the presence of sterols, it loses this capability.

The present invention contemplates that the basic 8 to 10 nucleotide core SRE region can be employed in connection with any selected heterologous or even homologous structural gene. This basic unit has been characterized from an analysis of upstream control regions of sterol-mediated structural genes. Thus, it will typically be preferred to employ longer sequence stretches that correspond to the identified regions. This is because although the core region is all that is ultimately required, it is believed that particular advantages accrue, in terms of sterol regulation and level of induction achieved in the absence of sterol repression, where one employs sequences which correspond to the natural SRE control regions over longer regions, e.g., up to around 25 or so nucleotides.

These "extended" regions discovered by the inventors to confer sterol-mediated regulation in the case of the sterol-mediated structural genes are as follows:

STEROL-REGULATED PROMOTERS

| | | |
|---|---|---|
| Human<br>Monkey<br>Hamster<br>Rat | LDL<br>Receptor | A G T T T G C A G T G G G G T G A T T T T C A A A T G<br>A G T T T G C A G T G G G G T G A T T T T C A A A T G<br>A G T C T G C A G T G G T G T G A T T T T C A A A A G<br>A G T C T G C A G T G G G G T G A T T T T C A A A A A |
| Human<br>Monkey<br>Hamster<br>Rat | HMG CoA<br>Reductase | G A G A G A T G G T G C G G T G C C T G T T C T T G G<br>G A G A G A T G G T G C G G T G C C T G T T C T T G G<br>G A G A G A T G G T G C G G T G C C C G T T C T C C G<br>G A G A G A T G G T G C G G T G C C C G T T C T C C G |
| Hamster 1<br>Hamster 2 | HMG CoA<br>Synthase | A C G G T G A C G T A G G G T G G C C C G A G A A C A<br>C C G G G G A A G T G G G G T G A G A C G G T G A C G |

```
       1 2 3 4 5 6 7 8
       G T G G G T G
           A C T 10 10 9 6 9 10 10 10
       10 10 1 4 1 10 10 10
```

The inventors have conducted numerous studies to delineate and characterize with some degree of particularity the core SRE region. As noted, these studies have led the inventors to conclude that at least an 8 nucleotide region is required to confer an SRE function. This most basic element can be set forth as follows:

5'C-A-C-M-S-Y-A-C 3';

wherein:

Y=C or T
S=C or G
M=C or A;

or the complement of such a sequence.

However, from the inventors studies, it is contemplated that the incorporation of two additional nucleotides, either G or C, to the 5' end of this 8 nucleotides stretch will provide additional advantages in accordance with the invention. Thus, in these embodiments, the SRE may be defined more particularly as follows:

5'-A-T-C-A-C-M-S-Y-A-C-3' wherein:

Y=C or T
S=C or G
M=C or A;

or the complement of such a sequence.

Also from the inventors studies, it was found that additional nucleotide regions positioned 5' and/or 3' with respect to the central core may provide still further advantages. In these embodiments, the SRE may be defined as follows:

(a) 5'-M-M-M-A-T-C-A-C-M-S-Y-A-C-3'
wherein:
Y=C or T
S=C or G
M=C or A; or (b) 5'-M-M-M-A-T-C-A-C-M-S-Y-A-C-K-K-M-3'
wherein:
K=T or G
Y=C or T
S=C or G
M=C or A; or the complement of such a sequence.

Positive control sequences identified by the inventors, which do not provide an SRE capability, are preferably defined by the sequences:

(a) 5'-A-A-A-C-T-C-C-T-C-C-T-C-T-T-G-C-3';
(b) 5'-A-A-A-C-T-C-C-T-C-C-C-C-T-G-C-3';
(c) 5'-G-C-A-A-G-A-G-G-A-G-G-A-G-T-T-T-3'; and
(d) 5'-G-C-A-G-G-G-G-A-G-G-A-G-T-T-T-3'.

As with the sterol regulatory elements, it will be appreciated that positive promoter segments (c) and (d) represent the opposite strand sequence of promoter segments (a) and (b).

Thus, both a positive and/or a sterol-mediated control is provided by selecting one or more segments from classes of the foregoing control sequences and locating such sequences upstream from and proximal to a heterologous transcription initiation site.

The novel control sequences of the present invention, whether positive, sterol-mediated, or both, may be even more advantageously employed in the form of multiple units, in numerous various combinations and organizations, in forward or reverse orientations, and the like. Moreover, in the context of multiple unit embodiments and/or in embodiments which incorporate both positive and negative control units, there is no requirement that such units be arranged in an adjacent head-to-head or head-to-tail construction in that the improved regulation capability of such multiple units is conferred virtually independent of the location of such multiple sequences with respect to each other. Moreover, there is no requirement that each unit comprise the same positive or negative element. All that is required is that such sequences be located upstream of and sufficiently proximal to a transcription initiation site. However, in a preferred aspect of the improved multiple unit embodiment, the control sequences are located within from 0–20 nucleotides of each other.

When employed in the context of heterologous structural genes, the precise location of the control sequences of the invention with respect to transcription initiation site is not particularly crucial. For example, some benefit will generally be obtained when such control sequences are located up to about 300 nucleotides or more from a transcription initiation site. However, in more preferred embodiments, control sequences are located within 150 nucleotides of such a site. Still more benefit is obtained when the sequences are located within 100 nucleotides of initiation. Moreover, control sequences are most advantageously employed when disposed within 50 nucleotides of transcription initiation. Thus, in general, the closer the control sequences are to transcription initiation, the more pronounced and effective the control obtained.

Therefore, to employ the foregoing regulatory elements in the context of heterologous genes, one simply obtains the structural gene and locates one or more of such control sequences upstream of a transcription initiation site. Additionally, as is known in the art, it is generally desirable to include TATA-box sequences upstream of and proximal to a transcription initiation site of the heterologous structural gene. Such sequences may be synthesized and inserted in the same manner as the novel control sequences. Alternatively, one may desire to simply employ the TATA sequences normally associated with the heterologous gene. In any event, TATA sequences are most desirably located between about 20 and 30 nucleotides upstream of transcription initiation.

Numerous methods are known in the art for precisely locating selected sequences at selected points within larger sequences. Most conveniently, the desired control sequence or sequences, or combinations of sequences, are synthesized and restriction site linker fragments added to the control sequence termini. This allows for ready insertion of control sequences into compatible restriction sites within upstream regions. Alternatively, synthesized control sequences may be ligated directly to selected regions. Moreover, site specific mutagenesis may be employed to fashion restriction sites into which control sequences may be inserted in the case where no convenient restriction sites are found at a desired insertion site.

As noted, it is believed that the control sequences of the present invention may be beneficially employed in the context of any heterologous structural gene, with or without additional homologous or heterologous control or promotion sequences. The following table, Table I, lists a number of known defined structural genes, along with descriptive references, which may be employed in the context of the control sequences of the present invention. It should, however, be appreciated that this table is in no way intended to be an exhaustive or all-inclusive listing, and it is included herein for the convenience of the reader. For a more extensive listing, one may wish to refer to Beaudet (1985), *Am. J. Hum. Gen.*, 37:386–406.

TABLE I

| Gene | Selected Cloned Structural Genes | |
|---|---|---|
| | Clone Type* | Reference |
| activin | porcine-cDNA | Mason AJ, Nat, 318:659, 1985 |
| adenosine deaminase | h-cDNA | Wiginton DA, PNAS, 80:7481, 1983 |
| angiotensinogen I | r-cDNA | Ohkubo H, PNAS, 80:2196, 1983 |
| | r-gDNA | Tanaka T, JBC, 259:8063, 1984 |
| antithrombin III | h-cDNA | Bock SC, NAR 10:8113, 1982 |
| | h-cDNA and gDNA | Prochownik EV, JBC, 258:8389, 1983 |
| antitrypsin, alpha I | h-cDNA | Kurachi K, PNAS, 78:6826, 1981 |
| | h-gDNA | Leicht M, Nat, 297:655, 1982 |
| | RFLP | Cox DW, AJHG, 36:134S, 1984 |
| apolipoprotein A-I | h-cDNA, h-gDNA | Shoulders CC, NAR, 10:4873, 1982 |
| | RFLP | Karathanasis SK, Nat, 301:718, 1983 |
| | h-gDNA | Kranthanasis SK, PNAS, 80:6147, 1983 |
| apolipoprotein A-II | h-cDNA | Sharpe CR, NAR, 12:3917, 1984 |
| | Chr | Sakaguchi AY, AJHG, 36:207S, 1984 |
| | h-cDNA | Knott TJ, BBRC, 120:734, 1984 |
| apolipoprotein C-1 | h-cDNA | Knott TJ, NAR, 12:3909, 1984 |
| apolipoprotein C-II | h-cDNA | Jackson CL, PNAS, 81:2945, 1984 |
| | h-cDNA | Mykelbost O, JBC, 259:4401, 1984 |
| | h-cDNA | Fojo SS, PNAS, 81:6354, 1984 |
| | RFLP | Humphries SE, C Gen, 26:389, 1984 |
| apolipoprotein C-III | h-cDNA and gDNA | Karantanasis SK, Nat, 304:371, 1983 |
| | h-cDNA | Sharpe CR, NAR, 12:3917, 1984 |
| apolipoprotein E | h-cDNA | Breslow JL, JBC, 257:14639, 1982 |
| atrial natriuretic factor | h-cDNA | Oikawa S, Nat, 309:724, 1984 |
| | h-cDNA | Nakayama K, Nat, 310:699, 1984 |
| | h-cDNA | Zivin RA, PNAS, 81:6325, 1984 |
| | h-gDNA | Seidman CE, Sci, 226:1206, 194 |
| | h-gDNA | Nemer M, Nat, 312:654, 1984 |

TABLE I-continued
Selected Cloned Structural Genes

| Gene | Clone Type* | Reference |
|---|---|---|
| | h-gDNA | Greenberg BI, Nat, 312:656, 1984 |
| chorionic gonadotropin, alpha chain | h-cDNA | Fiddes JC, Nat, 281:351, 1981 |
| | RFLP | Boethby M, JBC, 256:5121, 1981 |
| chorionic gonadotropin, beta chain | h-cDNA | Fiddes JC, Nat, 286:684, 1980 |
| | h-gDNA | Boorstein WR, Nat, 300:419, 1982 |
| | h-gDNA | Talmadge K, Nat, 307,37, 1984 |
| chymosin, pro (rennin) | bovine-cDNA | Harris TJR, NAR, 10:2177, 1982 |
| complement, factor B | h-cDNA | Woods DE, PNAS, 79:5661, 1982 |
| | h-cDNA and gDNA | Duncan R, PNAS, 80:4464, 1983 |
| complement C2 | h-cDNA | Bentley DR, PNAS, 81:1212, 1984 |
| | h-gDNA (C2, C4, and B) | Carroll MC, Nat, 307:237, 1984 |
| complement C3 | m-cDNA | Domdey H, PNAS, 79:7619, 1983 |
| | h-gDNA | Whitehead AS, PNAS, 79:5021, 1982 |
| complement C4 | h-cDNA and gDNA | Carroll MC, PNAS, 80:264, 1983 |
| | h-cDNA | Whitehead AS, PNAS, 80:5387, 1983 |
| complement C9 | h-cDNA | DiScipio RC, PNAS, 81:7298, 1984 |
| corticotropin releasing factor | sheep-cDNA | Furutani Y, Nat, 301:537, 1983 |
| | h-gDNA | Shibahara S, EMBO J, 2:775, 1983 |
| epidermal growth factor | m-cDNA | Gray A, Nat, 303:722, 1983 |
| | m-cDNA | Scott J, Sci, 221:236, 1983 |
| | h-gDNA | Brissenden JE, Nat, 310:781, 1984 |
| epidermal growth factor receptor, oncogene c-erb B | h-cDNA and Chr | Lan CR, Sci, 224:843, 1984 |
| epoxide dehydratase | r-cDNA | Gonzalez FJ, JBC, 256:4697, 1981 |
| erythropoietin | h-cDNA | Lee-Huang S, PNAS, 81:2708, 1984 |
| esterase inhibitor, Cl | h-cDNA, | Stanley KK, EMBO J, 3:1429, 1984 |
| factor VIII | h-cDNA and gDNA | Gitschier J, Nat, 312:326, 1984 |
| | h-cDNA | Toole JJ, Nat, 312:342, 1984 |
| factor IX, Christmas factor | h-cDNA | Kutachi K, PNAS, 79:6461, 1982 |
| | h-cDNA | Choo KH, Nat, 299:178, 1982 |
| | RFLP | Camerino G, PNAS, 81:498, 1984 |
| | h-gDNA | Anson DS, EMBO J, 3:1053, 1984 |
| factor X | h-cDNA | Leytus SP, PNAS, 81:3699, 1984 |
| fibrinogen A alpha, B beta, gamma | h-cDNA | Kant JA, PNAS, 80:3953, 1983 |
| | h-gDNA (gamma) | Fornace AJ, Sci, 224:161, 1984 |
| | h-cDNA (alpha gamma) | Imam AMA, NAR, 11:7427, 1983 |
| | h-gDNA (gamma) | Fornace AJ, JBC, 259:12826, 1984 |
| gatrin releasing peptide | h-cDNA | Spindel ER, PNAS, 81:5699, 1984 |
| glucagon, prepro | hamster-cDNA | Bell GI, Nat, 302:716, 1983 |
| | h-gDNA | Bell GI, Nat, 304,368, 1983 |
| growth hormone | h-cDNA | Martial JA, Sci, 205:602, 1979 |
| | h-gDNA | DeNoto FM, NAR, 9:3719, 1981 |
| | GH-like gene | Owerbach D, Sci, 209:289, 1980 |
| growth hormone RF, somatocrinin | h-cDNA | Gubler V, PNAS, 80:4311, 1983 |
| | h-cDNA | Mayo KE, Nat, 306:86, 1983 |
| hemopexin | h-cDNA | Stanley KK, EMBO J, 3:1429, 1984 |
| inhibin | porcine-cDNA | Mason AJ, Nat, 318:659, 1985 |
| insulin, prepro | h-gDNA | Ullrich A, Sci, 209:612, 1980 |
| insulin-like growth factor I | h-cDNA | Jansen M, Nat, 306:609, 1983 |
| | h-cDNA | Bell GI, Nat, 310:775, 1984 |
| | Chr | Brissenden JE, Nat, 310:781, 1984 |
| insulin-like growth factor II | h-cDNA | Bell GI, Nat, 310:775, 1984 |
| | h-gDNA | Dull TJ, Nat, 310:777, 1984 |
| | Chr | Brissenden JE, Nat, 310:781, 1984 |
| interferon, alpha (leukocyte), multiple | h-cDNA | Maeda S, PNAS, 77:7010, 1980 |
| | h-cDNA (8 distinct) | Goeddel DV, Nat, 290:20, 1981 |
| | h-gDNA | Lawn RM, PNAS, 78:5435, 1981 |
| | h-gDNA | Todokoro K, EMBO J, 3:1809, 1984 |
| | h-gDNA | Torczynski RM, PNAS, 81:6451, 1984 |
| interferon, beta (fibroblast) | h-cDNA | Taniguchi T, Gene, 10:11, 1980 |
| | h-gDNA | Lawn RM, NAR, 9:1045, 1981 |
| | h-gDNA (related) | Sehgal PB, PNAS, 80:3632, 1983 |
| | h-gDNA (related) | Sagar AD, Sci, 223:1312, 1984 |
| interferon, gamma (immune) | h-cDNA | Gray PW, Nat, 295:503, 1982 |
| | h-gDNA | Gray PW, Nat, 298:859, 1982 |
| interleukin-1 | m-cDNA | Lomedico PT, Nat, 312:458, 1984 |
| interleukin-2, T-cell growth factor | h-cDNA | Devos R, NAR, 11:4307, 1983 |
| | h-cDNA | Taniguchi T, Nat, 302:305, 1983 |
| | h-gDNA | Hollbrook NJ, PNAS, 81:1634, 1984 |
| | Chr | Siegel LJ, Sci, 223:175, 1984 |
| interleukin-3 | m-cDNA | Fung MC, Nat, 307:233, 1984 |
| kininogen, two forms | bovine-cDNA | Nawa H, PNAS, 80:90, 1983 |
| | bovine-cDNA and gDNA | Kitamura N, Nat, 305:545, 1983 |
| luteinizing hormone, beta subunit | h-gDNA and Chr | Talmadge K, Nat, 207:37, 1984 |
| luteinizing hormone releasing hormone | h-cDNA and gDNA | Seeburg PH, Nat, 311:666, 1984 |
| lymphotoxin | h-cDNA and gDNA | Gray PW, Nat, 312:721, 1984 |
| mast cell growth factor | m-cDNA | Yokoya T, PNAS, 81:1070, 1984 |

TABLE I-continued

| Gene | Selected Cloned Structural Genes | |
|---|---|---|
| | Clone Type* | Reference |
| nerve growth factor, beta subunit | m-cDNA | Scott J, Nat, 302:538, 1983 |
| | h-gDNA | Ullrich A, Nat, 303:821, 1983 |
| | Chr | Franke C, Sci, 222:1248, 1983 |
| oncogene, c-sis, PGDF chain A | h-gDNA | Dalla-Favera R, Nat, 295:31, 1981 |
| | h-cDNA | Clarke MF, Nat, 208:464, 1984 |
| pancreatic polypeptide and icosapeptide | h-cDNA | Boel E, EMBO J, 3:909, 1984 |
| parathyroid hormone, prepro | h-cDNA | Hendy GN, PNAS, 78:7365, 1981 |
| | h-gDNA | Vasicek TJ, PNAS, 80:2127, 1983 |
| plasminogen | h-cDNA and gDNA | Malinowski DP, Fed P, 42:1761, 1983 |
| plasminogen activator | h-cDNA | Edlund T, PNAS, 80:349, 1983 |
| | h-cDNA | Pennica D, Nat, 301:214, 1983 |
| | h-gDNA | Ny T, PNAS, 81:5355, 1984 |
| prolactin | h-cDNA | Cook NE, JBC, 256:4007, 1981 |
| | r-gDNA | Cooke NE, Nat, 297:603, 1982 |
| proopiomelanocortin | h-cDNA | DeBold CR, Sci, 220:721, 1983 |
| | h-gDNA | Cochet M, Nat, 297:335, 1982 |
| protein C | h-cDNA | Foster D, PNAS, 81:4766, 1984 |
| prothrombin | bovine-cDNA | MacGillivray RTA, PNAS, 77:5153, 1980 |
| relaxin | h-gDNA | Hudson P, Nat, 301:628, 1983 |
| | h-cDNA (2 genes) | Hudson P, EMBO J, 3:2333, 1984 |
| | Chr | Crawford RJ, EMBO J, 3:2341, 1984 |
| renin, prepro | h-cDNA | Imai T, PNAS, 80:7405, 1983 |
| | h-gdNA | Hobart PM, PNAS 81:5026, 1984 |
| | h-gDNA | Miyazaki H, PNAS, 81:5999, 1984 |
| | Chr | Chirgwin JM, SCMG, 10:415, 1984 |
| somatostatin | h-cDNA | Shen IP, PNAS 79:4575, 1982 |
| | h-gdNA and Ri-IP | Naylot Sl, PNAS, 80:2686, 1983 |
| tachykinin, prepro, | bovine-cDNA | Nawa H, Nat, 306:32, 1983 |
| substances P & K | bovine-gDNA | Nawa H, Nat, 312:729, 1984 |
| urokinase | h-cDNA | Verde P, PNAS, 81:4727, 1984 |
| vasoactive intestinal peptide, prepro | h-cDNA | Itoh N, Nat, 304:547, 1983 |
| vasopressin | r-cDNA | Schmale H, EMBO J, 2:763, 1983 |

*cDNA ... complementary DNA
Chr ... chromosome
gDNA ... genomic DNA
RFLP ... restriction fragment polymorphism
h-human
m-mouse
r-rat With respect to the novel LDL receptor-stimulating drug screening method, the method as provided herein preferably employs a reporter gene that confers on its recombinant hosts a readily detectable phenotype that emerges only under the control of the LDL receptor SRE. Generally reporter genes encode a polypeptide not otherwise produced by the host cell which is detectable by in situ analysis of the cell culture, e.g., by the direct fluorometric, radioisotopic or spectrophotometric analysis of the cell culture without the need to remove the cells for signal analysis from the culture chamber in which they are contained. Preferably the gene encodes an enzyme which produces colorimetric or fluorometric change in the host cell which is detectable by in situ analysis and which is a quantitative or semi-quantitative function of transcriptional activation. Exemplary enzymes include esterases, phosphatases, proteases (tissue plasminogen activator or urokinase) and other enzymes capable of being detected by activity which generates a chromophore or fluorophore as will be known to those skilled in the art.

A preferred example is E. coli beta-galactosidase. This enzyme produces a color change upon cleavage of the indigogenic substrate indolyl-B-D-galactoside by cells bearing beta-galactosidase (see, e.g., Goring et al., Science, 235:456–458 1987) and Price et al., Proc. Natl. Acad. Sci. USA, 84:156–160 (1987)). Thus, this enzyme facilitates automatic plate reader analysis of SRE-mediated expression directly in microtiter wells containing transformants treated with candidate activators. Also, since the endogenous beta-galactosidase activity in mammalian cells ordinarily is quite low, the analytic screening system using B-galactosidase is not hampered by host cell background.

Another class of reporter genes which confer detectable characteristics on a host cell are those which encode polypeptides, generally enzymes, which render their transformants resistant against toxins, e.g., the neo gene which protects host cells against toxic levels of the antibiotic G418; a gene encoding dihydrofolate reductase, which confers resistance to methotrexate, or the chloramphenicol acetyltransferase (CAT) gene (Osborne et al., Cell, 42:203–212 (1985)). Genes of this class are not preferred since the phenotype (resistance) does not provide a convenient or rapid quantitative output. Resistance to antibiotic or toxin requires days of culture to confirm, or complex assay procedures if other than a biological determination is to be made.

Other genes for use in the screening assay herein are those capable of transforming hosts to express unique cell surface antigens, e.g., viral env proteins such as HIV gp120 or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstances the signal is modified in order to remove sequences that interdict secretion. For example, the herpes gD coat protein has been modified by site directed deletion of its transmembrane binding domain, thereby facilitating its secretion (EP 139,417A). This truncated form of the herpes gD protein is detectable in the culture medium by conventional immunoassays. Preferably, however, the products of the reporter gene are lodged in the intracellular or membrane compartments. Then they can be fixed to the culture container, e.g. microtiter wells, in which they are grown, followed by addition of a detectable signal generating substance such as a chromogenic substrate for reporter enzymes.

In general, an SRE is employed to control transcription and hence influence expression of the reporter gene. The process which in its entirety leads to enhanced transcriptional promotion is termed "activation". The mechanism by which a successful candidate is acting is not material in any case since the objective is to upregulate the LDL receptor by whatever means will function to do so. While use of the entire LDL receptor promoter, including the SRE, will most closely model the therapeutic target, the SRE is optionally combined with more potent promoters, e.g., the TK or SV40 early promoter described in the Examples infra in order to increase the sensitivity of the screening assay.

The SRE-containing promoter, whether a hybrid or the native LDL receptor promoter, is ligated to DNA encoding the reporter gene by conventional methods. The SRE is obtained by in vitro synthesis or recovered from genomic DNA. It is ligated upstream of the start codon of the reporter gene. The SRE-containing promoter also will contain an AT-rich region (TATA box) located between the SRE and the reporter gene start codon. The region 3' to the coding sequence for the reporter gene will contain a transcription termination and polyadenylation site, for example the hepatitis B polyA site. The promoter and reporter gene are inserted into a replicable vector and transfected into a cloning host such as E. coli, the host cultured and the replicated vector recovered in order to prepare sufficient quantities of the construction for later transfection into a suitable eukaryotic host.

The host cells used in the screening assay herein generally are mammalian cells, and preferably are permanent cell lines. Cell lines should be stable and relatively easy to grow in large scale culture. Also, they should contain as little native background as possible considering the nature of the reporter polypeptide. Examples include the Hep G2, VERO, HeLa, CHO, W138, BHK, COS-7, and MDCK cell lines. The SRE-containing containing vector is cotransfected into the desired host, stable transformants selected and, optionally, the reporter gene and its controlling SRE-containing promoter are amplified in order to increase the screening assay sensitivity. This is accomplished in conventional fashion by cotransforming the host with the reporter gene and a selectable marker gene such as DHFR (for DHFR minus host cells such as CHO) or DHFR and neo for other hosts, followed by the application of a selection agent.

The screening assay typically is conducted by growing the SRE transformants to confluency in microtiter wells, adding serial molar proportions of cholesterol and/or other sterols that suppress the SRE, and candidate to a series of wells, and the signal level determined after an incubation period that is sufficient to demonstrate sterol-mediated repression of signal expression in controls incubated solely with 10 micrograms cholesterol/ml and 0.5 micrograms 25-hydroxycholesterol/ml. The wells containing varying proportions of candidate are then evaluated for signal activation. Candidates that demonstrate dose related enhancement of reporter gene transcription or expression are then selected for further evaluation as clinical therapeutic agents. The stimulation of transcription may be observed in the absence of added sterols, in which case the candidate compound might be a positive stimulation of the SRE. Alternatively, the candidate compound might only give a stimulation in the presence of sterols, which would indicate that it functions to oppose the sterol-mediated suppression of the SRE. Candidate compounds of either class might be useful therapeutic agents that would stimulate production of LDL receptors and thereby lower blood cholesterol in patients.

It should be understood that the screening method herein is useful notwithstanding that effective candidates may not be found, since it would be a practical utility to know that SRE activators do not exist. The invention consists of providing a method for screening for such candidates, not in finding them. While initial candidate agents might be sterol derivatives, at this time it is unknown which sterol derivatives, if any, will be efficacious.

EXAMPLE I

Expression and Regulation of Human LDL Receptor Promoter-CAT Genes

From a consideration of the nucleotide sequence of the 5' region of the human LDL receptor gene (see FIG. 1) three 16 base sequences were observed whose sequences appeared to be at least partially conserved with respect to each other. It was initially hypothesized by the present inventors that these sequences, alone or in combination with each other or in association with flanking sequences may function to provide sterol regulation to the LDL receptor gene.

Various different experimental approaches have been employed by the present inventors to demonstrate that these 5'-flanking sequences contain transcription signals that confer both positive and negative regulation. In one approach, hybrid genes have been constructed from LDL receptor 5'-flanking sequences and those of the herpes simplex virus thymidine kinase (HSV TK) gene (see Example II). These studies showed that the two more proximal direct repeats (repeats 2 and 3) harbored a regulatory sequence that responded in a negative manner to the level of sterols in the culture medium. This sequence is referred to by the present inventors as the Sterol Regulatory Element (SRE) of the LDL receptor gene.

The present example reflects experiments conducted to display generally the positive regulatory capability of the 5' regions. In this regard, fusion genes constructed between a marker gene and up to 6500 bp of 5'-flanking DNA of the LDL receptor gene identified a 177-bp fragment of the receptor gene that contained signals for both positive expression and negative regulation by sterols. The sequences responsible for positive expression were further delineated by analyzing a series of 15 mutations in the 177-bp promoter fragment, in which overlapping 10-bp segments were scrambled by site-directed mutagenesis. The results of these studies indicate that each of the three direct repeats as well as one of the TATA sequences in the receptor promoter are preferred for LDL receptor mRNA expression. Comparison of the direct repeat sequences with a newly derived consensus sequence recognized by the eukaryotic transcription factor Sp1 reveals a sufficient degree of homology to suggest to the present inventors that this protein may play a role in the expression of the LDL receptor gene.

For the experiments which follow, a series of three plasmids were constructed in which 5'-flanking sequences of the LDL receptor gene were fused to the bacterial CAT gene (chloramphericol acetyl transferase) (see FIG. 2). E. coli cells harboring plasmid pLDL-CAT 234 have been deposited with the ATCC on Mar. 30, 1987, and accorded ATCC designation 67375.

Abbreviations used bp, base pairs; CAT, chloroamphenicol acetyltransferase; CHO, Chinese hamster ovary; HMG CoA, 3-hydroxy-3-methylglutaryl CoA; HSVTK, herpes simplex virus thymidine kinase; kb, kilobase(s); LDL, low density lipoprotein; nt, nucleotide; SRE, sterol regulatory element; TE buffer, 10 mM Tris-chloride and 1 mM EDTA at pH 8; TK, thymidine kinase.

SELECTED MATERIALS AND METHODS EMPLOYED

Materials

[gamma-$^{32}$P]ATP (>5000 Ci/mmole) was obtained from ICN. Enzymes used in plasmid constructions were obtained from New England Biolabs and Boehringer Mannheim Biochemicals. Reverse transcriptase was purchased from Life Sciences (Cat. No. AMV 007). G418 sulfate (Geneticin) was purchased from GIBCO Laboratories. Plasmid pSV3-Neo, which contains a bacterial gene that confers resistance to G418 (Southern et al. (1982), *J. Mol. Appl. Gen.*, 1:327), was obtained from Bethesda Research Laboratories. Cholesterol and 25-hydroxycholesterol were purchased from Alltech Associates and Steraloids, Inc., respectively. Plasmid pSVO-CAT (Gorman et al. (1982), *Moll Cell. Biol.*, 2:1044) was kindly provided by Dr. Bruce Howard. Newborn calf lipoprotein-deficient serum (d>215 g/ml) was prepared by ultracentrifugation (Goldstein et al. (1983), *Meth. Enzymol.*, 98:241). Oligonucleotides were synthesized on an Applied Biosystems Model 380A DNA synthesizer.

Plasmid Constructions

1) LDL Receptor Promoter-CAT Genes. A series of plasmids was constructed by standard techniques of genetic engineering (Maniatis et al. (1982), *Molecular Cloning: A Laboratory Manual*, Cold spring Harbor Laboratory, Press, N.Y., pp 1–545). These plasmids contained fragments of the LDL receptor promoter extending for various distances in the 5' direction and terminating at position −58 linked to the bacterial gene encoding chloramphenicol acetyl transferase (CAT). The LDL receptor fragments were inserted into the unique HindIII site of pSVO-CAT, a recombinant plasmid that contains the beta-lactamase gene, the origin of replication from pBR322, and the coding sequence for CAT (Gorman et al., supra). All of the cloning junctions in the resulting series of LDL receptor-CAT genes were verified by DNA sequence analysis and restriction endonuclease mapping.

Figure 7A:
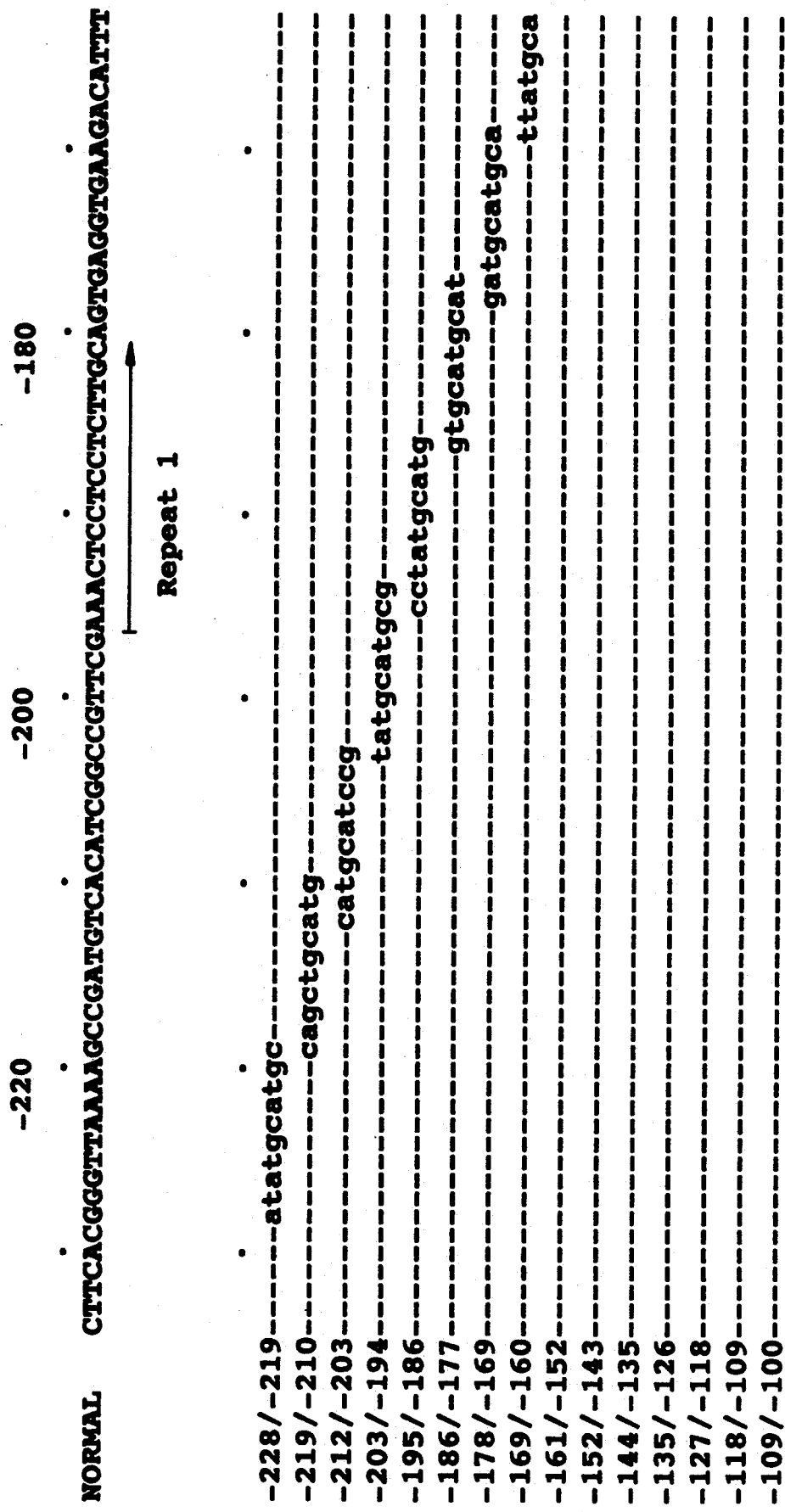
FIG. 7 (parts A and B Nucleotide sequences of normal and mutant LDL receptor promoters. The sequence of a portion of the normal LDL receptor promoter is shown at the top and numbered according to a convention in which the A of the ATG initiation codon is +1. Dots are placed above the sequence every 10 nt beginning at −80. Transcription initiation sites are indicated by asterisks, and two TATA-like sequences are underlined. Three imperfect direct repeats of 16 nt are indicated by the arrows beneath the sequence. Below the sequence of the normal promoter are shown 15 overlapping mutations that were separately introduced into the DNA by site-directed oligonucleotide mutagenesis. The mutations are labeled on the left according to the 10-bp sequence that was scrambled. The novel sequence that was introduced is shown in lower case letters below the normal promoter sequence. Dashes indicate nucleotides that are identical between the normal and mutant promoters.
Figure 7B:
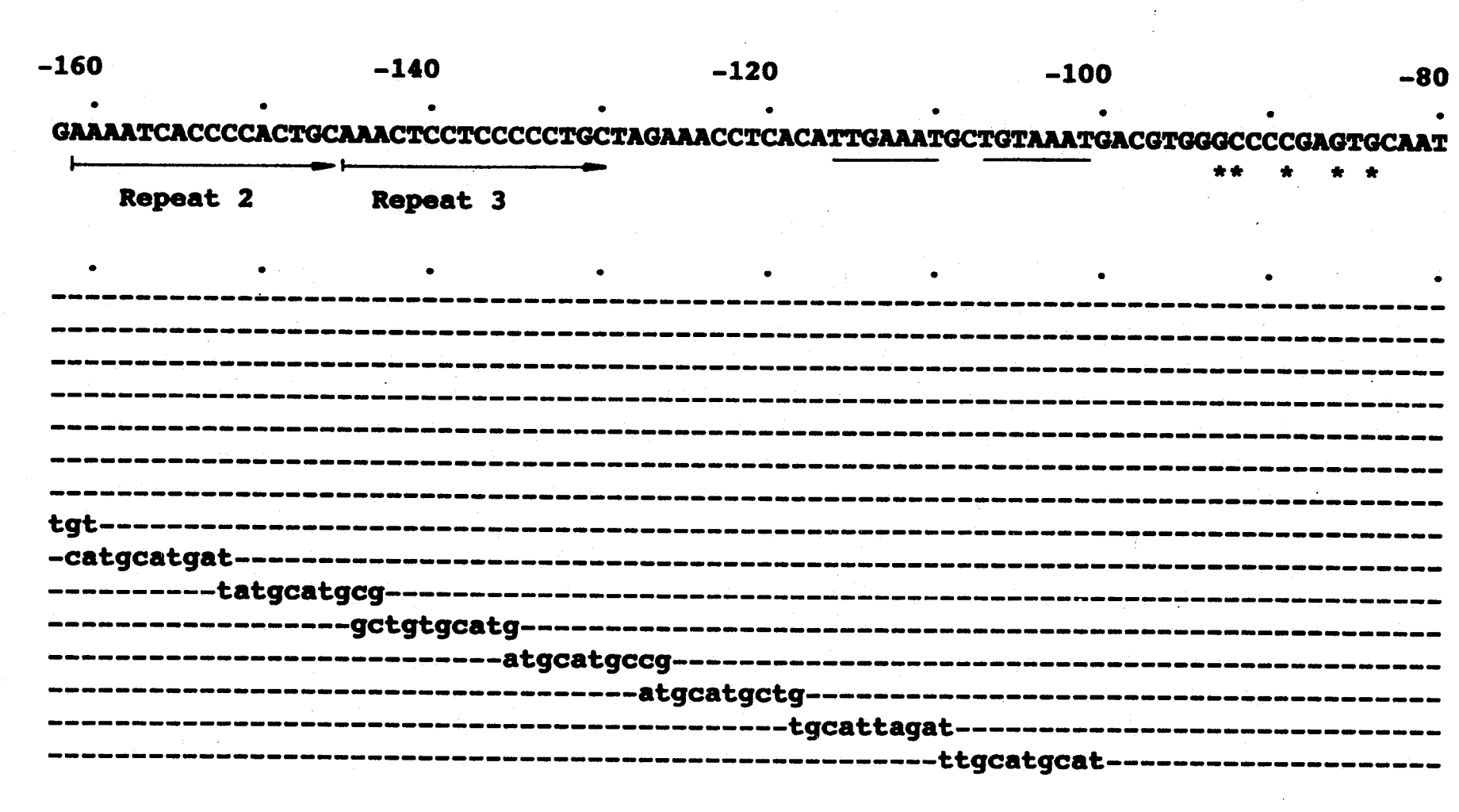

2) Scramble Mutations in LDL Receptor Promoter-Cat Genes. To construct the series of 15 promoter mutations diagramed in FIG. 7, a 1.8-kilobase (kb) EcoRI-PstI fragment containing the LDL receptor promoter was excised from plasmid pLDLR-CAT 234 and cloned into the bacteriophage M13 mp19 vector (Messing (1983), *Meth. Enzymol.*, 101:20). Site specific mutagenesis was performed on single stranded M13 recombinant DNA using the single primer method of Zoller and Smith (Zoller et al. (1984), *DNA*, 3:47a). Mutagenic oligonucleotides of 40–42 bases in length were employed in which the 10 base sequence to be scrambled was located in the center of the oligonucleotide. To facilitate unambiguous identification of a given mutant, each of the introduced 10 base sequences contained a novel NsiI and/or SphI site. After annealing and extension with the large fragment of DNA polymerase I in the presence of bacteriophage T4 DNA ligase, the double-stranded M13 DNA was transformed into *E. coli* TG1 cells. Plaques containing the desired mutation were identified by hybridization with the radiolabeled mutagenic oligonucleotide, subjected to one round of plaque purification, and then sequenced by the methods of Sanger, et al. (1980), *J. Mol. Biol.*, 143:161). The EcoRI-PstI fragment containing the mutation was excised from the M13 clone after conversion of the single stranded DNA into double stranded DNA by primer extension (Maniatis et al., supra) and then recloned into the pSVO-CAT backbone. The resulting plasmid was characterized by restriction mapping with NsiI or SphI and DNA sequencing and then assigned a name according to the 10-bp sequence scrambled; e.g., pLDLR-CAT −228/−219 harbors an LDL receptor promoter fragment extending from −234 to −58 (FIG. 2) in which the normal 10-bp sequence between −228 and −219 (GGGTTAAAAG) has been replaced with ATATGCATGC (FIG. 7).

DNA Transfection and G418 Selection

All cells were grown in monolayer culture at 37~C in an atmosphere of 5%–7% Co$_2$. CHO-K1 cells were maintained in medium A (Ham's F12 medium containing 17 mM N-2-hydroxyethylpiperazine-N'-2-ethanesulfonic acid at pH 7.4, 21 mM glutamine, 100 U/ml penicillin, and 100 ug/ml streptomycin) supplemented with 10% (v/v) fetal calf serum. Cells were seeded at 5×10$^5$ per 100-mm dish in medium B (Dulbecco's modified Eagle medium containing 17 mM N-2-hydroxyethylpiperazine-N'-2-ethanesulfonic acid at pH 7.4, 3 ug/ml proline, 100 U/ml penicillin, and 100 ug/ml streptomycin) supplemented with 10% fetal calf serum. On the following day, the cells were transfected by the calcium phosphate coprecipitation technique (van de Eb et al. (1980), *Meth. Enzymol.*, 65:826) with one or two test plasmids (7.5 ug of pLDLR-CAT with or without 2.5 ug pHSVTK-CAT) together with 0.5 ug pSV3-Neo. The cells were incubated with the DNA for 5 hr and then exposed to 20% (v/v) glycerol in medium B for 4 mind. Thereafter the cells were incubated in medium B supplemented with 10% fetal calf serum for 24 hr and then switched to the same medium containing 700 ug/ml G418. Selection with G418 was maintained until stable resistant colonies could be discerned (2–3 weeks). Resistant colonies Were pooled (150–600 per transfection), expanded in mass cultures in the presence of G418 (700 ug/ml), and used for experiments. In the experiments described in FIG. 4–6, a single-cell derived subclone was obtained by limiting dilution from a pooled cell line derived after transfection with pLDLR-CAT 1563, expanded in mass culture, and screened for CAT enzyme activity (Gorman et al., supra). A subclone expressing the highest level of CAT enzyme activity was then examined for regulatory activity using a primer extension assay for mRNA levels (see below).

Sterol-Regulation Experiments

Pooled or cloned cell lines were seeded at $2 \times 10^5$ cells per 100-mm dish on day 0 in medium A supplemented with 10% fetal calf serum. In the standard protocol, on day 2 the cells were washed with 5 ml phosphate-buffered saline and fed with 8 ml of medium A containing 10% calf lipoprotein-deficient serum in place of whole fetal calf serum. This medium contained either no additions (induction medium) or a mixture of cholesterol and 25-hydroxycholesterol in a ratio of 20:1 added in 4 to 26 ul ethanol (suppression medium). On day 3 after incubation for 20 hr in induction or suppression medium, the cells from 12 dishes were harvested in 4M guanidinium thiocyanate containing 6.25 g/l lauroyl sarcosine, 9.25 g/l sodium citrate, and 0.7% (v/v) B-mercaptoethanol, and the total RNA was purified by centrifugation through CsCl. The RNA pellet was dissolved in buffer containing 10 mM Tris-chloride and 1 mM EDTA at pH 8.0 (TE buffer), precipitated with ethanol, and then quantitated by $OD^{260}$. Approximately 20-40 ug of total RNA were obtained from each 100-mm dish of cells.

Primer Extension Assays

To detect transcripts containing CAT sequences, (derived from pLDLR-CAT and/or pHSVTK-CAT), we used an mRNA-complementary primer of 40 nt corresponding to bases 400 to 439 of the published CAT gene sequence (Alton et al. (1979), *Nature*, 282:864). Transcripts from the neo gene (conferring G418 resistance) were detected with an mRNA-complementary primer of 37 nt corresponding to bases 1407 to 1443 of the transposon Tn5 gene sequence (Beck et al. (1982), *Gene*, 19:327). Endogenous hamster TK mRNA was detected with a 43-nt long primer derived from bases 198 to 240 of the cDNA sequence (Lewis (1986), *Mol. Cell. Biol.*, 6:1998). Endogenous hamster HMG CoA synthase mRNA was measured by extension with a 40-nt long primer corresponding to bases 41 to 80 of the cDNA sequence (Gil et al. (1986), *J. Biol. Chem.*, 261:3710). Endogenous hamster LDL receptor mRNA was detected with an oligonucleotide primer of 36 nt whose sequence was derived from exon 4 of the hamster gene.

Each oligonucleotide was 5' end-labeled to a specific activity of >5000 Ci/mmol with [gamma-$^{32}$P]ATP and T4 polynucleotide kinase. Primers for the neo gene and the endogenous TK gene were diluted with an appropriate amount of unlabeled oligonucleotide to obtain a signal that approximately equal in intensity to that from the test plasmid. The labeled primers (1-2 ul of a $5-10\times 10^{-4}$ $OD_{260}$ units/ml solution) were coprecipitated with 20 ug of total RNA in ethanol and resuspended in 10 ul of TE buffer and 0.27M KCl for hybridization. Hybridization was carried out for 15 min at 68~C, after which the samples were centrifuged for 5 sec at 4~C. A solution (24 ul) containing 17 U reverse transcriptase (Life Sciences, St. Petersburg, Fla.), 20 mM Tris-chloride (pH 8.7), 10 mM MgCl$_2$, 10 mM dithiothreitol, 0.4 mM dNTPs, and 0.25 ug/ml actinomycin D was added to each tube. The samples were incubated 1 hr at 42~C, diluted to 200 ul with TE buffer, extracted with 200 ul of phenol-chloroform, and ethanolprecipitated. Samples were resuspended in 8 ul of TE buffer, and 12 ul of a formamide-dye solution was added. Follow heating for 8 min at 90-100~C and chilling on ice, the samples were electrophoresed for 2-3 hr at 300 V on 5% polyacrylamide/8M urea gels. The gels were fixed in 10% and then 1% trichloroacetic acid for 9 min each before drying in a heated vacuum dryer. $^{32}$P-Labeled HaeIII-digested OX174 DNA or MspI-digested pBR322 DNA was used as molecular weight standards. The dried gels were used to expose Kodak XAR-5 film with intensifying screens at −70~C. Densitometry was performed on a Model GS 300 Scanning Densitometer from Hoefer Scientific Instruments.

Exemplary Experiments

In describing the LDL receptor promoter, nucleotide (nt) +1 is assigned to the A of the translation initiation codon (ATG). This convention is employed because multiple transcription start sites located between positions −93 and −79 have been identified, and thus +1 can not be used to refer to a single site of transcription initiation (FIG. 1). The LDL receptor sequences in each of the three plasmids, as shown in FIG. 2, terminated at the same 3' position (−58) which is located within the transcribed region of the gene. The LDL receptor fragments were inserted into the unique HindIII site of pSVO-CAT, a recombinant plasmid that contains the beta-lactamase gene, the origin of replication from pBR322, and the coding sequence for CAT (see Gorman et al. (1982), *Mol. Cell. Biol.*, 2:1044). All of the cloning junctions in the resulting series of LDL receptor-CAT genes (FIG. 2) were verified by DNA sequence analysis and restriction endonuclease mapping.

The 5' ends of the inserted LDL receptor gene fragments extended to different positions upstream (−6500, −1563, and −234). The plasmids were introduced into CHO cells by calcium phosphate-mediated transfection together with a second plasmid containing the gene for neomycin (G418) resistance linked to the SV40 early region promoter. Permanent G418-resistant colonies were selected, and pools of approximately 150 to 600 colonies from each transfection experiment were assayed for expression of LDL receptor-CAT mRNA by primer extension. The cells were incubated for 24 hr either in the absence of sterols (induction medium) or in the presence of a mixture of cholesterol and 25-hydroxycholesterol (suppression medium). This sterol mixture was used because it is more potent than cholesterol alone in suppressing the LDL receptor as well as other sterol-repressed genes.

Figure 3A:
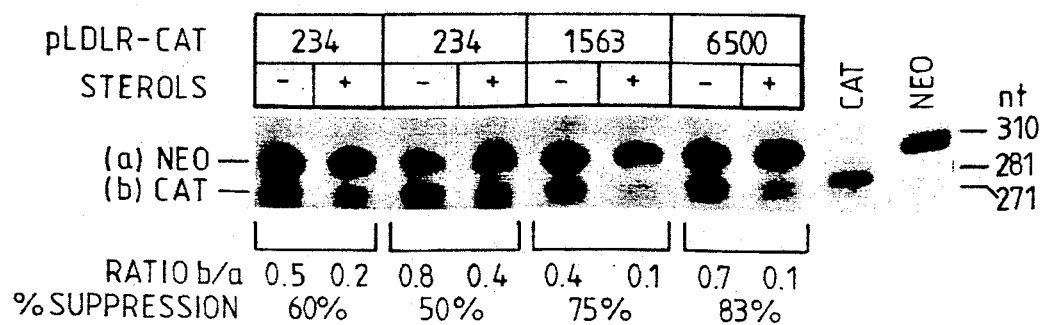
FIG. 3 (parts A and B). Sterol-mediated suppression of transfected and endogenous LDL receptor promoters in CHO cells. Panel A: Pooled CHO cells (150 to 600 colonies) co-transfected with pSV3-Neo and the indicated pLDLR-CAT plasmid were set up for experiments as described in Example I. Two different pools of cells transfected with pLDLR-CAT 234 were studied. The cells were incubated for 20 hr in the absence or presence of 10 ug/ml cholesterol plus 0.5 ug/ml 25-hydroxycholesterol, after which total RNA was isolated from 12 dishes of cells, and an aliquot (20 ug) was used as a template in primer extension assays. Each assay tube contained $^{32}$P-labeled oligonucleotides specific for the transfected neomycin-resistance gene (driven by the SV40 promoter) and the CAT gene (driven by the LDL receptor promoter). The lanes on the far right show the primer extension products obtained when the CAT-specific or neomycin (Neo)-specific primers were used alone. The gel was exposed to X-ray film for 72 hr. For quantitation, the amounts of neomycin (a) and CAT (b) primer extension products were estimated by densitometry, and a ratio (b/a) of CAT-specific to neomycin-specific product was calculated. Percent suppression was determined from this ratio. Panel B: The same RNA samples from Panel A were subjected to primer extension analysis using an oligonucleotide derived from exon 4 of the hamster LDL receptor (LDLR) gene plus the neomycin (Neo)-specific oligonucleotide. The lane on the far right shows the result obtained with the hamster LDL receptor primer alone. The black dots represent four products derived from the endogenous LDL receptor mRNA. The longest extension product (575 nt, designated C) represents full-length extension to the mRNA cap site. The three shorter bands represent strong-stop sequences encountered by the reverse transcriptase enzyme. Quantitation of "% suppression" was determined as described in Panel A. The gel was exposed to X-ray film for 48 hr. For Panels A and B, the positions to which DNA fragments of known size migrated are indicated on the right in nucleotides (nt).

Cells transfected with each of the three LDL receptor-CAT plasmids produced a fusion mRNA that initiated in the receptor cap region as determined by primer extension with a $^{32}$P-labeled oligonucleotide specific for the CAT coding sequence (FIG. 3A). To assay for sterol-specific suppression of the LDLR-CAT mRNA, the amount of mRNA produced by the co-transfected neo gene was determined simultaneously. The expression of this gene is driven by the constitutive SV40 early region promoter and does not respond to sterols. When the transfected CHO cells were grown in the presence of sterols, the amount of mRNA transcribed from the various LDL receptor-CAT genes was suppressed by 50-83% relative to the amount of neo mRNA (FIG. 3A). To ensure reproducibility of these assays, they were repeated on three different lines of CHO cells that were transfected with the pLDLR-CAT constructs on three separate occasions; all cell lines gave similar results. FIG. 3 shows the results with two separate −234 constructs. These data show that the most important sequences for expression and sterol regulation of the LDL receptor gene are contained within the 177-bp fragment extending from position −234 to −58. Identical results were obtained when these same LDLR-CAT genes were transfected into an SV40-transformed line of human fibroblasts, human epidermoid carcinoma A431, mouse Y1 adrenal cells, and mouse L cells (data not shown). These results indicate the general applicability of the LDL receptor promoter and regulatory sequences.

Figure 3B:
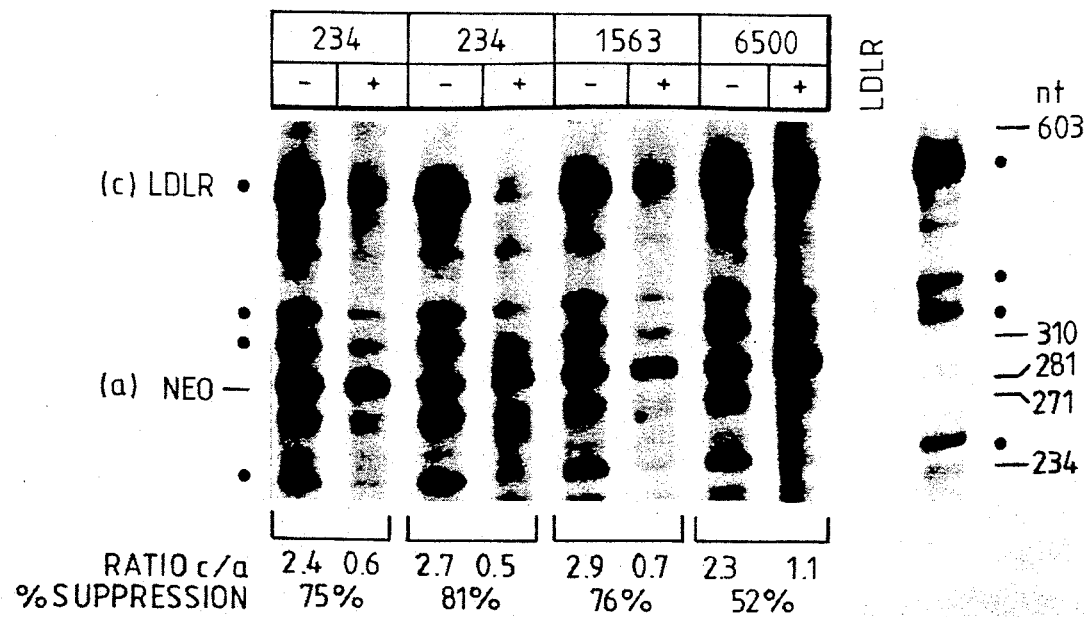

Using the same mRNA samples as those in FIG. 3A, the amount of LDL receptor mRNA derived from the endogenous hamster receptor gene was estimated (FIG. 3B). For this purpose, an oligonucleotide primer was used that is complementary to mRNA sequences encoded by exon 4 of the hamster gene that are located about 575 nt 3′ to the cap site. The use of such a remote oligonucleotide primer was necessary because to date only sequences corresponding to exons 4 through 18 of the hamster LDL receptor gene have been isolated by the present inventors.

In extending over the large distance separating the primer and the 5′ end of the mRNA, the reverse transcriptase encountered several strong stop sites. As a result, a family of primer-extended products was generated (far right lane, FIG. 3B). The most abundant extensions are marked by the black dots in FIG. 3B. In the presence of sterols, all of these primer-extended products were reduced in amount. On the other hand, the primer-extended product corresponding to mRNA derived from the transfected neo gene was not suppressed (FIG. 3B). The relative amount of LDL receptor mRNA suppression was estimated by densitometric scanning of the band corresponding to the full-length prime-extended product (band c) and by comparing it to the primer-extended product of the neo gene (band a). The results showed that sterols suppressed the endogenous LDL receptor mRNA by 52–81% in the various cell lines (FIG. 3B), a degree of suppression that was similar to that observed for the transfected human LDL receptor promoter-CAT gene (50-83%, FIG. 3A).

FIG. 4 shows an experiment designed to compare the sensitivity of the transfected LDLR-CAT promoter and the endogenous LD receptor promoter to increasing concentrations of sterols. For this purpose, the construct that extended to position −1563 in the LDL receptor 5′ flanking region (pLDLR-CAT-1563 of FIG. 2) was used. As a control, another $^{32}$P-labeled oligonucleotide primer was employed to measure the amount of cellular mRNA for thymidine kinase (TK) produced by the endogenous hamster TK gene. The addition of 10 ug/ml cholesterol plus 0.5 ug/ml of 25-hydroxycholesterol produced a nearly complete suppression of the LDLR-CAT mRNA without affecting the level of endogenous TK mRNA (FIG. 4A). This concentration of sterols strongly suppressed the endogenous LDL receptor mRNA in the same cells black dots (FIG. 4B). The amount of mRNA for another hamster cholesterol-suppressed gene, HMG CoA synthase, was also measured using a $^{32}$P-labeled oligonucleotide primer complementary to the synthase mRNA. This primer produced two extended products which reflect the existence of two species of synthase mRNA that differ in the presence or absence of a 59-bp optional exon in the 5′ untranslated region. Both of these transcripts were suppressed by cholesterol plus 25-hydroxycholesterol (FIG. 4B).

Figure 5:
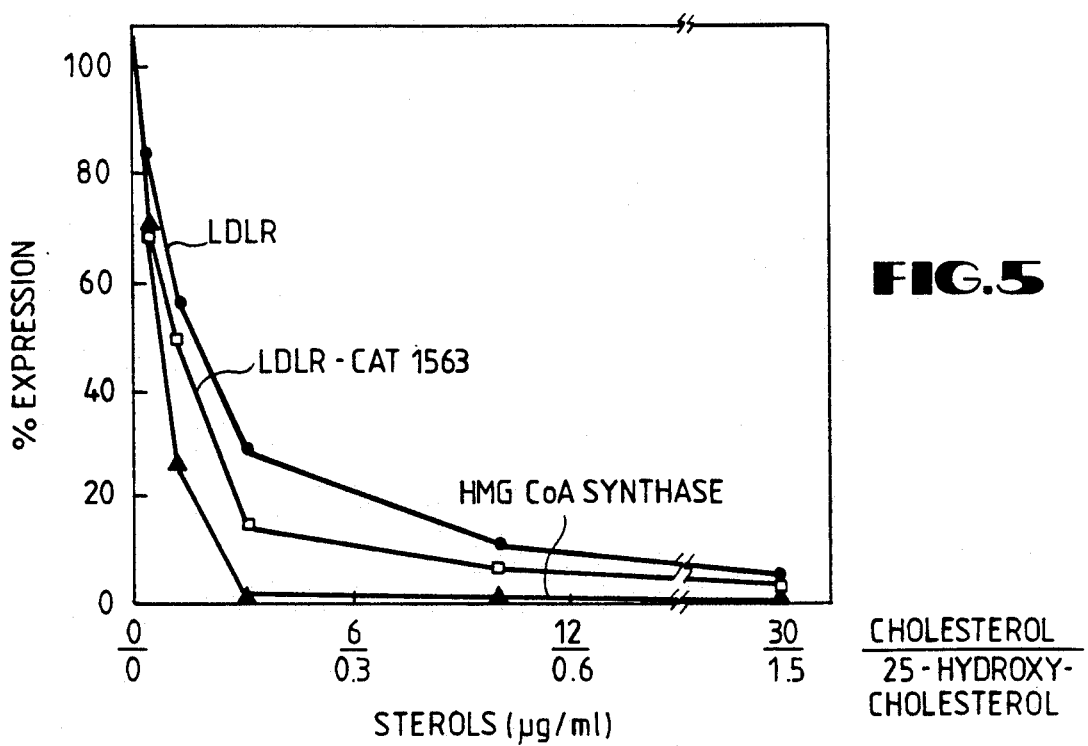
FIG. 5. Quantification of sterol-mediated suppression of transfected and endogenous cholesterol-regulated genes in CHO cells. The amounts of the primer extension products in FIG. 4 corresponding to mRNAs derived from the transfected LDL receptor-CAT 1563 gene, endogenous LDL receptor gene (575-nt product only), and endogenous HMG CoA synthase gene (both products) were estimated by densitometry. The value for "100% expression" represents the amount of primer extension product observed in the absence of sterols.

FIG. 5 summarizes in graphic form the quantitative results of the experiment shown in FIG. 4. These data show that the endogenous LDL receptor mRNA and the mRNA derived from the LDLR-CAT 1563 construct were suppressed in parallel by the sterol mixture. On the other hand, endogenous HMG CoA synthase mRNA was more sensitive to the sterols. Complete suppression of this mRNA occurred at 3 ug/ml cholesterol plus 0.3 ug/ml 25-hydroxycholesterol.

To determine the time course of induction of the mRNA derived from pLDLR-CAT 1563 following the removal of sterols from the medium, the experiment shown in FIG. 6 was performed. Cells were maintained in suppression medium containing 10 ug/ml cholesterol and 0.5 ug/ml 25-hydroxycholesterol for 20 hr and then switched to induction medium (no sterols) for varying time periods. Total cellular RNA was then isolated and subjected to primer extension analysis using oligonucleotides specific for the LDLR-CAT mRNA and the endogenous hamster TK mRNA. The amount of LDLR-CAT mRNA rose 4-fold by 2 hr after sterol removal and reached a maximum (8-fold) at 11 hr (FIG. 6). As expected, there was no change in the level of the endogenous TK RNA.

The experiments of FIGS. 3-6 indicate that fragments of the LDL receptor promoter that include sequences from −234 to −58 are capable of driving expression of the CAT gene in a sterol-responsive manner. To delineate further sequences within this 177-bp fragment that confer positive and negative regulation, the series of 15 promoter mutations shown in FIGS. 7 and 8 were constructed and analyzed. To avoid problems associated with gross deletions, individual overlapping 10-bp segments of the promoter fragment from pLDLR-CAT 234 were scrambled by site-directed mutagenesis (FIG. 7). Each mutant promoter was then transfected into CHO cells on two to five separate occasions, together with pSV3-Neo for G418 selection and pHSVTK-CAT as a transfection control. The latter plasmid contains TK promoter sequences (from −108 to +55) derived from the HSV genome fused to the CAT gene. The HSV TK promoter has been well characterized by McKnight and coworkers (McKnight et al. (1982) Cell, 31:355; McKnight et al. (1982), Science, 234:47) and does not respond to sterols. By comparing the amount of mRNA derived from the HSVTK-CAT gene to that from a transfected LDLR-CAT gene, the relative promoter strengths of the different LDL receptor mutations was estimated and the "% suppression" obtained in the presence of sterols calculated. The results from one primer extension analysis are shown in FIG. 8.

RNA was isolated from CHO cells transfected with pLDLR-CAT 234 and pHSVTK-CAT and grown in the absence of sterols. When this RNA was subjected to primer extension using CAT-specific and endogenous hamster TK-specific $^{32}$P-oligonucleotides, three products were visualized after autoradiography (FIG. 8, left lane of upper panel). Two products were derived from the transfected chimeric CAT genes; the 314-nt band is from mRNA initiated at the correct cap site of the HSVTK-CAT gene, while the 290-nt band is the product of the LDLR-CAT gene. The third product is a 260-nt band that corresponds to the primer extension product from the endogenous TK gene. The addition of sterols to the medium resulted in an 83% reduction in the amount of the LDLR-CAT mRNA relative to the HSVTK-CAT mRNA (FIG. 8, second lane of upper panel). A similar reduction was calculated using the endogenous TK mRNA as a standard (data not shown).

Experiments with the mutated LDL receptor-CAT genes yielded qualitatively similar results with respect to sterol regulation. Nine of the mutated promoters produced an mRNA whose transcription was suppressed in a normal manner in response to sterols. One mutation (−186/−177) responded less well to sterols, suppressing transcription of the LDLR-CAT mRNA by only 25% (FIG. 8). However, in this case the overall transcription of the mutant gene was substantially reduced, making it difficult to accurately measure suppression.

Figure 9:
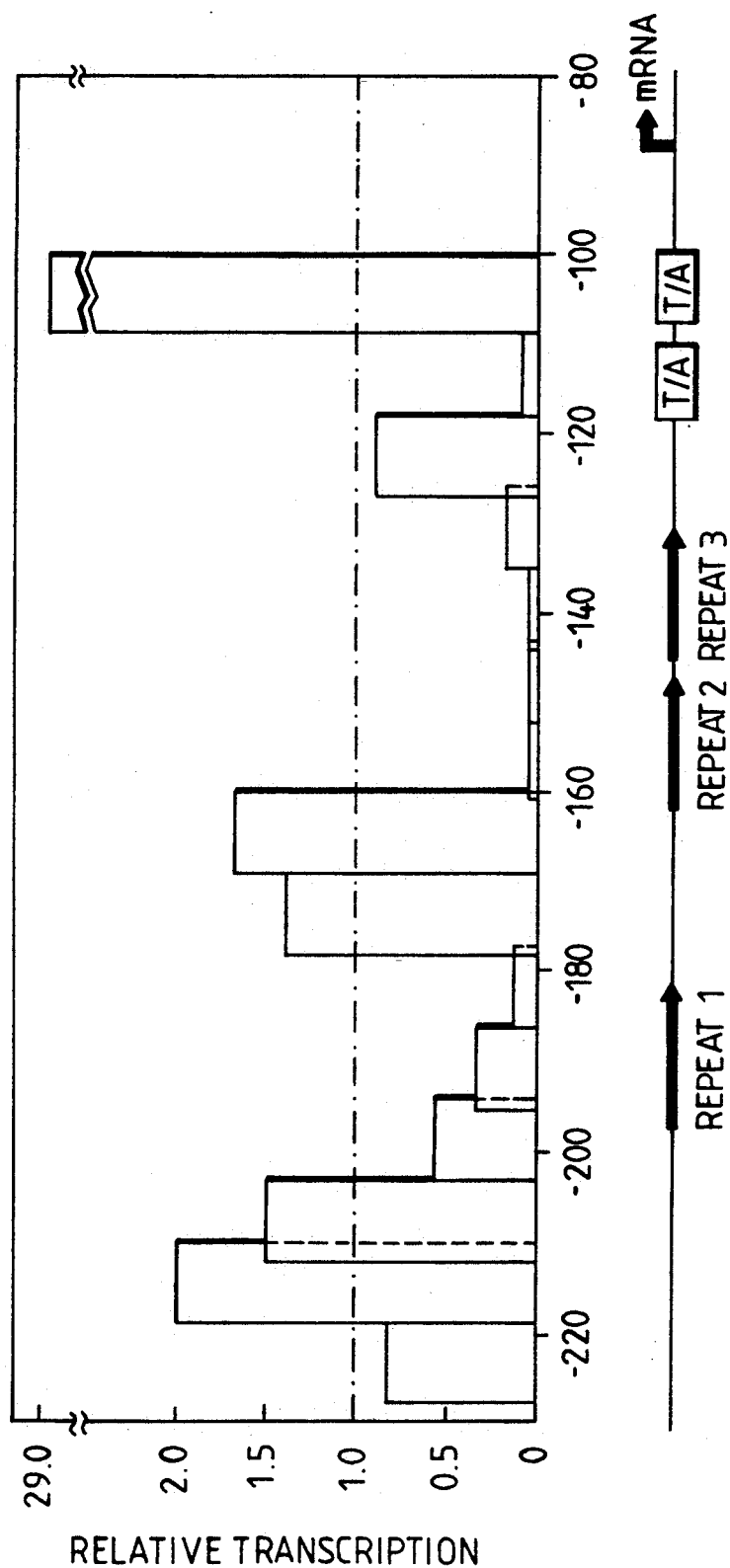
FIG. 9. Relative transcription activity of normal and mutant LDL receptor promoters. Relative transcription activity is expressed as the ratio (b/a) of the amounts of primer extension products corresponding to mRNAs derived from the transfected LDL receptor-CAT gene (b) and from the HSVTK-CAT gene (a) as shown in FIG. 7. A value of 1.0 (dashed horizontal line) was assigned to the ratio comparing the normal LDL receptor promoter (pLDLR-CAT 234) to the HSVTK-CAT promoter. The ratios obtained from the 15 different scramble mutations (FIG. 7) and their relative locations in the LDL receptor promoter are indicated by the height and width of the blocks, respectively, in the histogram. The data shown represent the average of 2 to 5 separate transfection experiments. A schematic of the normal LDL receptor promoter and its relevant landmarks is shown at the bottom of the figure.

Many of the scramble mutations dramatically affected positive expression (FIG. 8). To compare relative transcription levels between the mutant genes, a value of 1.0 was assigned to the amount of mRNA transcribed from the transfected normal LDLR-CAT 234 gene in the absence of sterols (b) divided by that from the HSVTK-CAT gene (a). A similar ratio was calculated from each of the scramble mutations based on the data shown in FIG. 8 and on two to four additional experiments. These ratios are plotted in histogram form in FIG. 9, where the ordinate represents relative transcription and the abscissa represents DNA sequences from the human LDL receptor promoter. This data indicate that mutations that scramble sequences residing in any of the three direct repeats reduce transcription 50 to >95%. Similarly, a mutation that disrupts the more 5' of the two TATA sequences decreases transcription by more than 90% (FIG. 9). Several of the mutations increased transcription moderately (approximately 2-fold). Surprisingly the mutation that scrambled the more 3' TATA sequence (−109/−100) increased the amount of LDLR-CAT mRNA some 29-fold. This number probably represents an overestimate of the relative promoter activity of the −109/−100 mutation in that the cotransfected HSVTK-CAT gene to which it was compared was transcribed poorly in these cells (see FIG. 8). Identical results were obtained using RNA from two separate transfections with this mutant indicating that the reduced HSVTK-CAT transcription was not due to differential transfection of the two plasmids.

EXAMPLE I OVERVIEW

The data presented by the foregoing experiments define a minimal DNA region from the human LDL receptor gene to which expression and sterol-dependent regulation functions may be ascribed, at least in the context of the LDL receptor gene per se. When fused to a bacterial marker gene and transfected into CHO cells, 5'-flanking DNA from the receptor gene directed the synthesis of a correctly initiated mRNA that was decreased in amount when sterols were added to the medium (FIG. 3). Titration experiments revealed that the response to exogenously added sterols was equivalent for both a transfected gene having human receptor sequences between −1563 and −58 and the endogenous hamster LDL receptor gene (FIG. 5). The kinetics of induction of this mRNA were rapid; half-maximal expression was obtained 2 hr after removal of sterols (FIG. 6). These results indicate that the turning on of the LDL receptor promoter signals when sterols are removed from the media is very rapid.

By further reducing the amount of human receptor DNA in the fusion gene, a segment spanning sequences between −234 and −58 was found to be sufficient for the expression of a sterol-responsive mRNA. The amount of mRNA transcribed from this construct and its sterol response were identical to mRNAs synthesized from the chimeric genes containing larger amounts of 5'-flanking receptor DNA, indicating that no important transcription signals for regulation and expression had been deleted (FIG. 3).

The 177-bp fragment of receptor DNA in pLDLR-CAT 234 was small enough to allow a further delineation of transcriptionally important sequences by a form of saturation mutagenesis. To this end, 15 mutations were introduced by site-directed oligonucleotide mutagenesis in which overlapping 10-bp segments were scrambled. The results from transfection experiments with these plasmids indicated that all three of the 16-bp direct repeats in the receptor promoter are required for maximal expression (FIG. 9). In addition, the more 5' of the two TATA-like sequences (TTGAAAT) was required for maximal expression. Surprisingly, a mutation which scrambled sequences in the 3' TATA-like sequence (TGTAAAT) led to a marked increase in transcription from the mutant gene (FIG. 9). The mechanism behind this promoter-up phenotype is at present not known, although it was noted that the mutation did not alter the start site of transcription, as an identical primer extension product is obtained with mRNA from cells transfected with this construct (FIG. 8). Neither of these TATA-like sequences match well the canonical sequence TATAAA derived from many other eukayrotic genes. Thus, it is conceivable that the more 3' element may play more of a regulatory role (as observed here) than as a signal for precise mRNA start site selection as observed in other genes. Future studies with the pLDLR-CAT −109/−100 construct should clarify the role of this sequence.

With respect to the direct repeats, mutations that alter repeat 1 decrease transcription to a slightly lesser extent (50-90%) than those that alter repeats 2 and 3 (80-95% decrease). These differences may be real, implying non-equivalence of the three repeats with respect to expression, or they may be a consequence of the exact sequence scrambled in a given repeat. In this light, it is notable that a mutation that alters as few as 3 bp of a direct repeat leads to decreased transcription: mutation −203/−194 alters the 5'-three nucleotides of repeat 1 and reproducibly decreased mRNA synthesis 50% (FIG. 8). These results imply that each direct repeat sequence is recognized essentially in its entirety by a transcription factor or factors.

In considering which of the known transcription factors might interact with these sequences, it was discovered that the central core of the LDL receptor direct repeats shares sequence homology with the so-called "GC boxes" found in other eukayrotic RNA polymerase II promoters (Kadonaga et al. (1986), *Trends Biochem. Sci.*, 11:20). Table 1, below, indicates that repeats 1, 2 and 3 have 8 of 10, 7 of 10, and 9 of 10 matches, respectively, with a consensus GC box sequence. Tijan and colleagues have recently isolated in homogeneous form a protein termed transcription factor Spl (Briggs, e al. (1986), *Science*, 234:47) and have shown that in several viral and cellular promoters this protein stimulates transcription by binding to GC sequences (Dyan et al. (1985), *Nature*, 316:774). Initially, it was postulated that Spl had a recognition sequence of 10 nucleotides with a central core consisting of CCGCCC, which is not found in any of the three direct repeats of the LDL receptor promoter (Table II).

TABLE II

GC Box Homologies in the Direct Repeats of the Human LDL Receptor Promoter

| | |
|---|---|
| Repeat 1 | A A A C T C C T C C T C T T G C |
| Repeat 2 | A A A A T C A C C C C A C T G C |
| Repeat 3 | A A A C T C C T C C C C C T G C |
| GC Box Consensus* | $\begin{array}{c}GCC\\ATT\end{array}$ C C G C C C $\begin{array}{c}C\\A\end{array}$ |

Nucleotides in repeats 1, 2 and 3 that differ from the GC box consensus sequence are underlined.
*From Kadonaga et al. (1986), Trends Biochem. Sci., 11:20-23.

More recently, two decanucleotide sequences that differ from the Sp1 consensus sequence by 2 positions in the canonical CCGCCC, have been shown to bind Sp1 and activate transcription from the human immunodeficiency virus (HIV) long terminal repeat promoter (Jones et al. (1986), Science, 230:511). This observation suggests to the present inventors that there is some flexibility for deviation from the Sp1 consensus sequences and raises the possibility that the sequences in repeats 1 and 3 of the LDL receptor, which differ by 1 and 2 positions, respectively, from CCGCCC, are in fact Sp1 binding sites (Table II). In this regard, repeats 1 and 3 of the LDL receptor promoter bind a protein present in HeLa cell nuclei which protects these sequences from digestion with DNAase I (see Example II). The protected regions span about 20 bp each, which is similar in size to protection obtained with homogeneous Sp1.

The studies disclosed below in Example II demonstrate that direct repeats 2 and 3 of the human receptor gene function as a translocatable sterol regulatory element (SRE). For example, in these studies it is shown that the insertion of a 42-bp fragment spanning these two repeats into the promoter of the HSVTK gene confers negative regulation by sterols on the expression of the chimeric gene. The studies in the present example show that in addition to harboring an SRE sequence, these two direct repeats also contain positive transcription signals. Furthermore, none of the scramble mutations analyzed in FIG. 8 led to a constitutive promoter, indicating that the sterol-regulatory and positive expression sequences of the LDL receptor promoter are intimately related. If these signals are the same, it is conceivable that competition for binding between a sterol repressor and Sp1, or an Sp1-like transcription factor, to a direct repeat sequence may underly the ability of sterols to repress transcription from the LDL receptor gene. Future studies centered around the purification of the proteins that interact with repeats 2 and 3 may provide support for this hypothesis.

EXAMPLE II

Isolation and Characterization of the LDL Receptor Sterol Regulatory Element

In Example I, the expression of chimeric genes containing various sequences from the 5' flanking region of the LDL receptor gene (ranging at the 5' end from −6500 to −234 and terminating at position −58) fused to the CAT gene were analyzed. The results showed that a 177-bp sequence from the receptor promoter (−234 to −58) is capable of driving expression of the CAT gene in a sterol-responsive manner. In the present example, experiments are presented which demonstrate that all three direct repeats are not required in order to confer sterol-responsive transcription to heterologous genes. In general, the following experiments surprisingly demonstrate that a functionally translocatable SRE resides within a 42 base pair sequence which contains repeats 2 and 3, but not repeat 1, and which are solely responsible for conferring sterol responsivity to heterologous structural genes. Further experimentation conducted by the present inventors has demonstrated that the SRE is contained solely within repeat 2.

SELECTED MATERIALS AND METHODS EMPLOYED FOR EXAMPLE II

Materials were obtained from those sources listed above in Example I. Plasmids were constructed by standard techniques of genetic engineering (Maniatis, et al., (1982)) and verified by DNA sequence analysis and restriction mapping. Plasmid A was derived from pTKdelta32/48 of McKnight and Kingsbury (1982), Science, 217:316, and pTK-CAT of Cato, et al. (1986), EMBO J., 5:2237. Plasmids B through D were constructed by ligating the indicated LDL receptor promoter sequences (synthesized on an Applied Biosystems Model 380A DNA Synthesizer) into the HindIII-BamHI sites at −32 of the truncated HSV TK promoter in plasmid A. Plasmid E, which contains HSV TK sequences from −60 to +55, was constructed from pTK-CAT (Cato, et al., supra) and pTKdelta60/80 (McKnight and Kingsbury, supra). Plasmids F through H were engineered by ligating synthetic LDL receptor sequences into the HindIII-BamHI sites at −60 of the truncated HSV TK promoter.

Plasmids I-N contained the entire active HSV TK promoter extending from −480 through +55 except for the sequence between −48 and −32, which was replaced with short sequences corresponding to various parts of the sterol regulatory element of the LDL receptor promoter. The starting plasmid (I) was engineered from pTK-CAT (Cato, et al, supra) and plasmid LS-48/-32 of McKnight 1982), Cell., 31:355. Plasmid I thus contains an active HSV TK promoter (with a 10-bp BamHI linker replacing viral sequences between −48 and −32) linked to the CAT gene. To construct plasmids J, K, and M, a pair of complementary oligonucleotides 42 bases in length (see Table III) were synthesized on a Model 380A DNA synthesizer, annealed, phosphorylated at their 5' ends using ATP and T4 polynucleotide kinase, and ligated into BamHI-cleaved plasmid I. The three desired plasmids containing varying numbers and orientations of the 42-mers were then identified by restriction mapping and DNA sequencing. Plasmids I and N and O through R were constructed in a similar manner except that oligonucleotides of different sequences (Table III) were employed in the ligation.

DNA Transfection. CHO-KI cells were cultured, transfected with plasmids, and selected with G418 as described by Davis, et al. (1986), J. Biol. Chem., 261:2828. After 2-3 weeks of selection, resistant colonies were pooled (300-600 per transfection), expanded in mass cultures in the presence of G418 (700 ug/ml), and used for experiments.

Sterol-Regulation Experiments. Pooled cell lines were seeded at $2 \times 10^5$ cells per 100-mm dish on day 0 in medium A supplemented with 10% fetal calf serum. In the standard protocol, on day 2 the cells were washed with 7 ml phosphate-buffered saline and fed with 8 ml of medium A containing 10% calf lipoprotein-deficient serum in place of whole fetal calf serum. This medium contained either no additions (induction medium) or a mixture of cholesterol and 25-hydroxycholesterol in a ratio of 20:1 added in 4-26 ul ethanol (suppression medium). On day 3 after incubation for 20 hr in induction or suppression media, the cells from 12 dishes were harvested in 4 M guanidinium thiocyanate containing 6.25 g/l lauroyl sarcosine, 9.2g/l sodium citrate, and 0.7% (v/v) 2-mercaptoethanol, and the total RNA was purified by centrifugation fugation through CsCI (Chirgwin, et al., (1979), *Biochemistry*, 18:5294). The RNA pellet was dissolved in buffer containing 10 mM Tris-chloride and 1 mM EDTA at pH 8.0 (TE buffer), precipitated with ethanol, and then quantitated by $OD_{260}$.

Primer Extension Assays. To detect transcripts containing CAT sequences, we used an mRNA-complementary primer of 40 nt corresponding to bases 400 to 439 of the published gene sequence (Alton and Vapnek (I1979), *Nature*, 282:864). Endogenous hamster TK mRNA was detected with a 43-nt long primer derived from bases 198 to 240 of the published cDNA sequ®nce (Lewis, (1986), *Mol. Cell. Biol.*, 6:1978). Endogenous hamster HMG CoA synthase mRNA was measured by extension with a 40-nt long primer corresponding to bases 41 to 80 of the cDNA sequence (Gil, et al., supra). Endogenous hamster LDL receptor mRNA was detected with an oligonucleotide primer of 36 nt whose sequence was derived from exon 4 of the hamster gene (unpublished observations). $^{32}$P-End labeled oligonucleotide primers were hybridized with 20 ug total RNA and extended according to a protocol modified from McKnight and Kingsbury (1982) (see Example I). The extension products were analyzed on 5% acrylamide/8M urea gels. After electrophoresis gels were fixed and dried before being exposed to intensifying screens at $-70°$ C. Densitometry was performed on a Hoefer scanning densitometer (Model GS-300).

Exemplary Studies

FIG. 1 shows the nucleotide sequence of the coding strand of the LDL receptor gene in this general region. The cluster of transcription start sites at positions $-93$ to $-79$ is indicated. The prominent features of this region include two AT rich sequences ($-116$ to $-101$) that may contain the equivalent of a TATA box. To the 5' side of this region, there is a segment that contains 3 imperfect direct repeats of 16 bp, two of which are in immediate juxtaposition. These repeats are aligned at the bottom of the figure.

Sterol-Mediated Suppression of LDL Receptor HSV TK Genes

Figure 10:
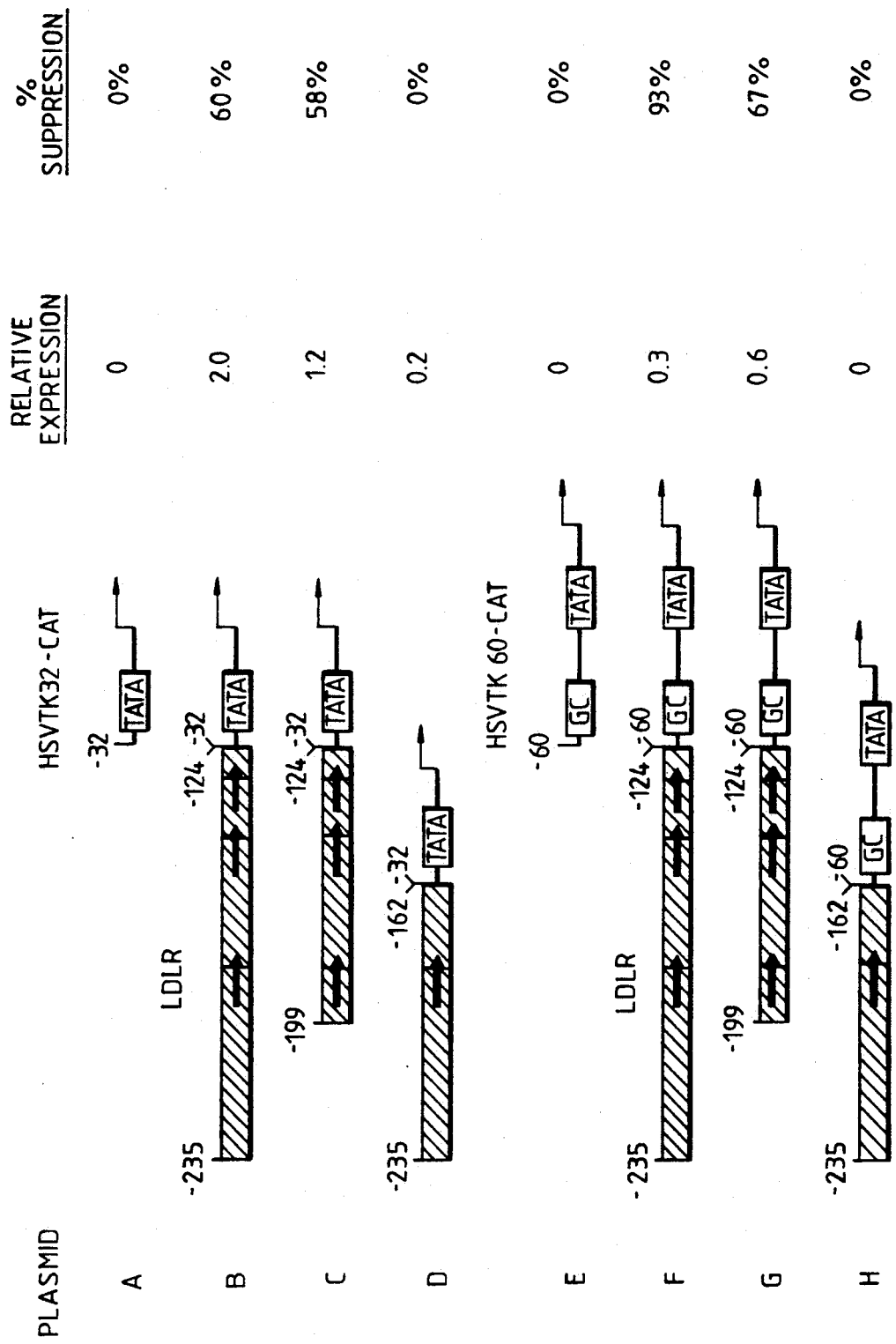
FIG. 10. Structure of plasmids containing LDL receptor promoter linked to HSV TK-CAT gene. Different fragments of the human LDL receptor promoter DNA were linked to the HSV TK promoter at position −32 (plasmids B-D) or −60 (plasmids F-H). The starting plasmid HSV TK 32-CAT (A) contains 32 bp upstream of the viral TK cap site and includes a TATA sequence as well as 55 bp to TK 5' untranslated sequences. The plasmid HSV TK 60-CAT (E) contains 60 bp upstream of the cap site of the viral TK gene and includes a TATA sequence and the first upstream regulatory signal (GC box) of the viral promoter. The 5'-flanking sequences of the LDL receptor gene are denoted by the hatched line and are numbered according to FIG. 1. Three 16-bp imperfect direct repeats are indicated by thick black arrows.

Three overlapping fragments of the LDL receptor promoter were synthesized and linked to HSV TK sequences extending from $-32$ to $+55$ (plasmids A-D, FIG. 10 or from $-60$ to $+55$ (plasmids E-H, FIG. 10). HSV TK sequences between $-32$ and $+55$ contain the TATA box and cap site of this viral gene, whereas sequences between $-60$ and $+55$ also include the first upstream promoter element (GC box). These LDL receptor-HSV TK plasmids were introduced into CHO cells by calcium phosphate-mediated transfection together with a second plasmid containing the gene for neomycin (G418) resistance. Permanent G418-resistant colonies were selected, and pools of 300-600 colonies were assayed for expression of LDL receptor-CAT mRNA by primer extension. The cells were incubated for 24 hr either in the absence of sterods (induction medium) or in suppression medium that contained a mixture of cholesterol and 25-hydroxy-cholesterol. cholesterol. As a control for specificity of suppression, the amount of endogenous hamster TK mRNA was measured. To establish a baseline of expression for comparative purposes, the ratio of the amount of mRNA produced by the transfected gene divided by that produced by the endogenous hamster TK gene (as determined by densitometric scanning of the bands was calculated).

The fragment of the TK promoter extending to position $-32$ includes the TATA box but lacks two upstream elements necessary for transcription. As expected, this plasmid (plasmid A) did not produce detectable amounts of CAT mRNA in the CHO cells. When a fragment of the LDL receptor extending from position $-235$ to position $-124$ was placed in front of the TK 32 promoter fragment, detectable amounts of a mRNA which initiated at the HSV TK cap site were produced (plasmid B). The amount of this mRNA was reduced by 60% when sterols were present. A similar effect was seen when a smaller fragment of the LDL receptor (extending from $-199$ to $-124$) was used (plasmid C). On the other hand, when a fragment encompassing sequences between $-235$ and $-162$ (which lacked repeats 2 and 3, but included repeat 1 of the LDL receptor promoter) was fused to the TK 32 DNA (plasmid D), only trace amounts of a CAT mRNA were produced, and there was no suppression by sterols. Comparable results were obtained when the same fragments of the LDL receptor promoter were linked to position $-60$ of the HSV TK gene just to the 5' side of its first upstream promoter element (plasmids E-H in FIG. 10). The relative amounts of suppression by sterols were similar in both cases.

The data shown in FIG. 10 indicate that fusion of a DNA fragment containing all three 16-nt direct repeats of the LDL receptor promoter to either HSV TK-CAT gene (TK 32 or TK 60) results in the sterol-regulated expression of correctly initiated mRNAs (plasmids D and H). However, insertion of a fragment containing only the first direct repeat led to very little transcription of the fusion gene, and regulation was not observed. These studies demonstrate that repeats 2 and 3 contain both positive and negative elements of sterol-regulated expression.

Fusion Genes Containing LDL Receptor SRE Linked to HSV TK

Figure 11A:
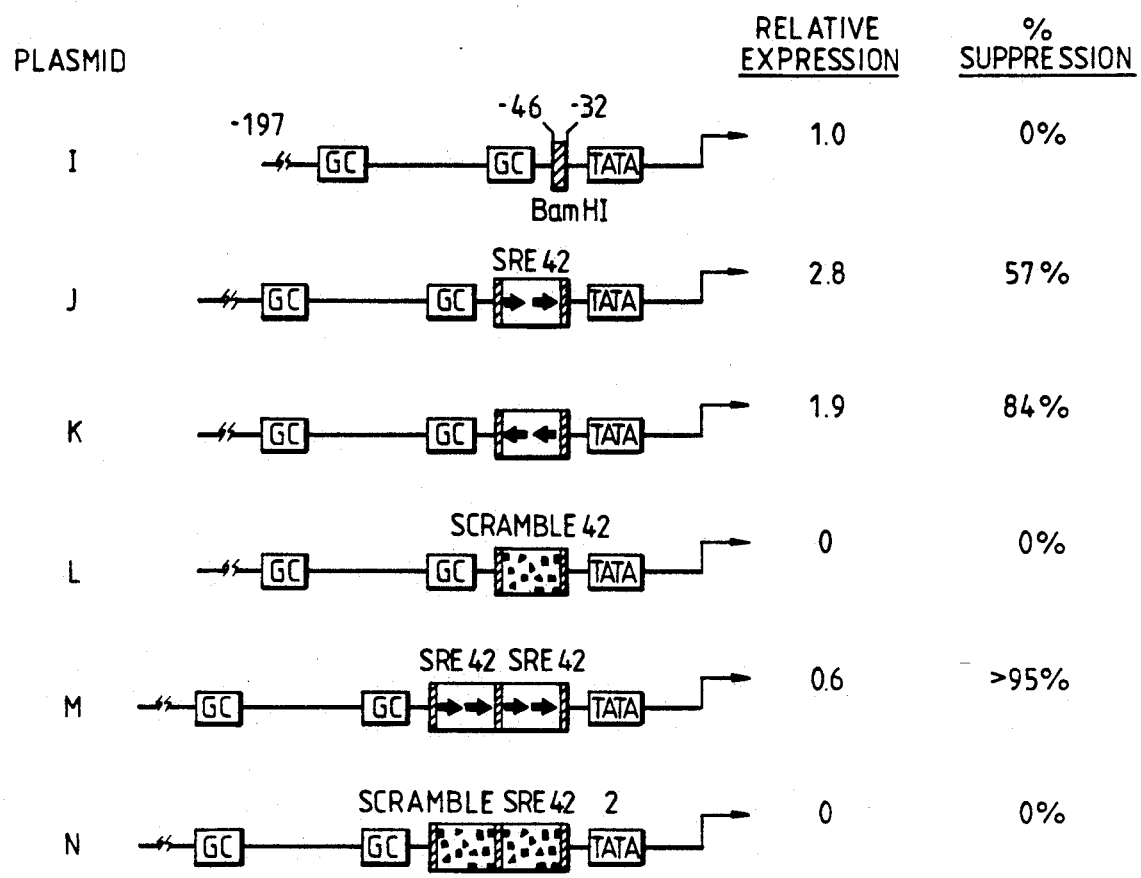
FIG. 11. (parts A and B Sterol-mediated regulation of HSV TK promotor containing synthetic LDL receptor SRE (42-mer). Top Panel: A synthetic 42-bp fragment of DNA corresponding to sequences between −165 and −126 of the human LDL receptor promoter (SRE 42) was inserted in varying numbers and orientations into a plasmid containing the HSV TK promoter linked to CAT (Table II). Each 42-bp sequence contains two copies of an imperfect =16 bp direct repeat denoted by heavy arrows. The viral TK-CAT plasmid (plasmid I) contains a 10-bp BamHI linker (hatched areas) between positions −48 and −32 relative to the TK cap site. Bottom Panel: Plasmids I–N were transfected into CHO cells. Each resulting pooled cell line (300–600 colonies) was set up for experiments according to the standard protocol. The cells were incubated for 20 hr in the absence or presence of 10 ug/ml cholesterol and 0.5 ug/ml 25-hydroxycholesterol, after which 20 ug of total RNA was used as a template for primer extension analysis employing $^{32}$P-labeled oligonucleotides specific for the mRNAs of the transfected HSV TK-CAT gene product, the endogenous hamster TK gene product, and the endogenous HMG CoA synthase gene product. The gel was exposed to X-ray film for 72 hr. For quantitation of "% suppression", the relative amounts of the viral (b) and endogenous (a) TK primer extension products were determined by densitometry, and a ratio (b/a) of the two was calculated. Only one of the two synthase mRNA products is shown.
Figure 11B:
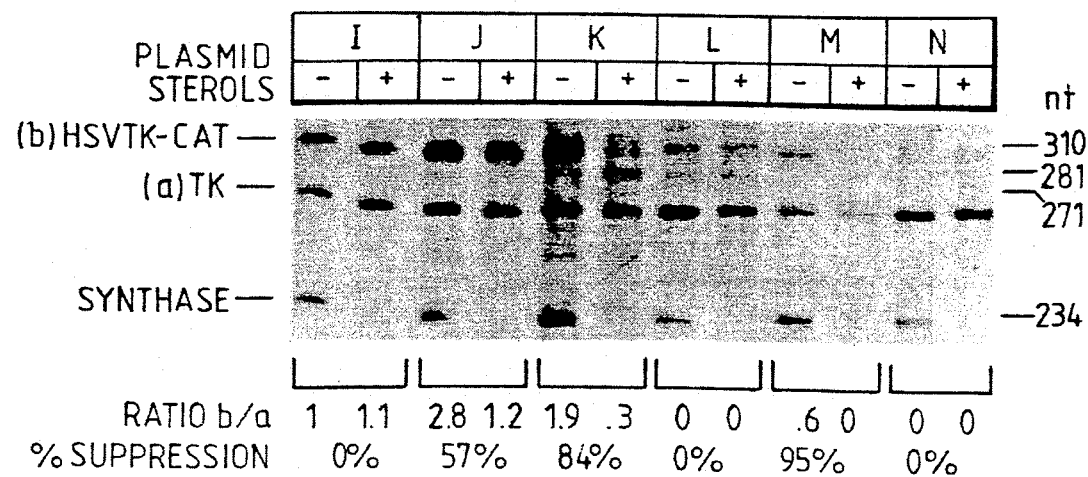

To further evaluate the role of direct repeats 2 and 3 in sterol-mediated suppression, synthetic oligonucleotides corresponding to these sequences were prepared and inserted into an HSV TK promoter containing a BamHI linker between positions $-48$ and $-32$ (FIG. 11). In contrast to the earlier constructs, this HSV TK promoter retains all three signals required for expression of the viral gene. Previous studies by McKnight ((1982), *Cell.*, 31:355) have shown that the insertion of 42 bp at the position of the BamHI linker in this HSV TK promoter reduces transcription moderately. Insertion of longer fragments (>50 bp) eliminates the promoter activity of this DNA.

A synthetic DNA fragment of 42 bp (designated SRE 42 for sterol regulatory element of 42 bp) that contained direct repeats 2 and together with 5 bp of flanking sequence on both sides (Table II) was prepared. This fragment was synthesized with BamHI compatible sticky ends and ligated into the BamHI linker of pHSV TK-CAT. After transfection and primer extension analysis, the results shown in FIG. 11 were obtained. The starting construct with the BamHI linker produced measurable amounts of a correctly initiated mRNA (plasmid I) as expected. There was no suppression of transcription when sterols were added to the medium. Insertion of the LDL receptor SRE 42 within the BamHI linker (plasmid J) also led to the synthesis of the appropriate mRNA. However, when these cells were incubated with sterols, the amount of this mRNA declined by 57%. When the SRE 42 sequence was inserted in an orientation opposite to that found in the LDL receptor (plasmid K), the expected mRNA was still transcribed. Moreover, the amount of mRNA was reduced by 84% when sterols were added. To control for sequence specificity of the 42-bp SRE, the sequence was scrambled into a random order without changing its base composition or length (Table II). When this scrambled sequence was inserted at the BamHI linker of the HSV TK promoter, it abolished transcription (plasmid L) (FIG. 11).

was measured and it was suppressed at lower levels of sterols than was the receptor mRNA.

DNAase I Footprinting of LDL Receptor Promoter - In an effort to further define the SRE of the LDL receptor, experiments were conducted to identify by DNAase footprinting. nuclear protein factors that might interact with this element. Accordingly, a fragment of the LDL receptor promoter extending from −1563 to −58 was 5' end-labeled on the coding strand by a method described below. A $^{32}$P-end labeled, double stranded DNA probe was synthesized by hybriding a $^{32}$P-end labeled oligonucleotide to a complementary M13 clone containing the LDL receptor promoter sequence (-1563 to -58). Double stranded DNA was obtained after extension of the primer in the presence of unlabeled dNTPs and used for footprinting after two phenol-chloroform and chloroform extractions. Footprinting was performed as described by Briggs, et al. (1986), *Science*, 234: 47, using HeLa cell nuclear extracts prepared by the method of Dignam et al. (1983), *Nucl. Acids Res.*, 11: 1475.

Four distinct protected regions, or footprints, were

TABLE III

| Synthetic DNA Fragment | LDL Receptor SRE Fragments Sequences[a] | Plasmid[b] |
|---|---|---|
| SRE 42 | \|——Repeat 2——→\|——Repeat 3——→<br>GAtcTTTGAAAATCACCCCACTGCAAACTCCTCCCCCTGCTA<br>AAACTTTTAGTGGGGTGACGTTTGAGGAGGGGGACGATCTag | J,K,M |
| Scramble 42 | GAtcTTTGAt gcat gt agt cagcgcgct cat ggCat gTGCTA<br>AAACT acgt acat cagt cgcgcgagt accGt acACGATCTag | L,N |
| Footprint 3 | gatCCCCACTGCAAACTCCTCCCCCTGCa<br>GGGTGACGTTTGAGGAGGGGGACGtCTag | O,P |
| Single repeat 3 | gaTct AAACTCCTCCCCCTGCa<br>aTTTGAGGAGGGGGACGtCTag | Q,R |

[a]Nucleotides identical to the LDL receptor promoter are capitalized.
[b]See FIGS. 4 and 7 for plasmid descriptions.

HSV TK promoters containing two copies of the SRE 42 sequence for a total insertion of 84 bp (plasmid M) also express a correctly initiated mRNA and the degree of suppression by sterols (>95%) was more than that achieved with a single copy. When an 84-bp scrambled sequence was inserted into the HSV TK promoter (plasmid N), transcription was abolished (FIG. 11). In all experiments using plasmids I-N, the added sterols did not suppress endogenous CHO TK mRNA (FIG. 11). The amount of mRNA for another hamster cholesterol-suppressed gene, HMG CoA synthase was also measured, using a $^{32}$P-labeled oligonucleotide primer complementary to the synthase mRNA (FIG. 11). This primer produced two extended products which reflect the existence of two species of synthase mRNA that differ in the presence or absence of a 59-bp optional exon in the 5' untranslated region. Both of these transcripts were completely suppressed by cholesterol plus 25-hydroxycholesterol; only the larger of the two products is shown in FIG. 11.

The HSV TK-CAT plasmid containing two copies of the 42-bp SRE from the LDL receptor gene (plasmid M) showed the same sensitivity to sterol suppression as did the endogenous LDL receptor gene. The hybrid plasmid was suppressed 80% at a concentration of 10 ug/ml of cholesterol plus 0.5 ug/ml of 25-hydroxycholesterol, which was similar to the level at which the endogenous receptor promoter was suppressed in the same cells. Endogenous synthase mRNA in these cells seen. Footprint 4 was located at −116 to −101, which is in the region of the TATA-like sequences. Footprint 3 extended from −151 to −129, encompassing repeat 3 plus six bp on the 3' end of repeat 2. Footprint 2 corresponded almost exactly to repeat 1 at −196 and −181. Footprint 1 corresponded to a longer sequence that was located further upstream (−250 to −219). Footprint 3 was of particular interest because it mapped within the SRE-42 sequence that had been identified as important for both promotion and suppression of LDL receptor activity in the HSV TK constructs (FIG. 11). This result suggested that the 23 bp protected from DNAase I digestion in footprint 3 might constitute the minimum amount of DNA required for an SRE. To test this hypothesis, we prepared synthetic oligonucleotides corresponding to footprint 3 and inserted them into the TK promoter.

Figure 12A:
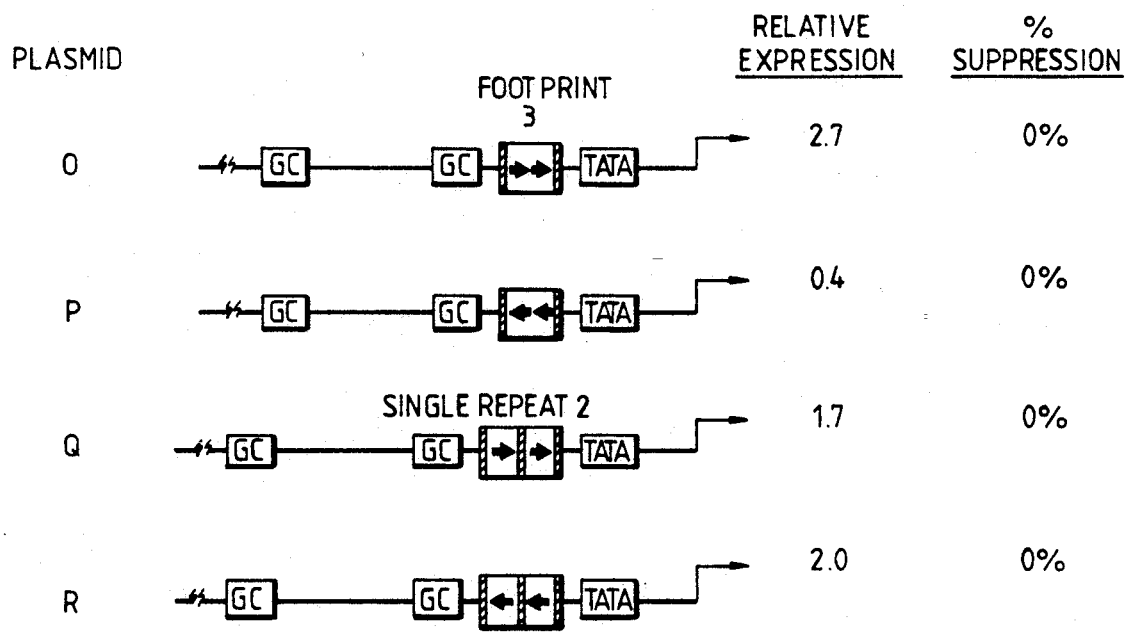
FIG. 12 (parts A and B. Structure of plasmids containing synthetic footprint 3 or repeat 3 sequences from LDL receptor promoter inserted into HSV TK-Cat gene. Top Panel: Plasmids O through R were constructed using plasmid I (FIG. 4) as a starting vector into which two synthetic oligonucleotide sequences were inserted in both orientations (see Table I). Plasmid I contains an HSV TK promoter in which a 10-bp BamHI linker has been substituted for sequences between −32 and −48. Plasmids Q and R contain two copies of one of the 16-bp direct repeats found in the human LDL receptor promoter. The direct repeat sequences in plasmids Q and R are separated by a AGATCT linker (hatched regions). Bottom Panel: Plasmids O-R were transfected into CHO cells. Each resulting pooled cell line (300–600 colonies) was set up for experiments according to the standard protocol. The cells were incubated for 20 hr in the absence or presence of 10 ug/ml cholesterol and 0.5 ug/ml 25-hydroxy-cholesterol, after which total RNA was used as a template for primer extension analysis employing 32P-labeled oligonucleotides specific for the HSV TK gene product, the endogenous hamster TK gene product, or the endogenous HMG CoA synthase gene product. The gels were exposed to X-ray film for 72 hr. For quantitation of "% suppression", the relative amounts of the transfected HSV TK (b) and endogenous (a) TK primer extension products were determined by densitometry, and a ratio (b/a) of the two was calculated. Only one of the two synthase products is shown.
Figure 12B:
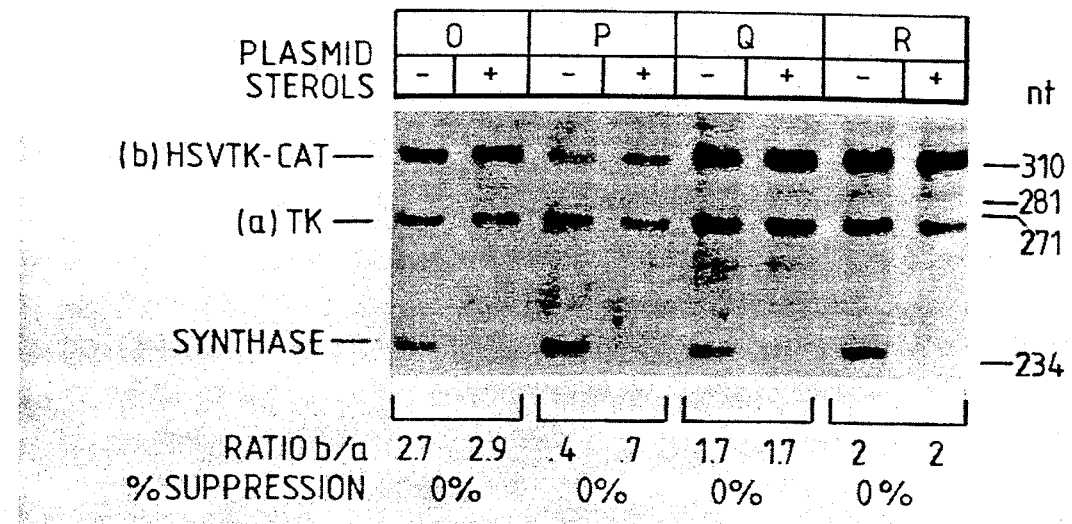

Fusion Genes Containing Footprint 3 or Repeat 3 of LDL Receptor Promoter Linked to HSV TK - A synthetic DNA fragment corresponding to the region occupied by footprint 3 (see Table III) was inserted into the BamHI linker at position −48/−32 of the HSV TK promoter (plasmid 0, FIG. 12). In CHO cells transfected with this plasmid, a correctly initiated mRNA was transcribed; however, there was no suppression by sterols. A similar lack of suppression was seen when the footprint 3 region was inserted in an inverted orientation (plasmid P).

To determine whether repeat 3 by itself would affect transcription in a sterol-dependent manner, we synthesized a DNA fragment that contained two copies of repeat 3 separated by a 6-bp linker sequence (Table III). HSV TK-CAT plasmids containing these two copies in either orientation (plasmids Q and R) expressed an mRNA that initiated at the HSV TK cap site, but neither plasmid showed sterol-mediated suppression of this transcript (FIG. 12).

Example II Overview

End-product repression of genes that control the biosynthesis of essential substances is a well-understood homeostatic mechanism in bacterial and yeast. The regulation becomes much more complex when a cell can control the uptake of the nutrient as well as its synthesis within the cell. How does a cell choose between external and internal sources? This balance is particularly delicate in mammalian cholesterol homeostasis because the uptake mechanism controls not only the level of cholesterol in cells but also the level of cholesterol in blood. The cells of the body must express sufficient LDL receptors to ensure efficient removal of cholesterol from blood, yet they must not produce too many receptors or cholesterol will accumulate to toxic levels within the cell.

In rapidly growing cultured cells such as fibroblasts, the two sources of cholesterol are balanced in favor of exogenous uptake. As long as LDL is available, cultured fibroblasts preferentially use the LDL receptor to obtain cholesterol and they suppress the biosynthetic pathway. When cellular cholesterol levels decline, the cells increase the number of LDL receptors. If these do not provide sufficient cholesterol, the pathway for cholesterol synthesis is derepressed.

The foregoing experiments identify a 42-bp sequence within the 5'-flanking region of the LDL receptor gene that confers sterol-responsivity when inserted into the promoter region of the HSV TK gene. This sequence consists of two imperfect direct repeats of 16 bp (designated repeats 2 and 3) plus a total of 10 bp of flanking sequences. Moreover, more recent experimentation have suggested to the inventors that the entire 42 bp sequence, although preferred, is not required for conferring sterol regulation. Rather, the 16 bases which comprise repeat 2 alone is sufficient. For example, the insertion of repeat 2 alone into the HSV TK promoter at −60, in either orientation, was found to confer sterolresponsivity on the hybrid promoter.

The 42-bp sequence is referred to as the sterol regulatory element 42 (SRE 42), and is located 35 bp upstream of the most 5' transcription initiation site in the LDL receptor gene (FIG. 1). The sequence between the SRE 42 and the cluster of transcription start sites at AT rich and may contain one or more TATA-like elements. About 20 bp upstream of repeat 2 of the SRE 42 there is an additional copy of the 16-bp sequence that is designated repeat 1.

The activity of the SRE 42 was analyzed by inserting a synthetic oligonucleotide into the complete HSV TK promoter at position −32 (FIG. 11). This construct retained all of the viral transcription elements required for TK expression. Abundant transcription of these genes was observed, and sterol suppression was obtained when the SRE 42 was present in either orientation (FIG. 11). When the same nucleotides were inserted in a scrambled fashion, no transcription was observed (plasmid I, in FIG. 11). Two copies of the SRE42 allowed transcription, and in this case the extent of suppression by sterols was maximal. More recent experiments have indicated that four or more repeats, inserted in either the forward or reverse direction, provides an ever more effective SRE.

When the SRE sequence was scrambled, transcription was no longer observed. Based on previous work, an insertion of 84 bp into the −32 position would be expected to abolish transcription. These data suggest that the SRE 42 contains both positive and negative elements. The positive element allows transcription of the TK promoter; the negative element allows this transcription to be repressed in the presence of sterols.

The present invention supports a model in which a single element of 42 bp contains a sequence that binds a positive transcription factor. Sterols might repress transcription by inactivating this positive transcription factor. This mechanism would be an inverse variation of that used in the lac operon of *E. coli* in which an inducer binds to the repressor and inactivates it. Alternatively, sterols might bind to a protein that in turn binds to the SRE 42 and prevents the positive transcription factor from binding. This mechanism would be analogous to the type of repression that occurs in the promoter of bacteriophage and would be consistent with current models of steroid hormone action in mammalian cells in which steroids bind to a receptor that in turn binds to specific sequences in DNA.

EXAMPLE III

Construction of an Expression Vector for Human Growth Hormone Using a Low Density Lipoprotein (LDL) Receptor Sterol Regulatory Element (SRE) Promoter Human growth hormone is a polypeptide hormone responsible for mediating normal human growth. The absence of this protein gives rise to the clinical syndrome of dwarfism, an abnormality that affects an estimated 1 in 10,000 individuals. Until recently, the sole source of growth hormone was pituitary extracts obtained in crude form from cadavers. The isolation and expression of the gene for growth hormone by scientists at Genentech provides an alternate source of this medically valuable protein. The present example describes the use of a DNA segment containing an LDL receptor sterol regulatory element that will allow the regulated expression of the human growth hormone gene product. As the overproduction of proteins not normally expressed in a given cell line (such as growth hormone in Chinese hamster ovary cells described here) frequently kills the host cell, the ability to use the LDL receptor SRE as a "protective" on/off switch represents a profound improvement in the production of growth hormone by genetic engineering methods.

Figure 13:
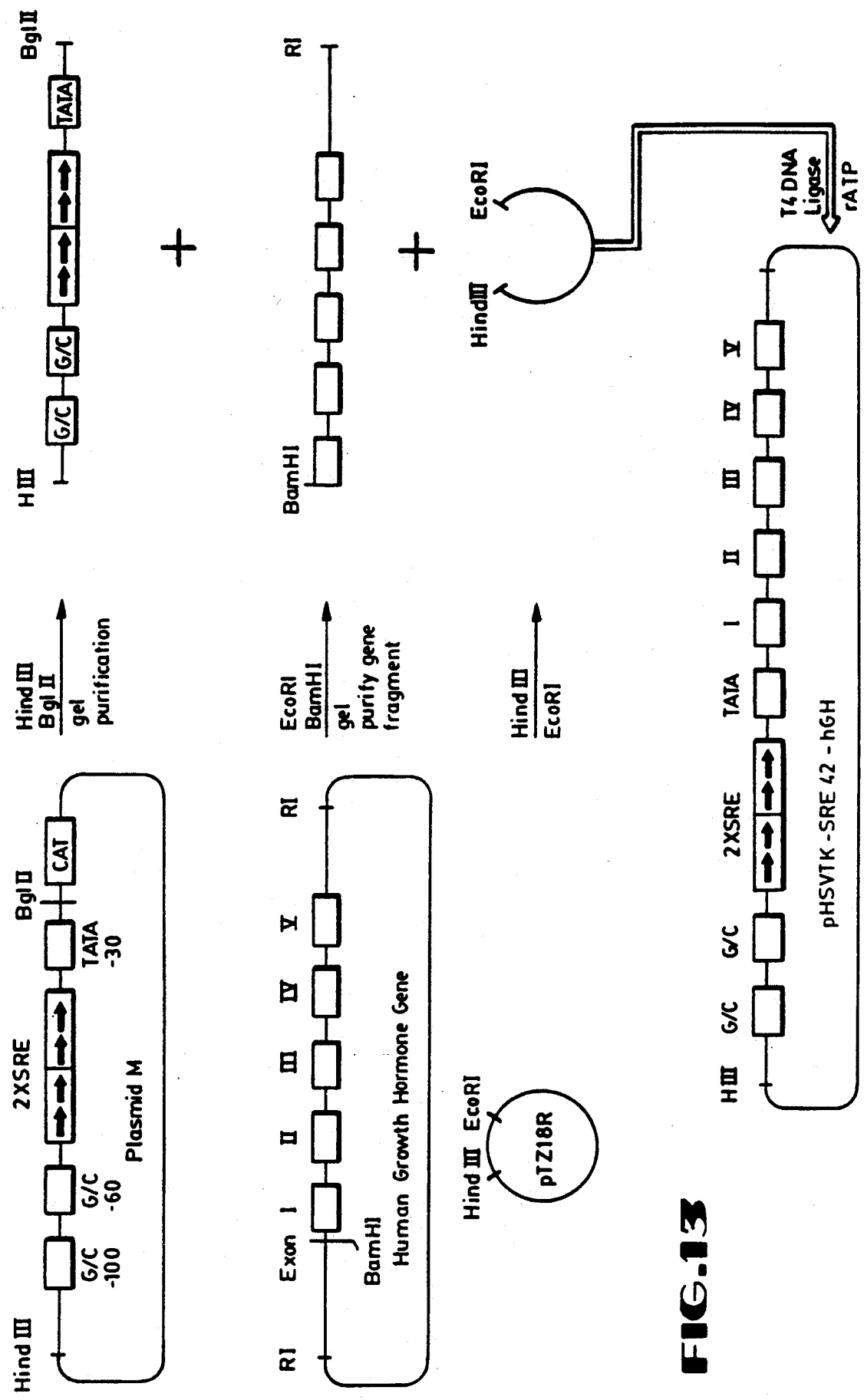
FIG. 13. Diagram demonstrating the construction of an expression vector for human growth hormone using an LDL receptor SRE promoter.

The construction of an expression vector using the SRE sequence of the present invention involves the fusion of such segments to the growth hormone gene. A strategy for making this construction is outlined below (see FIG. 13). It is recognized that other strategies, including those employing the polymerase chain reaction, could be used to accomplish this goal.

A DNA fragment of about 610 base pairs (bp) containing the Herpes Simplex Virus (HSV) promoter with 2 copies of the LDL receptor SRE is excised from the plasmid M of Example II (*E. coli* cells bearing plasmid M, (pHSVTK-SRE42), have been deposited with the ATCC on Mar. 30, 1987, and accorded ATCC designation 67376) by digestion with the restriction enzymes HindIII and BglII. The HSV promoter contains 3 signals required for its function as a promoter, these include two GC-box elements located at positions −100 and −60 and a TATA sequence located at position −30. As noted in Example II, the two copies of the 42 bp fragments which contains the LDL receptor SRE have been inserted just upstream of the HSVTK TATA sequence at position −32.

A DNA fragment containing the human growth hormone (hGH) gene is excised from a plasmid obtained as described in Seeburg (1982), DNA 1:239-249, by BamHI and EcoRI digestion. This 2150 bp fragment contains all five exons (coding sequences) of the hGH gene and a transcription termination region at the 3′ end of the gene near the EcoRI site.

The HSVTK-LDL receptor-SRE fragment and the hGH fragment are then ligated (see FIG. 13) to the recombinant transfer vector pTZ18R (Pharmacia Corp.) previously digested with the enzymes EcoRI and HindIII. The compatible sticky ends of the various DNA fragments are joined by the ligase under conditions described in Maniatis et al., supra. The resulting plasmid vector, pHSVTK-SRE42-hGH, is then introduced into a line of cultured CHO cells by calcium phosphate-mediated DNA transfection and the appropriate clone of cells expressing the growth hormone gene is selected by assaying the media for immune-reactive protein using antibodies against hGH (National Institutes of Health).

The controlled expression of the hGH gene is carried out by growing the line of CHO cells containing the transfected chimeric gene in the manner described in Example II. Briefly, the cells are maintained in Ham's F12 media supplemented with 10% calf lipoprotein-deficient serum, penicillin, streptomycin, and a mixture of cholesterol (10 ug/ml) and 25-hydroxycholesterol (0.5 ug/ml). The latter two sterols serve to keep the SRE element turned off, which serves to block the expression of the hGH gene. When the cells have reached confluency in the culture, the media is switched to the Ham's F12 containing the above additions but minus the two sterols. Removal of the sterols turns the SRE element on and allows expression of the hGH at high levels. In this manner the optimum amount of this product is generated by the cells for subsequent purification.

EXAMPLE IV

Construction of an Expression vector for Human Tumor Neorosis Factor (TNF) Using a Low Density Lipoprotein (LDL) Receptor Sterol Regulatory Element (SRE) Promoter Human tumor necrosis factor (TNF) is a protein released by mammalian monocyte cells in response to certain adverse stimuli. The protein has been shown to cause complete regression of certain transplanted tumors in mice and to have significant cytolytic or cytostatic activity against many transformed cell lines in vitro. To date, the extremely low levels of TNF released by monocytes have precluded its use as a general anticancer agent. The recent cloning of a TNF cDNA by scientists at Genentech Corporation (EP 168, 214A) has opened the way for the application of recombinant DNA techniques to the generation of large quantities of this protein. Described below is the use of an expression vector employing a powerful on/off switch embodied in the LDL receptor SRE to produce TNF in a regulated manner in Chinese hamster ovary (CHO) cells.

Figure 14:
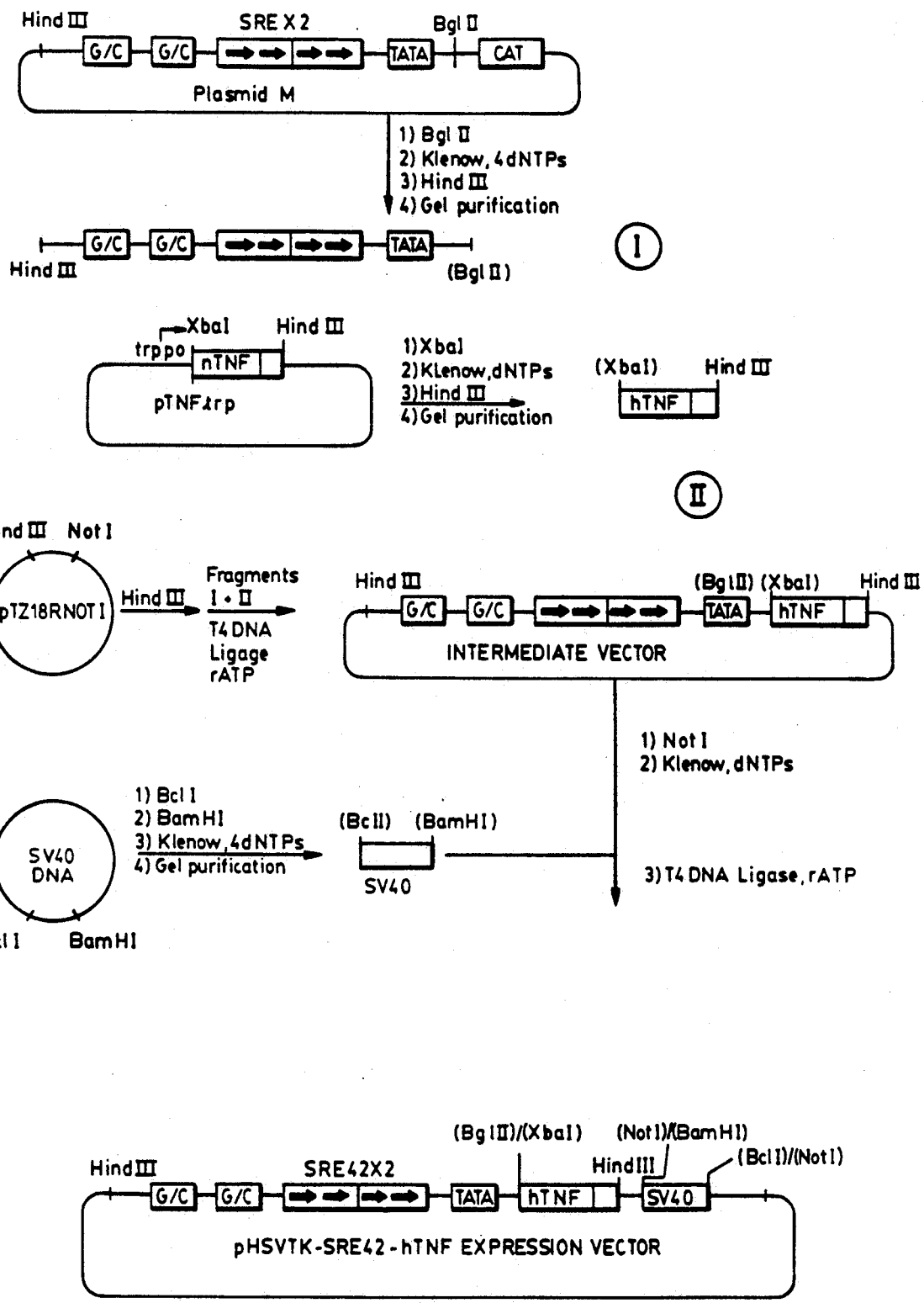
FIG. 14. Diagram demonstrating the construction of an expression vector for human tumor necrosis factor (TNF) using an LDL receptor SRE promoter.

The construction of this expression vector employs the steps outlined below (see FIG. 14).

First, a 610 base pair (bp) fragment containing two copies of the LDL receptor SRE inserted at position −32 of the Herpes Simplex Virus thymidine kinase promoter is isolated from plasmid M of Example II (ATCC Deposit number 67376). The plasmid is first restricted with the enzyme BglII to render the DNA linear and to free the 3′ end of the desired fragment. After BglIII digestion, the resulting 4 nucleotide (nt) sticky ends are made blunt-ended ended by treatment of the DNA fragment with the DNA polymerase I Klenow enzyme in the presence of the 4 deoxynucleoside triphosphates (dNTPs) as described in Maniatis et al, supra. After blunt-ending, the plasmid is restricted with the enzyme HindIII to release the 5′ end of the 610 bp fragment. This fragment is gel-purified on a low melting temperature agarose gel (Maniatis et al., supra) and held for preparation of the TNF cDNA fragment described below.

A DNA fragment encompassing the complete coding region of the human TNF cDN is excised from the plasmid pTNFtrp, obtained as described in EP 168,214A, in the following manner. First, the plasmid is linearized by digestion with the enzyme XbaI and the resulting sticky ends are filled in with the Klenow enzyme in the presence of the appropriate dNTPs. This manipulation frees the 5′ end of the TNF cDNA as a blunt-ended XbaI site. To release the cDNA from the linearized, EcoRI-digested, filled in plasmid a second digestion with the enzyme HindIII is performed. The resulting approximately 850 bp fragment is then gel purified on a low melting temperature agarose gel.

To join the HSVTK-LDL receptor SRE fragment to the TNF fragment, the two DNAs are mixed with an equimolar amount of the recombinant transfer vector pTZ18R-NotI, previously digested with HindIII, in the presence of adenosine triphosphate and the enzyme T4 DNA ligase. This enzyme will join the HindIII end of the vector to that of the HSVTK-SRE fragment, and the BglIII blunt end of this fragment to the XbaI blunt end of the TNF cDNA. Finally, it will join the HindIII end of the TNF fragment to that of the vector (see FIG. 14). After ligation, the DNA is transformed into E. coli cells by the calcium chloride procedure, and the desired clones having both the HSVTK-SRE and TNF fragments are identified and oriented with respect to the vector by colony hybridization and restriction mapping of mini-prep plasmid DNA.

The final step in the construction of the TNF expression vector employing an LDL receptor SRE promoter involves the insertion of a transcription termination and poly-adenylation signal at the 3′ end of the chimeric gene. For this purpose, a 200 bp DNA fragment containing these signals is excised from simian virus 40 DNA by digestion with the enzymes BamHI and BclI and the resulting sticky ends are rendered blunt-ended by treatment with the Klenow enzyme and the 4 dNTPs. This fragment is gel purified on a low melting agarose gel and ligated into the above intermediate vector containing the TNF gene linked to the HSVTK-SRE promoter. For this purpose, the plasmid is linearized at the unique NotI site, filled in with the Klenow enzyme, and then subjected to ligation with the simian virus DNA fragment. After transformation of the DNA into E. coli, plasmids having the viral DNA in the desired orientation are identified by restriction digestion and DNA sequencing.

To express the TNF cDNA in a regulated manner in CHO cells, the above expression vector is transfected into the cells as described in Example II. The desired cell line is identified by a cytotoxic assay as described by Pennica et al. (1984) Nature, 312:724). Once identified, the cells are grown in Ham's F12 medium supplemented with 10% lipoprotein-deficient serum, penicillin, streptomycin, and a mixture of cholesterol (10 ug/ml) and 25-hydroxy-cholesterol (0.5 ug/ml). When the cells are grown in the presence of the two sterols, the sterols enter the cell and inhibit the expression of the TNF gene by virtue of the 5'-located SRE sequence in the HSVTK promoter. This inhibition prevents excess TNF from accumulating in the cells or media before they have reached their apogee of growth. Once the cells have reached near confluency (i.e. maximum density) and are thus at their maximum production capabilities, the media is changed to one lacking sterols to induce expression of the transfected TNF gene. The absence of sterols causes a derepression of the SRE signal in the HSVTK promoter and a rapid turning on of the gene. This ability to regulate the expression of the TNF gene will allow the production of large quantities of media containing TNF in a most efficacious manner which avoids problems of cell toxicity caused by constant over-production of a foreign protein and problems of product (TNF) breakdown caused by proteases in the cells and media.

EXAMPLE V

Construction of an Expression vector for Human Tissue Plasminogen Activator (t-PA) Using a Low Density Lipoprotein (LDL) Receptor Sterol Regulatory Element (SRE) Promoter Human tissue plasminogen activator (t-PA) is a protein found in mammalian plasma which regulates the dissolution of fibrin clots through a complex enzymatic system (Pennica et al. (1983) Nature, 301:214–221). Highly purified t-PA has been shown to be potentially useful as an agent in the control of pulmonary embolisms, deep vein thromboses, heart attacks, and strokes. However, the extremely low levels of human t-Pa present in plasma have precluded its use as a general therapeutic agent. The recent cloning of a cDNA encoding human t-PA by scientists at Genentech Corporation (U.K. patent application 2,119,804) has opened the way for the application of recombinant DNA techniques to the generation of large quantities of this enzyme. Described below is the use of an expression vector employing a powerful on/off switch embodied in the LDL receptor SRE to produce t-PA in a regulated manner in Chinese hamster ovary (CHO) cells.

The construction of his expression vector employs several genetic engineering steps which are outlined below (see FIG. 15).

First, a 610 base pair (bp) fragment containing two copies of the LDL receptor SRE inserted at position −32 of the Herpes Simplex Virus thymidine kinase promoter is isolated from plasmid M of Example II. The plasmid is first restricted with the enzyme BglIII to render the DNA linear and to free the 3' end of the desired fragment. After BglIII digestion, the resulting 4 nucleotide (nt) sticky ends are made blunt-ended by treatment of the DNA fragment with the DNA polymerase I Klenow enzyme in the presence of the 4 deoxynucleoside triphosphates (dNTPs) as described in Maniatis et al., supra. After blunt-ending, the plasmid is restricted with the enzyme HindIII to release the 5' end of the 610 bp fragment. This fragment is gel-purified on a low melting temperature agarose gel and held for preparation of the t-PA cDNA fragment as described below.

A DNA fragment encompassing the complete coding region of the human t-PA cDNA is excised from the plasmid pT-PAtrp12 constructed as shown in U.K. Patent Application 2,119,804. First, the plasmid is linearized by digestion with the enzyme EcoRI and the resulting sticky ends are filled in with the Klenow enzyme in the presence of the appropriate dNTPs. This manipulation frees the 5' end of the t-PA cDNA as a blunt ended EcoRI site. To release the cDNA from the linearized, EcoRI-digested, filled in plasmid a second digestion with the enzyme PstI is performed. The resulting approximately 2,000 bp fragment is then gel purified on a low melting temperature agarose gel.

To join the HSVTK-LDL receptor SRE fragment to the t-PA fragment the two DNAs are mixed with an equimolar amount of the recombinant transfer vector pTZI8R-NotI, previously digested with HindIII and PstI, in the presence of adenosine triphosphate and the enzyme T4 DNA ligase. This enzyme will join the HindIII end of the vector to that of the HSVTK-SRE fragment, and the BglIII blunt end of this fragment to the EcoRI blunt end of the t-PA DNA. In addition it will join the PstI ends of the t-PA fragment and the vector (see FIG. 15).

The final step in the construction of the t-PA expression vector employing an LDL receptor SRE promoter involves the insertion of a transcription termination and poly-adenylation signal at the 3' end of the chimeric gene. For this purpose, a 200 bp DNA fragment containing these signals is excised from the simian virus 40 DNA by digestion with the enzymes BamHI and BclI and the resulting sticky ends are rendered blunt-ended by treatment with the Klenow enzyme and the 4 dNTPs. This fragment is gel purified on a low melting agarose gel and ligated into the above intermediate vector containing the t-PA gene linked to the HSVTK-SRE promoter. For this purpose, the plasmid is linearized at the unique NotI site, filled in with the Klenow enzyme, and then subjected to ligation with the simian virus DNA fragment. After transformation of the DNA into E. coli, plasmids having the viral DNA in the desired orientation are identified by restriction digestion and DNA sequencing.

To express the t-PA cDNA in a regulated manner in CHO cells, the above expression vector is transfected into the cells as described in Example II. The desired cell line is identified by immunological assay as described in Pennica et al., supra. Once identified, the cells are grown in Ham's F12 medium supplemented with 10% lipoprotein-deficient serum, penicillin, streptomycin, and a mixture of cholesterol (10 ug/ml) and 25-hydroxy-cholesterol (0.5 ug/ml). When the cells are grown in the presence of the 2 sterols, they enter the cell and inhibit the expression of the t-PA gene by virtue of the 5,-located SRE sequence in the HSVTK promoter. This inhibition prevents excess t-PA from accumulating in the cell or media before the cells have reached near maximum numbers. Once the cells have reached near confluency (i.e. maximum density) and are thus at their maximum production capabilities, the media is changed to one lacking sterols to induce expression of the transfected t-PA gene. The absence of sterols causes a derepression of the SRE signal in the HSVTK promoter and a rapid turning on of the gene. This ability to regulate the expression of the t-PA gene should allow the production of large quantities of media containing t-PA in a most efficacious manner which avoids problems of cell toxicity caused by constant overproduction of a foreign protein and problems of product (t-PA) breakdown caused by proteases in the cells and media.

EXAMPLE VI

Construction of Screening Cell Line pCH110 (Hall et al., *J. Mol. Appl. Gen.*, 2:101–109 (1983)) is digested with NcoI and the linearized plasmid cut within the SV40 promoter is recovered by gel electrophoresis. A synthetic oligonucleotide (SRE 42A) having the sequence

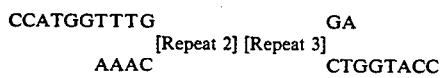

is prepared in vitro and ligated into linearized pCH110, transfected into *E. coli* 294 cells and selected on minimal plates containing ampicillin. Plasmids are isolated from transformant colonies. One colony harbors pCH110M, which by restriction analysis and sequencing is determined to contain a tandem repeat of SRE 42A in the 5'-3'-5'-3' direction in relation to the direction of transcription from the SV 40 early promoter of pCH110M.

HepG2 human liver cells (available from the American Type Culture Collection) are incubated for 4 hours with a mixture of pSV2neo (Southern et al., *J. Mol. Appl. Gen.*, 1:327–341 (1982)), pCH110M and DEAE-dextran using the method of McCutchan et al., *J. Natl. Cancer Inst.*, 41:351–356 (1968) or Sompayrac et al., *Proc. Natl. Acad. Sci. USA*, 78:7575–7578 (1981). Transformants are selected in Dulbecco's modified Eagle's medium containing 10% fetal calf serum and 1.25 mg/ml G418 (Schering-Plough) (selection medium). Individual colonies resistant to G418 are picked and grown in mass culture. They are then screened for the units of B-galactosidase activity in cell extracts according to Miller, *Experiments in Molecular Genetics*, Cold springs Harbor (1972), with protein concentration assayed by the Bradford procedure with bovine gamma-globulin as the standard (*Anal. Biochem.*, 72:248–254 (1976)). A positive clone, HepG2M, is selected which stably expresses B-galactosidase activity. Other host cells which are useful include CHO or murine tk minus cells. In addition, the cells also are transformed with a DHFR bearing plasmid and amplified cells identified by methotrexate selection.

An alternative construction comprises digesting pCH110 with KpnI and HpaI and recovering the B-galactosidase gene. Plasmids K or M are digested with appropriate restriction enzymes in order to obtain linearized plasmids from which the TK gene is deleted. The B-galactosidase gene is ligated into these plasmids using selected adaptors or linkers if necessary.

EXAMPLE VII

Candidate Screening Assay

HepG2M is seeded into microtiter wells containing selection medium and grown to confluence. The selection medium used for growth is exchanged for selection medium containing a 10.5 microgram/ml cholesterol admixture (20:1 cholesterol to 25-hydroxycholesterol by weight) in the following molar ratios of cholesterol to candidate: 100,000:1, 10,000:1, 1,000:1, 100:1, and 10:1. The cells are incubated for 48 hours in the presence of the selection medium containing cholesterol admixture as positive controls, mock treated cells as negative controls, and cholesterol:candidate proportions. Each series of wells is treated in duplicate. Thereafter, the cells in each well are fixed and stained in situ for B-galactosidase activity by adding X-Gal chromogen to each well, allowing color to develop and screening the wells with a spectrophotometric plate reader. Candidates which enhance B-galactosidase activity over the cholesterol repressed control are selected for further evaluation.

EXAMPLE VII

Further Characterization of the SRE

1. Procedures a. Materials

[gamma -$^{32}$P] (>5000 Ci/mmol) was obtained from ICN. Polynucleotide kinase was obtained from Pharmacia LKB Biotechnology Inc. Enzymes used in plasmid constructions were obtained from New England Biolabs, Boehringer Mannheim, and Bethesda Research Laboratories. Reverse transcriptase was purchased from Life Sciences (AMV 007). G418 sulfate (Geneticin) was purchased from GIBCO. Newborn calf lipoprotein-deficient serum (d>1.215 g/ml) was prepared by ultracentrifugation (Goldstein et al. 1983), *Meth. Enzymol.*, 98:241–260). Plasmid pSV3-Neo, which contains a bacterial gene that confers resistance to G418 (11), was obtained from Bethesda Research Laboratories. Plasmid pSVO-CAT (12) was kindly provided by Bruce Howard (National Institutes of Health). Plasmid pTK-CAT-1 contains the HSV thymidine kinase promoter (McKnight et al. (1982), *Science*, 217:316–324) extending 109-base pairs upstream of the mRNA cap site fused to the chloramphericol acetyltransferase (CAT) gene (Sudhof et al. (1987), *Cell*, 48:1061–1069). Oligonucleotides were synthesized on an Applied Biosystems model 380A DNA Synthesizer.

b. Plasmid Constructions

Standard protocols were used for all recombinant DNA technology (Maniatis et al. (1982), *Molecular Cloning: A Laboratory Manual*, Cold Spring Harbor Laboratory Press, NY., pp. 1–545). Plasmid p1471, previously referred to as pLDLR-CAT 1563 (Maniatis et al. Id. contains a 1507-base pair EcoRl-Alul restriction fragment encompassing the full-length human LDL receptor promoter (Sudlof et al. (1987), *Cey*, 48:1061–1069) inserted into pSVO-CAT. The promoter extends 1471 base pairs upstream from the transcription start site. Plasmid pSVO-CAT is a recombinant plasmid that contains the beta-lactamase gene (amp$^R$), the pBR322 origin of replication, and the coding sequences for CAT (Gorman et al. (1982), *Mol. Cell. Biol.*, 2:1044–1051). Plasmid pSVO-CAT has no defined eukaryotic promoter or enhancer sequences.

To construct point mutants A-R, oligonucleotide-directed mutagenesis (Zoller et al. (1984), *DNA*, 3:479–488) was performed with oligonucleotides of 20 nucleotides in length containing a mismatch 10 nucleotides from the 5' end. The inversion mutant pZ was made by oligonucleotide-directed mutagenesis using a 138-mer that hybridized to 30 nucleotides of the wild type sequence on either side of a 78-nucleotide target sequence. The 138-mer was constructed by ligating two contiguous 69 mers that were each annealed to a complimentary bridging 20-mer. The 138-mer was then purified on a denaturing polyacrylamide gel. All mutant promoters were reinserted into the HindIII site of pSVO-CAT.

c. Transfection

Chinese hamster ovary (CHO-K1) cells were grown in monolayer culture and transfected wither with 0.5 ug of pSV3 Neo, 22 ug of the test plasmid, and 3 ug of pTK-CAT-1 (Protocol 1) or with 0.5 ug pSV3-Neo, 20 ug of the test plasmid, and 5 ug pTK-CAT-1 (Protocol 2) by the calcium phosphate coprecipitation technique as described previously (Sudhof et al. (1987), *Cell,* 48:1061-1069; Sudhof et al. (1987), *J. Biol. Chem.,* 262:10773-10779). After two to three weeks of selection for resistance to G418 (1 mg/ml), resistant colonies were pooled (300-500 colonies/transfection) and expanded in mass culture in the presence of 1 mg/ml G418 and 10% fetal calf serum (Smith et al. (1988), *J. Biol. Chem.,* 263:18480-18487). The population of stable transfectants of a test plasmid was then incubated for 24 hr in medium containing calf lipoprotein-deficient serum in the absence or presence of sterols (10 ug/ml cholesterol plus 0.5 ug/ml 25-hydroxycholesterol) and harvested for RNA analysis as previously described (Sudhof et al. (1987), *Cell,* 48:106-1069; Sudhof et al. (1987), *J. Biol. Chem.,* 262:10773-10779).

d. Primer Extension Assays

Primer extension assays for measurement of mRNA were carried out as previously described with minor modifications (Sudhof et al. (1987), *J. Biol. Chem.,* 262:10773-10779; Gil et al. (1987), *Proc. Natl. Acad. Sci. USA,* 84:1863-1866). Primer was hybridized to 40 ug total cellular RNA for 45 min at 68° C., and the extension reaction was carried out for 1 hr at 42° C. Reaction products were subjected to electrophoresis on an inverted wedge gel, 40-cm in length, 1.5-mm in thickness at the negative electrode, and 0.4-mm in thickness at the positive electrode. To detect transcripts containing CAT sequences (derived from pTK-CAT-1 or from a test plasmid), an oligonucleotide primer of 40 nucleotides complimentary to bases 400-439 of the CAT mRNA (Alton et al. (1979), *Nature,* 282:864-869) was used. Two extension products of about 315 and 316 nucleotides in length are generated from pTK-CAT-1, owing to two transcription initiation sites within the HSV thymidine kinase promoter (McKnight et al. (1982), *Science,* 217:316-324). These transcripts serve as an internal control for transfection efficiency and RNA quantification. A 290-nucleotide extension produce is generated from p1471 and the various mutant derivative plasmids. MspI restriction fragments of $^{32}$P-labeled pBR322 DNA were used as size standards. Quantitative densitometry was performed with a Hoefer Scanning densitometer (Model GS300).

2. Results

Transcription assays were carried out in CHO cells that were transfected with plasmids containing the 5' flanking region of the LDL receptor gene fused to the CAT coding sequence. All constructions used an LDL receptor fragment that extended from +36 (relative to the start site for transcription) to −1471 (FIG. 16, upper half). The amount of mRNA in the permanently transfected cells was measured by a primer extension assay.

Cells transfected with p1471 (containing the wild-type LDL receptor promoter) produced relatively large amounts of mRNA when grown in the absence of sterols (FIG. 16, right lower panel, lane 1). For quantification, the autoradiograms were scanned densitometrically, and the amount of mRNA produced by the LDL receptor promoter was expressed relative to the amount produced by the HSV thymidine kinase promoter. The amount of mRNA produced by the p1471 plasmid in the absence of sterols was arbitrarily designated as 1.0. When sterols were added, the amount of mRNA from p1471 was reduced by 4.2-fold (FIG. 16, right lower panel; compare lanes 1 and 2). Stated another way, there was a 4.2-fold induction of transcription when sterols were removed from the culture medium.

To test for the orientation dependence of the sterol regulatory function, we prepared a plasmid, designated pZ, in which the segment from −33 to −110 Was inverted (FIG. 16, upper half). This segment contains the SRE-1. As shown in FIG. 16 (lower right panel, lanes 3 and 4), pZ behaved similarly to the wild-type LDL receptor promoter. There was a 3.8-fold induction of transcription when sterols were removed from the culture medium.

During the course of these experiments, some variability was noted from one transfection to another. To be certain that the observed regulation was not due to random fluctuations, multiple experiments were conducted with each plasmid. The left lower panel of FIG. 16 shows the average of four experiments in which p1471 and pZ was compared. From these data, it is clear that the inversion mutant led to a slight decrease in transcription both in the absence and presence of sterols, but that the fold induction in the absence of sterols occurred independently of the orientation of the sterol-regulated element.

To test for the effect of nucleotide substitutions in the SRE-1, a series of LDL receptor promoter plasmids were prepared in which a single nucleotide within repeat 2 was altered (FIG. 17). All of these substitutions were made within the sequence extending from −53 to −68, which includes the sterol regulatory element. Each plasmid was transfected into CHO cells on two separate occasions, and for each a pool of transfectants was studied on multiple occasions to assure statistical reliability of the results. A sample of the raw data from these experiments is shown in FIG. 18, and the results are summarized in FIG. 17.

Figure 17A:
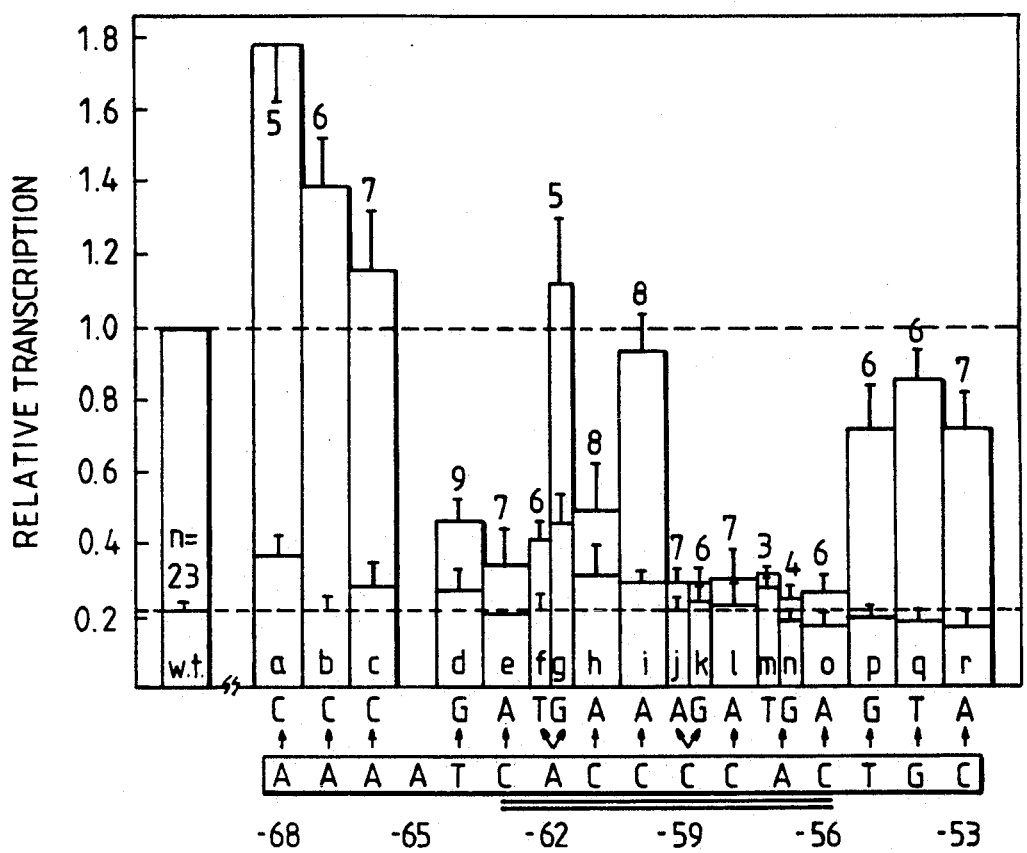
FIG. 17 (parts A and B). Nucleotide sequences and relative transcription rates of mutant LDL receptor promoters. The horizontal axis shows the sequence of repeat 2 of the human LDL receptor promoter. The eight nucleotides comprising the core SRE-1 sequence in repeat 2 are underlined. Arrows indicate point mutations, designated a-r. Panel A, the height of each bar represents the amount of LDL receptor-CAT mRNA produced from each plasmid relative to the amount of mRNA produced by the internal control (pTK-CAT-1) in each assay. The amount of mRNA produced by the wild-type LDL receptor promoter was arbitrarily assigned a value of 1.0. The data was derived from densitometric scans of autoadiograms as shown in FIG. 18. The data represent the relative transcription observed when cells were cultured in the absence (open bar) or presence (shaded bar) of sterols as described under "Experimental Procedures." The standard error of the mean (S.E.M.) of data for the given number of experiments (n with each mutant is plotted at the top of each bar. Panel B, fold induction of transcription from plasmids driven by the wild-type (w.t.) and mutant (a-r) LDL receptor promoters in transfected CHO cells grown in the presence and absence of sterols. Fold induction was calculated as described in the legend to FIG. 16 and plotted on the vertical axis. Each plasmid was transfected twice, once using Protocol 1 and once using Protocol 2. The data presented in Panels A and B represent the mean of 3023 experiments from both transfections for various plasmids. TK, thymidine kinase; LDLR, LDL receptor.
Figure 17B:
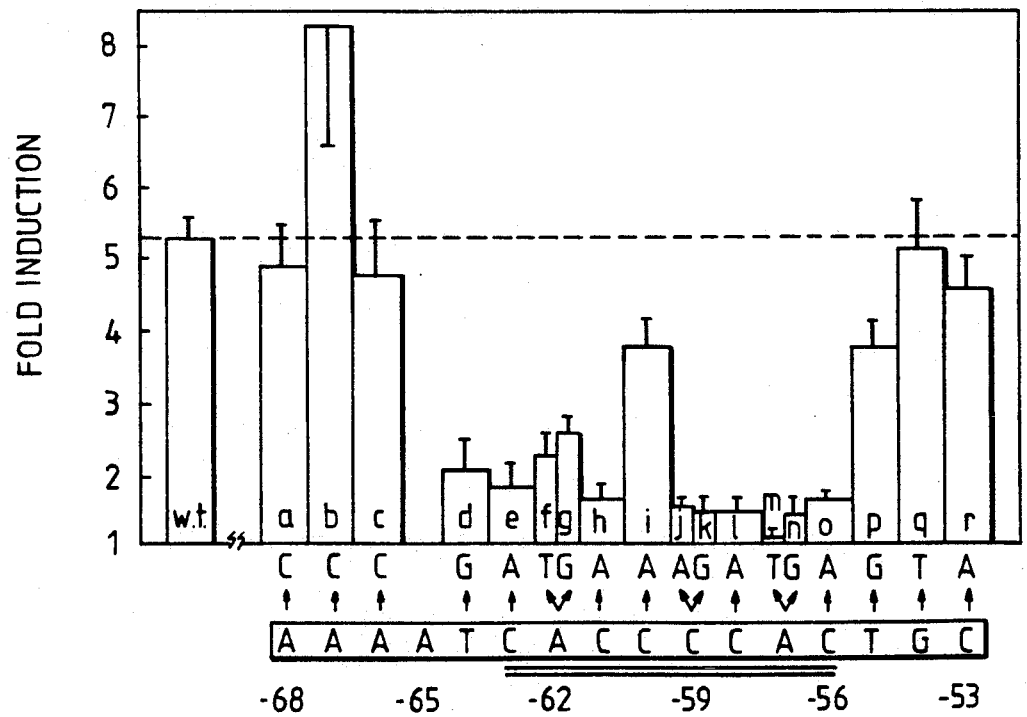
Figure 18A:
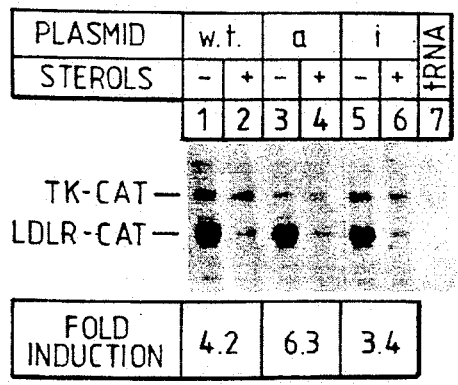
FIG. 18 (parts A-H). Expression of mutant LDL receptor promoters in transfected CHO cells incubated in the absence and presence of sterols. Each of the mutant LDL receptor promoters shown in FIG. 17 was fused to the CAT coding sequence and transfected into CHO cells together with a control plasmid containing the HSV thymidine kinase promoter fused to the CAT coding sequence (pTK-CAT-1). Transfections in Panels A-D and H were carried out according to Protocol 1; transfections in Panels E-G were carried out according to Protocol 2. Stably transfected colonies were selected, RNA was harvested from pooled colonies after growth in the absence and presence of sterols, and primer extension assays were performed. After drying, the gels shown in Panels A, B, C, D, E, F, G AND H were exposed to X-ray film at −70° C. with an intensifying screen for 33, 48, 41, 138, 120, 99, 99 and 138 hr, respectively. TK, thymidine kinase; LDLR, LDL receptor.
Figure 18B:
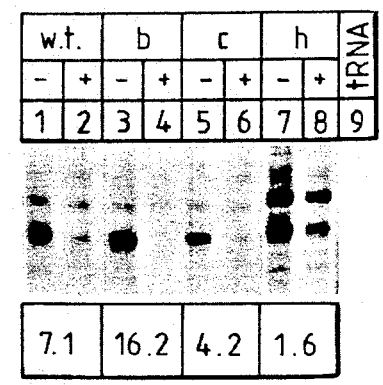
Figure 18C:
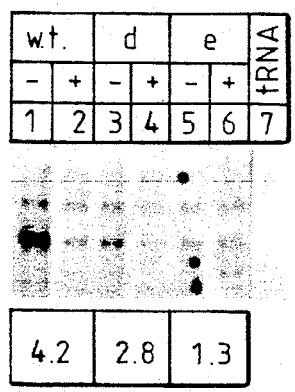
Figure 18D:
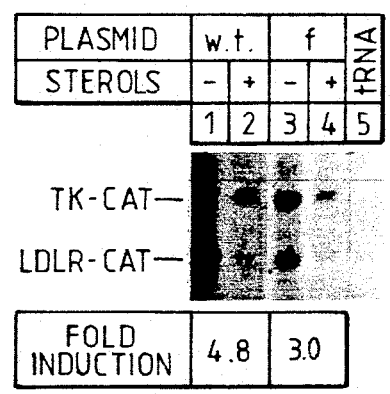
Figure 18E:
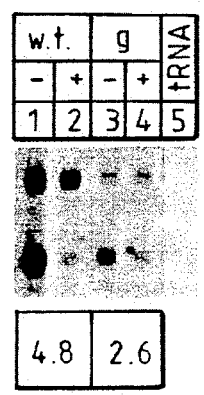
Figure 18F:
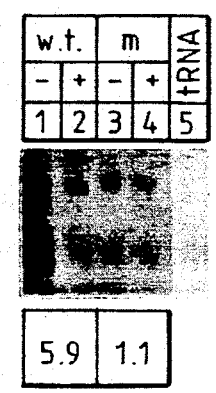
Figure 18G:
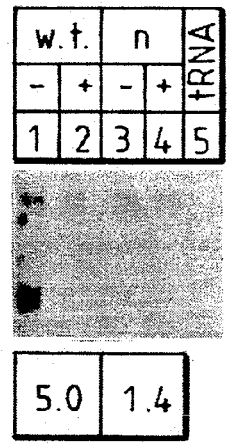
Figure 18H:
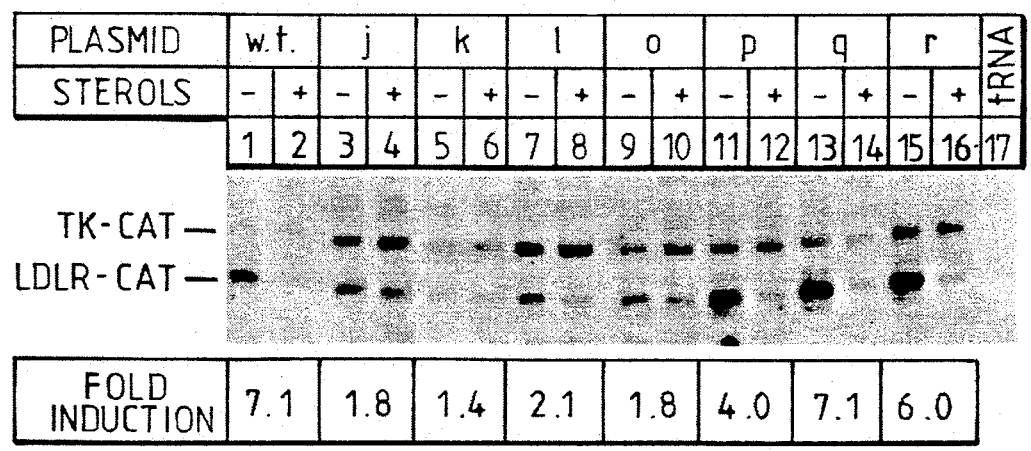

Based on the mean data from 23 experiments, the wild-type LDL receptor promoter gave approximately a 5-fold induction in the absence of sterols. Mutation of the promoter (−68, −67, and −66) did not alter this regulation (FIG. 17). These plasmids showed slightly higher transcription rates than the plasmid containing the wild-type promoter both in the absence and presence of sterols (FIG. 17A), but the fold induction was not impaired (FIG. 17B). A major disruption of regulation was seen when any one of the nucleotides in the TCAC sequence (−64 to −61) was altered by a transversion (change from purine to pyrimidine or vice versa). A similar decrease in regulation was seen with a transition mutation in which the A (−62) of the TCAC was changed to G (FIG. 17B). Mutation of the C at −60 had less of an effect (FIG. 17B). The next four nucleotides CCAC (−59 to −56) were each crucial for regulation. Transversion mutations at any of these four positions essentially abolished the induction of transcription in the absence of sterols. A single transition mutation was also made in this region (A to G at −57). This mutation also abolished regulation. The final three nucleotides in repeat 2 (TGC at −55 to −53) were not apparently important for regulation since transversion mutations had little effect (FIG. 17).

It is significant to note that none of the point mutations in FIG. 17 significantly reduced transcription in the presence of sterols (FIG. 17A). The mutations that abolish regulation did so by preventing the induction in the absence of sterols.

3. General Overview of Example VIII

The 8-base pair SRE-1 was originally identified as a region of sequence similarity within the sterol regulatory regions of the promoters for the LDL receptor, HMG CoA synthase, and HMG CoA reductase genes (Smith et al. (1988), Jrnl. Biol. Chem., 263:18480-18487. In the LDL receptor the SRE-1 was found within the 16-base pair repeat 2 which had been shown to contain the information necessary for sterol-mediated regulation (Sudhof et al. (1987), Cell, 48:1061-1069; Dawson et al. (1988), J. Biol. Chem., 263:3372-3379). Prior to this study, no definitive evidence was available to show that the eight nucleotides comprising the SRE-1 encompassed the essential element for sterol regulation. The current study shows that the 8-base pair SRE-1, situated within repeat 2, carries most of the information necessary for this control. In addition, the two adjacent upstream nucleotides at positions −64 and −65 appear to be involved.

Substitution of any single nucleotide within the 8-base pair core SRE-1 markedly limited inducibility in the absence of sterols with the sole exception of the C at position −60. When this pyrimidine was changed to a purine (A), transcription remained inducible by nearly 4-fold. It is noteworthy that in the Syrian hamster LDL receptor gene, this position is occupied by an A. All other mutations within the SRE-1 reduced inducibility below 2.5-fold; nucleotides at these positions are all conserved in the human and hamster promoters.

In general, mutations in the tetramer at the 3' end of the core SRE-1 (CCAC) had a more profound effect than mutations in the 5' tetramer (CCAC) (FIG. 17). The T at position −64 immediately adjacent to the core SRE-1 also played a role in regulation since substitution of a G reduced the induction. In this study the adjacent A at position −76 was not altered. In a previous study which the repeat 2 sequence was inserted into the HSV thymidine kinase promoter, this A was changed to a C (mutant L in Ref. 4), and this substitution reduced the amplitude of sterol regulation by 75%. These studies thus localize the regulatory region of the 16-base pair repeat 2 to the central 10 base pairs. The three base pairs at either end of repeat 2 are not important for sterol-dependent regulation since substitutions in these positions did not impair regulation.

None of the point mutations in the SRE-1 or other regions of repeat 2 led to a constitutively high level of transcription from the LDL receptor promoter. The only result was a failure of induction following the removal of sterols from the culture medium. These data strongly suggest that in the intact LDL receptor promoter, the SRE-1 acts as a binding site for a conditionally positive activator protein that enhances transcription in the absence of sterols and loses this effect in the presence of sterols. No evidence was found that the SRE-1 acts as the binding site for a repressor protein. This interpretation agrees with the conclusion drawn from studies of point mutations in both SRE-1 sequences of the HMG CoA synthase promoter (Smith et al. (1988), J. Biol. Chem., 263:18480-18487). A comparative level of detail is not yet available for the putative SRE-1 in the HMG CoA reductase promoter.

On the basis of the current experiments with the native LDL receptor promoter, it is concluded that the SRE-1 functions as an enhancer only in the absence of sterols. A working model suggests that cells contain a protein that binds to the SRE-1 and activates transcription in the absence of sterols and that this function is inactivated as sterols accumulate within the cell. Current efforts are directed toward the identification of such a sterol-sensitive, trans-acting enhancer protein that demonstrates binding specificity for the SRE-1.

The current studies define the nucleotides that are required for the function of the SRE-1 in the context of the intact LDL receptor promoter. Certain substitutions that are not tolerated in the LDL receptor promoter might be tolerated in the SRE-1 sequence of other genes. In the putative SRE-1 of the HMG CoA reductase promoter, the C at the 5th position in the octamer (corresponding to position −59 in the LDL receptor promoter) is replaced by a G. Although this substitution destroys SRE-1 function in the LDL receptor promoter (FIG. 17), it might not have that effect in the HMG CoA reductase promoter because of compensatory substitutions at other nucleotides that flank the SRE-1. In addition, the interaction of a protein with the SRE-1 in the HMG CoA reductase promoter might be stabilized by protein-protein interactions with neighboring DNA binding proteins so that binding of the sterol regulatory protein is not abolished by this single nucleotide change.

The foregoing examples, both actual and prophetic, demonstrate experiments performed and contemplated by the present inventors in the development of the invention. It is believed that these examples include a disclosure of techniques which serve to both apprise the art of the practice of the invention and, additionally, serve to demonstrate its usefulness in a number of settings and to disseminate general knowledge which relates peripherally to more central aspects of the invention as defined by the appended claims. However, it will be appreciated by those of skill in the art that the techniques and embodiments disclosed herein are preferred embodiments only and that in general, numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

What is claimed:

1. A substantially purified segment of DNA comprising a functionally translocatable sterol regulatory element capable of conferring sterol mediated regulation of structural gene transcription to a selected heterologous structural gene when located upstream from and proximal to a transcription initiation site of such a gene, provided that said segment is free of the structural gene ordinarily under the transcriptional control of said sterol regulatory element, the element including a nucleotide sequence selected from one of the following:

5'-C-A-C-C-C-C-A-C-3'
5'-C-A-C-A-C-C-A-C-3'

5'-C-A-C-C-G-C-A-C-3'
5'-C-A-C-C-T-A-C-3'
or the complement of such a sequence.

2. The DNA segment of claim 1, defined further as a segment of from 8 to 50 nucleotides in length.

3. The DNA segment of claim 1, defined further as a segment of from 8 to 27 nucleotides in length.

4. The DNA segment of claim 1 further comprising a functionally translocatable positive gene promoter control element capable of enhancing the transcription rate of such an associated structural gene when located upstream from and proximal to such a transcription initiation site.

5. The DNA segment of claim 4 wherein said positive control element comprises a nucleic acid sequence of:
   (a) 5'-A-A-A-C-T-C-C-T-C-C-T-C-T-T-G-C-3';
   (b) 5'-A-A-A-C-T-C-C-T-C-C-C-C-C-T-G-C-3';
   (c) 5'-G-C-A-A-G-A-G-G-A-G-G-A-G-T-T-T-3'; or
   (d) 5'-G-C-A-G-G-G G-G-A-G-G-A-G-T-T-T-3'.

6. The DNA segment of claim 4 wherein said positive control element comprises a nucleic acid sequence of:

(X)$_n$ wherein n=1–5, each X being independently selected from DNA segments having a nucleotide sequence of:
   (a) 5'-A-A-A-C-T-C-C-T-C-C-T-C-T-T-G-C-3';
   (b) 5'-A-A-A-C-T-C-C-T-C-C-C-C-C-T-G-C-3';
   (c) 5'-G-C-A-A-G-A-G-G-A-G-G-A-G-T-T-T-3'; or
   (d) 5'-G-C-A-G-G-G-G-G-A-G-G-A-G-T-T-T-3';
with each X unit, if more than one, being separated by from 0 to 20 nucleotides selected from the group of nucleotides consisting of A, G, C and T.

7. The DNA segment of claim 4 comprising a nucleic acid sequence of:

(X)$_n$ wherein n=1–5, each X being independently selected from DNA segments having a nucleotide sequence of:
   (a) 5'-A-A-A-A-T-C-A-C-C-C-C-A-C-T-G-C-A-A-A-C-T-C-C-T-C-C-C-C-T-G-C-3'; or
   (b) 5'-G-C-A-G-G-G-G-G-A-G-G-A-G-T-T-T-G-C-A-G-T-G-G-G-G-T-G-A-T-T-T-T-3';
with each X unit, if more than one, being separated by from 0 to 10 nucleotides selected from the group of nucleotides consisting of A, G, C and T.

8. A DNA molecule comprising a DNA segment having a sterol regulatory element in accordance with claim 1 in combination with a structural gene not ordinarily under the transcriptional control of said element, said structural gene and sterol regulatory element being combined in a manner such that said structural gene is under the transcriptional control of said regulatory element.

9. The DNA molecule of claim 8 wherein said selected structural gene comprises the structural gene for t-PA, human growth hormone, activin, interferon, inhibin, interleukin I, interleukin II or beta-galactosidase.

10. The DNA segment of claim 1, including within its nucleotide sequence a nucleotide sequence selected from one of the following:
   (a) 5'-A-G-T-T-T-G-C-A-G-T-G-G-G-G-T-G-A-T-T-T-T-C-A-A-A-T-G-3';
   (b) 5'-A-G-T-C-T-G-C-A-G-T-G-G-T-G-T-G-A-T-T-T-T-C-A-A-A-A-G-3';
   (c) 5'-A-G-T-C-T-G-C-A-G-T-G-G-G-G-T-G-A-T-T-T-T-C-A-A-A-A-A-3';
   (d) 5'-G-A-G-A-G-A-T-G-G-T-G-C-G-G-T-G-C-C-T-G-T-T-C-T-T-G-G-3';
   (e) 5'-G-A-G-A-G-A-T-G-G-T-G-C-G-G-T-G-C-C-C-G-T-T-C-T-C-C-G-3';
   (f) 5'-A-C-G-G-T-G-A-C-G-T-A-G-G-G-T-G-G-C-C-C-G-A-G-A-A-C-A-3'; or
   (g) 5'-C-G-G-G-G-G-A-A-G-T-G-G-G-G-T-G-A-G-A-C-G-G-T-G-A-C-G-3'; or
the complement of any of these sequences.

11. The DNA segment of claim 1, wherein the element comprises -C-A-C-C-C-C-A-C-, or its complement.

12. The DNA segment of claim 1, wherein the element comprises -C-A-C-A-C-C-A-C-, or its complement.

13. The DNA segment of claim 1, wherein the element comprises -C-A-C-C-G-C-A-C-, or its complement.

14. The DNA segment of claim 1, wherein the element comprises -C-A-C-C-C-T-A-C-, or its complement.

15. A substantially purified segment of DNA comprising a functionally translocatable sterol regulatory element capable of conferring sterol mediated regulation of structural gene transcription to a selected structural gene when located upstream from and proximal to a transcription initiation site of such a gene, the element including a nucleotide sequence selected from one of the following:
   a) 5'-A-A-C-C-C-C-A-C-3';
   b) 5'-C-T-C-C-C-C-A-C-3';
   c) 5'-C-G-C-C-C-C-A-C-3';
   d) 5'-C-A-A-C-C-C-A-C-3'; and
   e) 5'-C-A-C-A-C-C-A-C-3';
or the complement of such a sequence.

16. The DNA segment of claim 15, wherein the element comprises -A-A-C-C-C-C-A-C-, or its complement.

17. The DNA segment of claim 15, wherein the element comprises -C-T-C-C-C-C-A-C-, or its complement.

18. The DNA segment of claim 15, wherein the element comprises -C-G-C-C-C-C-A-C-, or its complement.

19. The DNA segment of claim 15, wherein the element comprises -C-A-A-C-C-C-A-C-, or its complement.

20. The DNA segment of claim 15, wherein the element comprises -C-A-C-A-C-C-A-C-, or its complement.

21. A recombinant DNA vector comprising a DNA segment as defined by anyone of claims 1, 2, 3, 4 through 7, 10 through 14 or 15–20 or DNA molecule as defined by claim 8 or 9.

22. A recombinant cell comprising a recombinant DNA vector as defined by claim 21.

23. A method for sterol regulating expression of a polypeptide in recombinant cell culture comprising:
(a) preparing a first DNA segment as defined by anyone of claims; 4–7, or 11–14 or 15–20.
(b) constructing a second DNA segment by positioning said first DNA segment upstream from and proximal to a transcription initiation site of a selected structural gene such that said structural gene may be brought under the transcriptional control of the sterol regulatory element of said first DNA segment;
(c) transforming a host cell with said second DNA segment; and presence of a sterol in amounts and for a time sufficient to suppress transcription of said structural gene.

24. The method of claim 23 wherein said selected heterologous structural gene comprises the structural gene for t-PA, human growth hormone, activin, interferon, inhibin, human tumor necrosis factor, interleukin I, interleukin II or beta-galactosidase.

* * * * *

UNITED STATES PATENT AND TRADEMARK OFFICE
CERTIFICATE OF CORRECTION

PATENT NO. : 5,256,545
DATED : October 26, 1993
INVENTOR(S) : Michael S. Broen, Joseph L. Goldstein, David W. Russell, and Thomas C. Sudhof It is certified that error appears in the above-indentified patent and that said Letters Patent is hereby corrected as shown below:

Column 50, line 68, after ";and" add a return and start a new paragraph --(d) culturing the transformed host cell in the--.

Signed and Sealed this

Tenth Day of May, 1994

Attest:

BRUCE LEHMAN

*Attesting Officer*     *Commissioner of Patents and Trademarks*